(12) United States Patent
Callewaert et al.

(10) Patent No.: US 11,999,797 B2
(45) Date of Patent: Jun. 4, 2024

(54) METHODS OF TREATING INITIAL EPISODE OF TTP WITH IMMUNOGLOBULIN SINGLE VARIABLE DOMAINS

(71) Applicant: Ablynx N.V., Ghent-Zwijnaarde (BE)

(72) Inventors: Filip Callewaert, Zulte (BE); Hilde De Winter, Heusden (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 137 days.

(21) Appl. No.: 16/967,514

(22) PCT Filed: Feb. 6, 2019

(86) PCT No.: PCT/EP2019/052929
§ 371 (c)(1),
(2) Date: Aug. 5, 2020

(87) PCT Pub. No.: WO2019/154867
PCT Pub. Date: Aug. 15, 2019

(65) Prior Publication Data
US 2021/0221912 A1  Jul. 22, 2021

Related U.S. Application Data

(60) Provisional application No. 62/662,381, filed on Apr. 25, 2018, provisional application No. 62/627,082, filed on Feb. 6, 2018.

(51) Int. Cl.
*C07K 16/36* (2006.01)
*A61K 39/00* (2006.01)

(52) U.S. Cl.
CPC ........ *C07K 16/36* (2013.01); *A61K 2039/505* (2013.01); *A61K 2039/545* (2013.01); *C07K 2317/24* (2013.01); *C07K 2317/35* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,270,976 B2 | 9/2007 | Greenfield et al. | |
| 7,807,162 B2 | 10/2010 | Silence et al. | |
| 8,372,398 B2 | 2/2013 | Silence et al. | |
| 10,858,445 B2 * | 12/2020 | Duby | C07K 16/36 |
| 10,919,980 B2 * | 2/2021 | Duby | A61P 7/02 |
| 2017/0210822 A1 | 7/2017 | Duby | |
| 2018/0155440 A1 | 6/2018 | Duby | |
| 2018/0155441 A1 | 6/2018 | Duby | |
| 2018/0155442 A1 | 6/2018 | Duby | |
| 2018/0155443 A1 | 6/2018 | Duby | |

FOREIGN PATENT DOCUMENTS

| | | | |
|---|---|---|---|
| EP | 0294025 A2 | 12/1988 | |
| EP | 0294025 A3 | 11/1989 | |
| IN | 255610 B | 3/2013 | |
| JP | 2017-519762 A | 7/2017 | |
| RU | 2364420 C2 | 8/2009 | |
| RU | 2433139 C2 | 11/2011 | |
| RU | 2524129 C2 | 7/2014 | |
| WO | WO 2006/122825 A2 | 11/2006 | |
| WO | WO 2012/171031 A1 | 12/2012 | |
| WO | WO 2013/024059 A2 | 2/2013 | |
| WO | WO-2013024059 A2 * | 2/2013 | ............... A61P 1/04 |
| WO | WO 2015/193326 A1 | 12/2015 | |
| WO | WO-2015193326 A1 * | 12/2015 | ............. A61K 38/36 |

OTHER PUBLICATIONS

Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Ghahroudi et al., FEBS Letters Sep. 15, 1997; 414(3): 521-526.*
Kanyavuz et al., Nat Rev Immunol. Jun. 2019;19(6):355-368. doi: 10.1038/S41577-019-0126-7.*
Peyvandi et al., N Engl J Med. Feb. 11, 2016;374(6):511-22. doi: 10.1056/NEJMoa1505533. PMID: 26863353.*
Supplementary Appendix to Peyvandi F, Scully M, Kremer Hovinga JA, et al. Caplacizumab for acquired thrombotic thrombocytopenia purpura. N Engl J Med 2016;374:511-22. DOI: 10.1056/NEJMoa1505533, 30 pages.*
PCT/EP2019/052929, dated May 2, 2019, International Search Report and Written Opinion.
Peyvandi et al., Caplacizumab for Acquired Thrombotic Thrombocytopenic Purpura. N Engl J Med. Feb. 11, 2016;374(6): 511-22. doi: 10.1056/NEJMoa1505533.

(Continued)

*Primary Examiner* — Michael Szperka
(74) *Attorney, Agent, or Firm* — Wolf, Greenfield & Sacks, P.C.

(57) ABSTRACT

The present invention is based on the finding that administration of polypeptides comprising two immunoglobulin single variable domains (ISVD) against von Willebrand Factor (vWF) to human patients with an initial episode of thrombotic thrombocytopenic purpura (TTP) episode results in improved outcomes, including a faster time to platelet count response lower proportion of patients with either death, recurrence or a major thromboembolic event (TE) during the treatment period, lower recurrence rate, and prevention of refractoriness. The invention provides a polypeptide comprising two ISVD against vWF for use in treating a vWF-related disease, preferably TTP, in a human in need thereof. The invention further relates to dosage unit forms, kits and medical uses for treating TTP.

20 Claims, 5 Drawing Sheets

Specification includes a Sequence Listing.

(56) References Cited

OTHER PUBLICATIONS

Peyvandi et al., Caplacizumab reduces the frequency of major thromboembolic events, exacerbations and death in patients with acquired thrombotic thrombocytopenic purpura. J Thromb Haemost. Jul. 2017;15(7):1448-1452. doi: 10.1111/jth.13716. Epub Jun. 5, 2017.
Scully et al., Caplacizumab Treatment for Acquired Thrombotic Thrombocytopenic Purpura. N Engl J Med. Jan. 24, 2019;380(4):335-346. doi: 10.1056/NEJMoa1806311. Epub Jan. 9, 2019.
Scully et al., Results of the Randomized, Double-Blind, Placebo-Controlled, Phase 3 Hercules Study of Caplacizumab in Patients with Acquired Thrombotic Thrombocytopenic Purpura. Blood. Dec. 7, 2017;130(Supplement 1):LBA-1. doi: 10.1182/blood.V130.Suppl_1.LBA-1.LBA-1. 8 pages.
Kuznetsova, Brackets in text of legal document as a linguistic and cognitive phenomenon. Vestnik MGOU, Series: Russian Philology. 2015;3:37-43.
Roitt et al., Immunology. Moscow. Mir. 2000:110-1.
Singer et al., Genes and Genomes: A Changing Perspective. Moscow. Mir. 1998;1:63-4.
Joly et al., Thrombotic thrombocytopenic purpura. Blood. May 25, 2017;129(21):2836-2846. doi: 10.1182/blood-2016-10-709857. Epub Apr. 17, 2017.
Koloskov, Willebrand's disease. Health and Education in the XXI century. 2017;19(11):43. doi: 10.26787/nydha-2226-7425-2017-19-11-43-48.
[No Author Listed] Study to Assess Efficacy and Safety of Anti-von Willebrand Factor Nanobody in Patients with Acquired Thrombotic Thrombocytopenic Purpura (TTP) (TITAN). NIH US National Library of Medicine. Jun. 28, 2010. https://clinicaltrials.gov/ct2/show/NCT01151423.
Bartunek et al., Abstract 15084; Safety and Efficacy of Anti-von Willebrand Factor Nanobody® ALX-0081 in Stable Angina Patients Undergoing Percutaneous Coronary Intervention. Circulation. 2010;122:A15084.
Bartunek et al., Abstract 2009: ALX-0081 a Novel Anti-Thrombotic: Results of a Single Dose Phase 1 Study in Healthy Volunteers and Further Development in Patients with Stable Angina Undergoing PCI. Circulation. 2008;118:S656.
Callewaert et al., Evaluation of efficacy and safety of the anti-VWF Nanobody ALX-0681 in a preclinical baboon model of acquired thrombotic thrombocytopenic purpura. Blood. Oct. 25, 2012;120(17):3603-10. doi:10.1182/blood-2012-04-420943. Epub Sep. 4, 2012.
Cataland et al., Caplacizumab Treatment for Acquired Thrombotic Thrombocytopenic Purpura. N Engl J Med. Jan. 24, 2019;380(4):335-346. doi: 10.1056/NEJMoa1806311. Epub Jan. 9, 2019.
Cataland et al., Practical issues in ADAMTS13 testing and emerging therapies in thrombotic thrombocytopenic purpura. Semin Hematol. Oct. 2011;48(4):242-50. doi: 10.1053/j.seminhematol.2011.08.004.
Chapman et al., Therapy for thrombotic thrombocytopenia purpura: past, present, and future. Semin Thromb Hemost. Feb. 2014;40(1):34-40. doi:10.1055/s-0033-1363165. Epub Dec. 31, 2013.
Galstyan et al., [Treatment of thrombotic thrombocytopenic purpura]. Ter Arkh. Jul. 23, 2021;93(7):826-829. Russian. doi: 10.26442/00403660.2021.07.200914.
Gauer et al., Thrombocytopenia. Am Fam Physician. 2012;85(6):612-622.
Holz, The Titan trial—assessing the efficacy and safety of an anti-von Willebrand factor Nanobody in patients with acquired thrombotic thrombocytopenic purpura. Transfus Apher Sci. Jun. 2012;46(3):343-6. doi:10.1016/j.transci.2012.03.027. Epub Apr. 3, 2012.
Hussain et al., Aspirin and immune system. Int Immunopharmacol. Jan. 2012;12(1):10-20. doi: 10.1016/j.intimp.2011.11.021. Epub Dec. 13, 2011.
Knobl, Inherited and acquired thrombotic thrombocytopenic purpura (TTP) in adults. Semin Thromb Hemost. Jun. 2014;40(4):493-502. doi: 10.1055/s-0034-1376883. Epub May 6, 2014.
Kremer Hovinga et al., Survival and relapse in patients with thrombotic thrombocytopenic purpura. Blood. Feb. 25, 2010;115(8):1500-11; quiz 1662. doi: 10.1182/blood-2009-09-243790. Epub Dec. 23, 2009.
Mcleod et al., Therapeutic apheresis: use of human serum albumin, fresh frozen plasma and cryosupernatant plasma in therapeutic plasma exchange. Best Pract Res Clin Haematol. 2006;19(1):157-67.
Moake et al., Therapy of chronic relapsing thrombotic thrombocytopenic purpura with prednisone and azathioprine. Am J Hematol. Sep. 1985;20(1):73-9. doi: 10.1002/ajh.2830200110.
Neunert et al., The American Society of Hematology 2011 evidence-based practice guideline for immune thrombocytopenia. Blood. Apr. 21, 2011;117(16):4190-207. doi: 10.1182/blood-2010-08-302984. Epub Feb. 16, 2011.
Peyvandi et al., First results of the Phase II Titan trial: anti-von Willebrand factor Nanobody® as adjunctive treatment for patients with acquired thrombotic thrombocytopenic purpura. Jul. 28, 2011. Retrieved from the Internet: http://www.ablynx.com/wp-content/uploads/2011/07/Peyvandi TITAN-study final.pdf on Jan. 21, 2015.
Peyvandi et al.: ADAMTS13 and anti-ADAMTS13 antibodies as markers for recurrence of acquired thrombotic thrombocytopenic purpura during remission. Haematologica. Feb. 2008;93(2):232-9. doi: 10.3324/haematol.11739. Epub Jan. 26, 2008.
Sargentini-Maier et al., Clinical pharmacology of caplacizumab for the treatment of patients with acquired thrombotic thrombocytopenic purpura. Expert Rev Clin Pharmacol. Jun. 2019;12(6):537-545. doi: 10.1080/17512433.2019.1607293. Epub Apr. 28, 2019.
Scully, Rituximab in the treatment of TTP. Hematology. Apr. 2012; 17 Suppl 1:S22-4. doi: 10.1179/102453312X13336169155178. 3 pages.
Third Party Observations for Application No. EP 18153674, dated Feb. 9, 2022. 48 pages.
Third Party Observations for Application No. EP 18153674, dated Jan. 13, 2022. 5 pages.
Ulrichts et al., Antithrombotic drug candidate ALX-0081 shows superior preclinical efficacy and safety compared with currently marketed antiplatelet drugs. Blood. Jul. 21, 2011;118(3):757-65. doi: 10.1182/blood-2010-11-317859. Epub May 16, 2011.
Van Audenhove et al., Nanobodies as Versatile Tools to Understand, Diagnose, Visualize and Treat Cancer. EBioMedicine. Jun. 2016;8:40-48. doi: 10.1016/j.ebiom.2016.04.028. Epub Apr. 30, 2016.
Vanhoorelbeke et al., Animal models for thrombotic thrombocytopenic purpura. J Thromb Haemost. 2013;11 Suppl 1:2-10. doi:10.1111/jth.12255.
Voitsekhovskii et al., Diagnosis and Treatment of Thrombotic Thrombocytopenic Purpura Developed During Gestation: Literature Review and Case Report. Klin Onkogematol. 2014;7(4):587-98.
Westwood et al., Rituximab for thrombotic thrombocytopenic purpura: benefit of early administration during acute episodes and use of prophylaxis to prevent relapse. J Thromb Haemost. Mar. 2013;11(3):481-90. doi: 10.1111/jth.12114.
Youming, Intractable Internal Medicine Diseases and Clincal Analysis. Hanzhou. Zheijiang University Pres. Aug. 2007:262-265. 5 pages.
PCT/EP2019/052929, dated Aug. 20, 2020, International Preliminary Report on Patentability.

\* cited by examiner

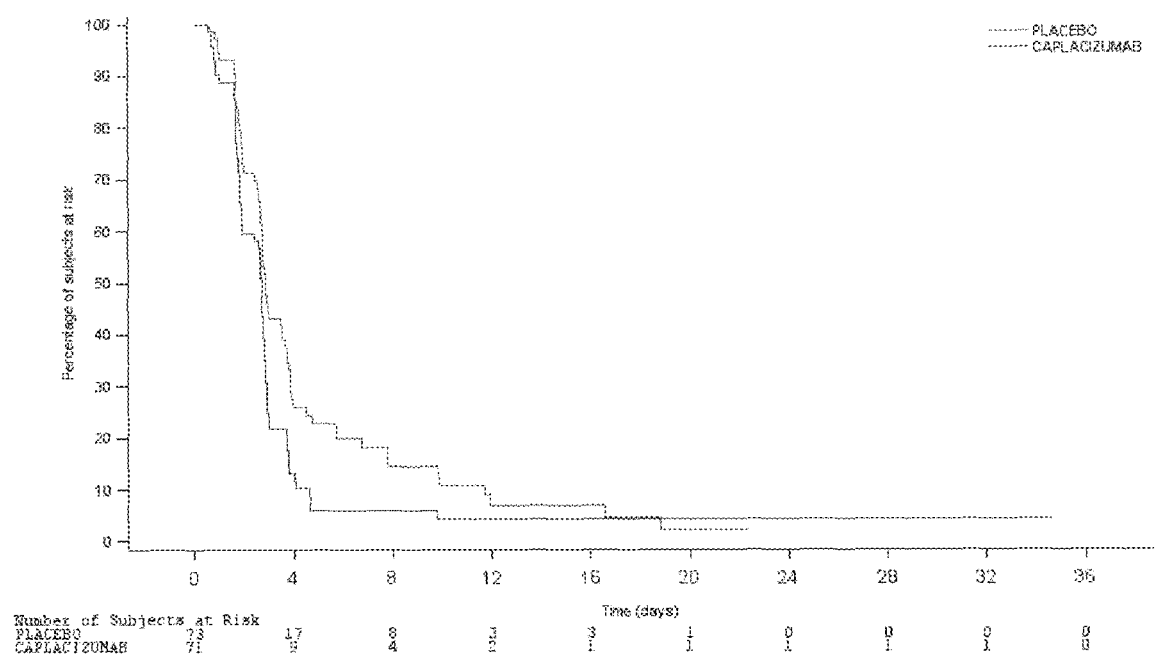
Figure 1. Time to Confirmed Normalization of Platelet Count in the Intention-to-Treat Population Figure 2. ADAMTS13 Activity According to Recurrences
A.
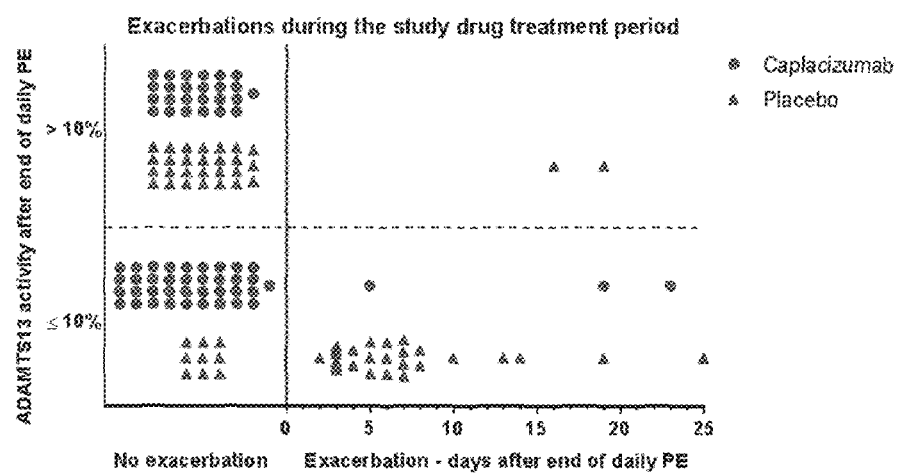
B.
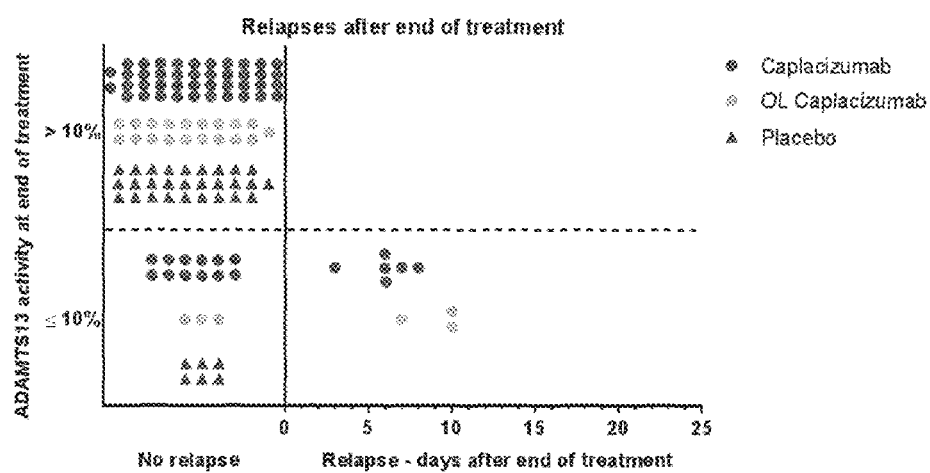

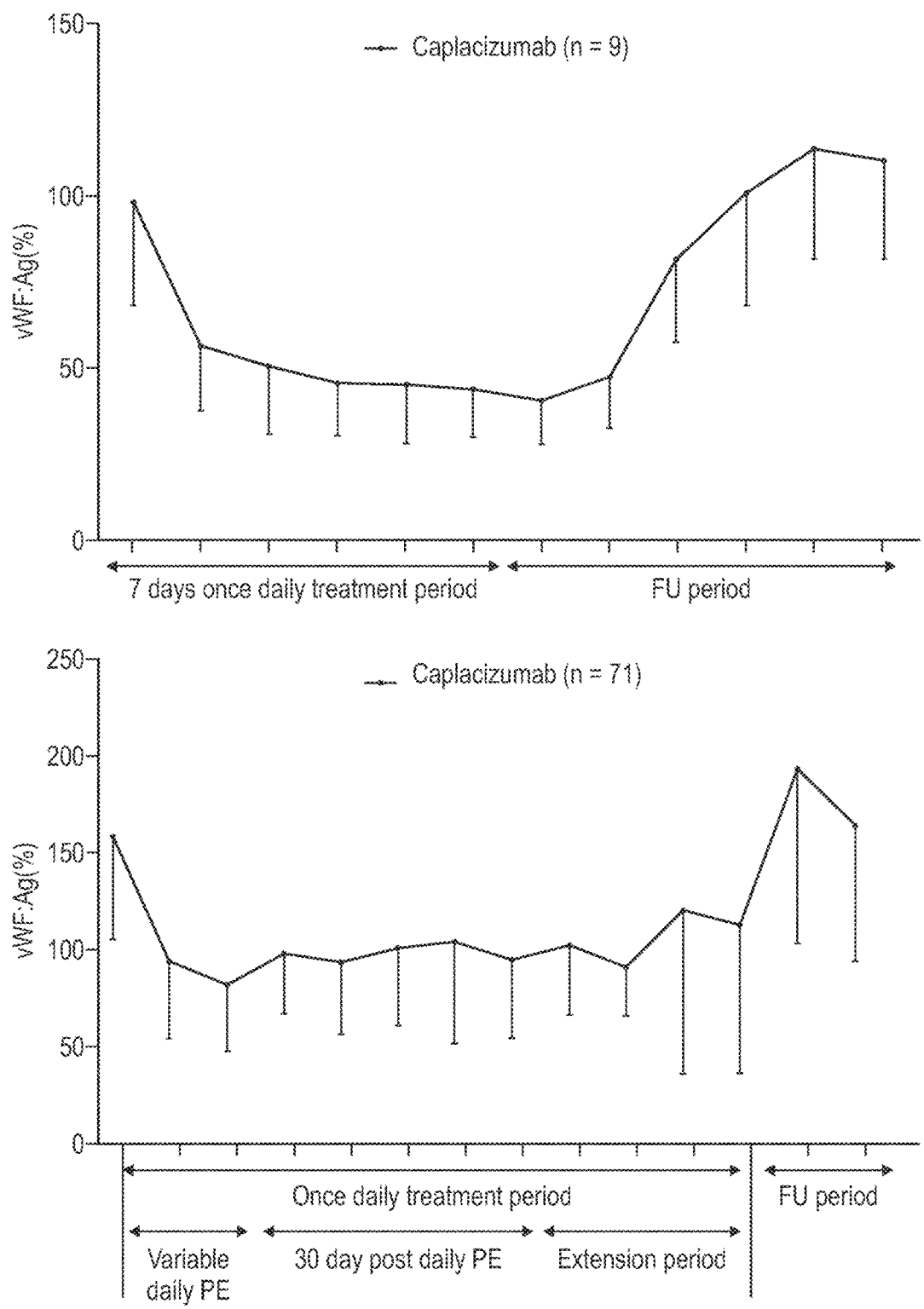

Figure 3  Mean vWF:Ag levels vs time profiles during a 7 days repeated subcutaneous 10 mg daily dosing of caplacizumab in healthy volunteers (upper panel), and during repeated subcutaneous daily administration of 10 mg caplacizumab in aTTP patients (lower panel). aTTP: acquired thrombotic thrombocytopenic purpura; PE: plasma exchange; FU: follow-up; vWF: von Willebrand factor.

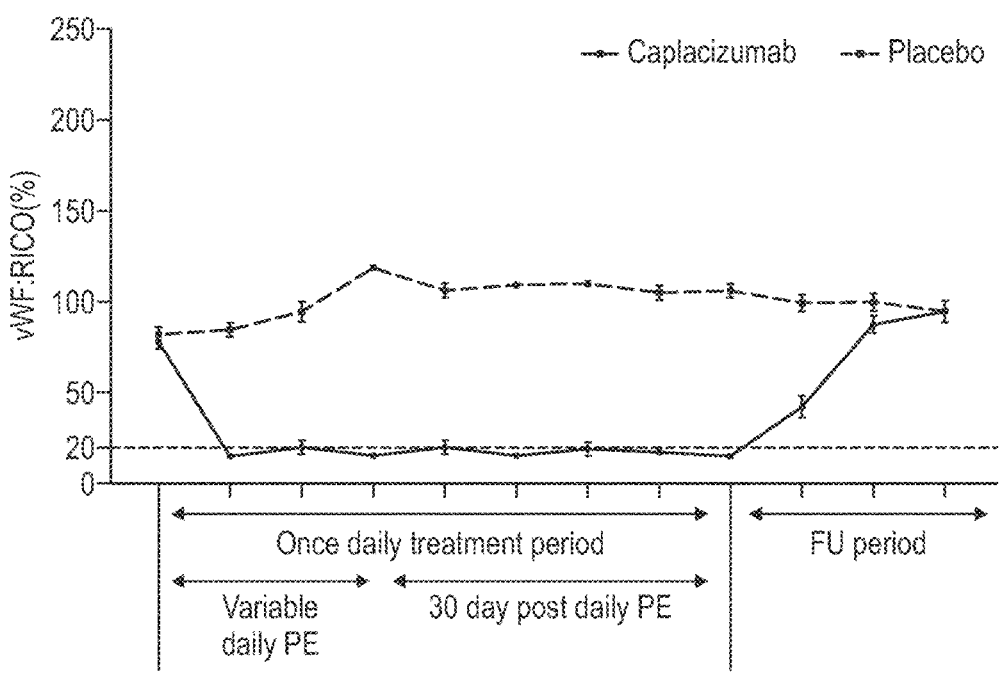
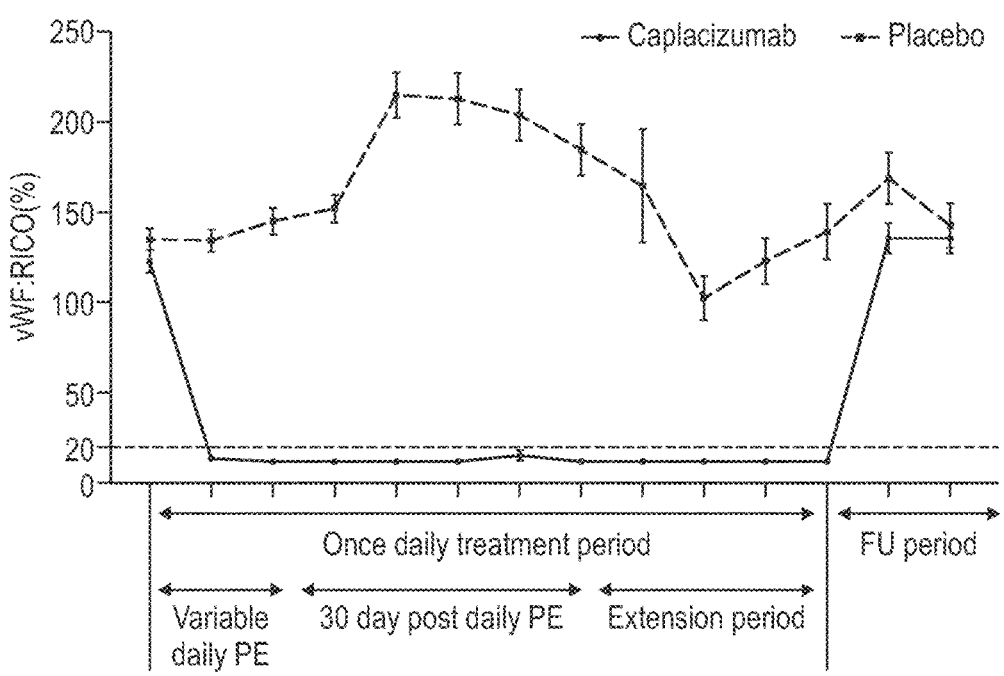

Figure 4  Mean (± SD) RICO activity in the phase II ALX-0681-2.1/10 ("TITAN", upper panel) and the phase III ALX0681-C301 ("HERCULES", lower panel), RICO values of <20% represent the threshold for pharmacological activity of caplacizumab; for the purpose of the graph, values below the lower limit of quantification of 15% were set at 15%, values above the upper limit of quantification of 120% were set at 120%. Graphs show mean ± standard error of the mean. PE: plasma exchange; FU: follow-up; RICO: ristocetin cofactor; SD: standard deviation; vWF: von Willebrand factor.

Figure 5
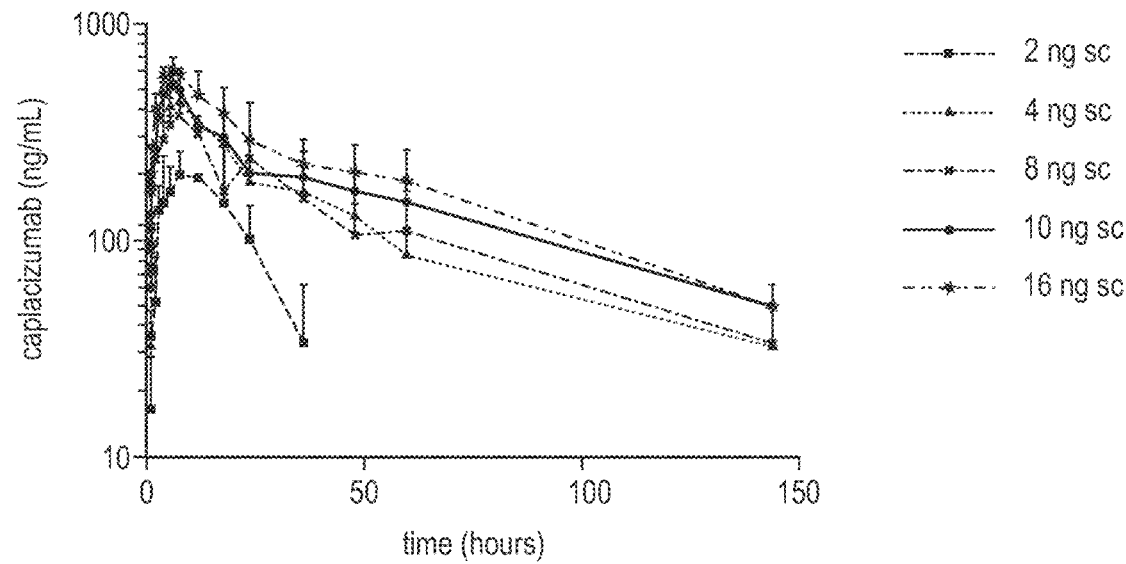
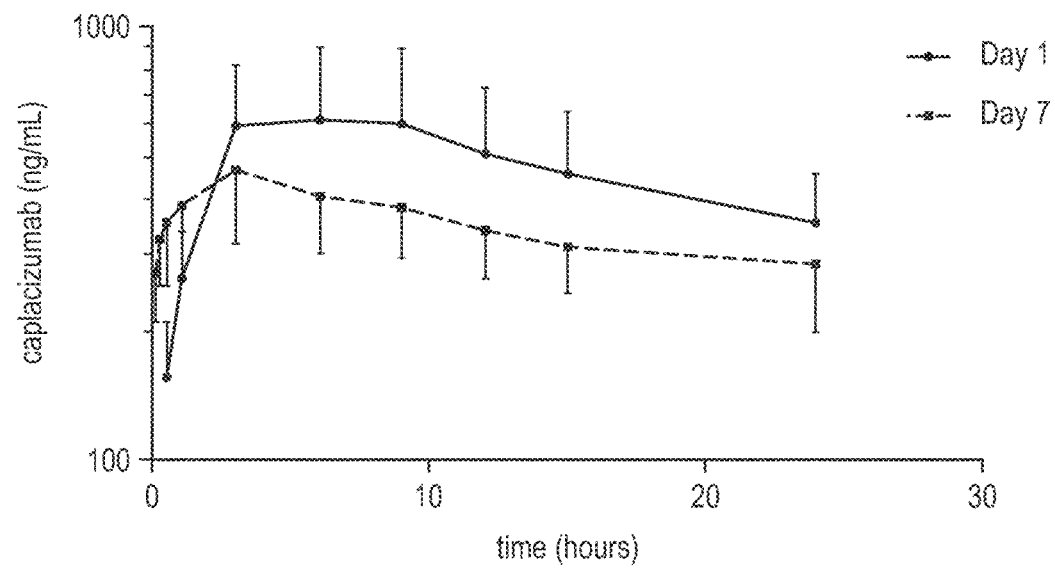

SEQUENCE LISTING

<160> NUMBER OF SEQ ID NOS: 24

<210> SEQ ID NO 1
<211> LENGTH: 259
<212> TYPE: PRT
<213> ORGANISM: Artificial Sequence
<220> FEATURE:
<223> OTHER INFORMATION: Nanobody Sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 2
<211> LENGTH: 259
<212> TYPE: PRT
<213> ORGANISM: Artificial Sequence
<220> FEATURE:
<223> OTHER INFORMATION: Nanobody Sequence

<400> SEQUENCE: 2

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Ser Thr Tyr Tyr Pro Asp Ser Val
50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Ala Gly Gly Ala Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Glu Arg
                165                 170                 175

Asp Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
            195                 200                 205

Met Val Tyr Leu Gln Met Asn Asn Leu Lys Pro Glu Asp Thr Ala Val
210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 3
<211> LENGTH: 265
<212> TYPE: PRT
<213> ORGANISM: Artificial Sequence
<220> FEATURE:
<223> OTHER INFORMATION: Nanobody Sequence

<400> SEQUENCE: 3

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Ser Glu Val Gln Leu Val Glu Ser
            130                 135                 140

Gly Gly Gly Leu Val Gln Ala Gly Gly Ala Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Glu Arg Asp Leu Val Ala Ala Ile Ser Arg Thr Gly
            180                 185                 190

Gly Ser Thr Tyr Tyr Pro Asp Ser Val Glu Gly Arg Phe Thr Ile Ser
            195                 200                 205

Arg Asp Asn Ala Lys Arg Met Val Tyr Leu Gln Met Asn Asn Leu Lys
210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
            245                 250                 255

Gln Gly Thr Gln Val Thr Val Ser Ser
            260                 265

<210> SEQ ID NO 4
<211> LENGTH: 286
<212> TYPE: PRT
<213> ORGANISM: Artificial Sequence
<220> FEATURE:
<223> OTHER INFORMATION: Nanobody Sequence

<400> SEQUENCE: 4

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Gly Ser Glu Val
145                 150                 155                 160

Gln Leu Val Glu Ser Gly Gly Gly Leu Val Gln Ala Gly Gly Ala Leu
            165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Glu Arg Asp Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Met Val Tyr Leu Gln
225                 230                 235                 240

Met Asn Asn Leu Lys Pro Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
        275                 280                 285

<210> SEQ ID NO 5
<211> LENGTH: 247
<212> TYPE: PRT
<213> ORGANISM: Artificial Sequence
<220> FEATURE:
<223> OTHER INFORMATION: Nanobody Sequence

<400> SEQUENCE: 5

```
Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
        35                  40                  45

Ala Thr Ile Thr Ser Gly Gly Ser Thr Asn Tyr Ala Asp Pro Val Lys
    50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Ala Ala Ala Glu Val Gln
        115                 120                 125

Leu Val Glu Ser Gly Gly Gly Leu Val Gln Pro Gly Gly Ser Leu Arg
    130                 135                 140

Leu Ser Cys Leu Ala Ser Gly Arg Ile Phe Ser Ile Gly Ala Met Gly
145                 150                 155                 160

Met Tyr Arg Gln Ala Pro Gly Lys Gln Arg Glu Leu Val Ala Thr Ile
                165                 170                 175

Thr Ser Gly Gly Ser Thr Asn Tyr Ala Asp Pro Val Lys Gly Arg Phe
            180                 185                 190

Thr Ile Ser Arg Asp Gly Pro Lys Asn Thr Val Tyr Leu Gln Met Asn
        195                 200                 205

Ser Leu Lys Pro Glu Asp Thr Ala Val Tyr Tyr Cys Tyr Ala Asn Leu
    210                 215                 220

Lys Gln Gly Ser Tyr Gly Tyr Arg Phe Asn Asp Tyr Trp Gly Gln Gly
225                 230                 235                 240

Thr Gln Val Thr Val Ser Ser
                245
```

<210> SEQ ID NO 6
<211> LENGTH: 253
<212> TYPE: PRT
<213> ORGANISM: Artificial Sequence
<220> FEATURE:
<223> OTHER INFORMATION: Nanobody Sequence

<400> SEQUENCE: 6

```
Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
        35                  40                  45

Ala Thr Ile Thr Ser Gly Gly Ser Thr Asn Tyr Ala Asp Pro Val Lys
    50                  55                  60
```

```
Gly Arg Phe Thr Ile Ser Arg Asp Gly Pro Lys Asn Thr Val Tyr Leu
 65                  70                  75                  80

Gln Met Asn Ser Leu Lys Pro Glu Asp Thr Ala Val Tyr Tyr Cys Tyr
                 85                  90                  95

Ala Asn Leu Lys Gln Gly Ser Tyr Gly Tyr Arg Phe Asn Asp Tyr Trp
             100                 105                 110

Gly Gln Gly Thr Gln Val Thr Val Ser Ser Gly Gly Gly Gly Ser Gly
         115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Leu Ala Ser Gly Arg Ile Phe
145                 150                 155                 160

Ser Ile Gly Ala Met Gly Met Tyr Arg Gln Ala Pro Gly Lys Gln Arg
                 165                 170                 175

Glu Leu Val Ala Thr Ile Thr Ser Gly Gly Ser Thr Asn Tyr Ala Asp
             180                 185                 190

Pro Val Lys Gly Arg Phe Thr Ile Ser Arg Asp Gly Pro Lys Asn Thr
         195                 200                 205

Val Tyr Leu Gln Met Asn Ser Leu Lys Pro Glu Asp Thr Ala Val Tyr
210                 215                 220

Tyr Cys Tyr Ala Asn Leu Lys Gln Gly Ser Tyr Gly Tyr Arg Phe Asn
225                 230                 235                 240

Asp Tyr Trp Gly Gln Gly Thr Gln Val Thr Val Ser Ser
                 245                 250

<210> SEQ ID NO 7
<211> LENGTH: 274
<212> TYPE: PRT
<213> ORGANISM: Artificial Sequence
<220> FEATURE:
<223> OTHER INFORMATION: Nanobody Sequence

<400> SEQUENCE: 7

Ala Val Gln Leu Val Glu Ser Gly Gly Gly Leu Val Gln Pro Gly Gly
 1               5                  10                  15

Ser Leu Arg Leu Ser Cys Leu Ala Ser Gly Arg Ile Phe Ser Ile Gly
             20                  25                  30

Ala Met Gly Met Tyr Arg Gln Ala Pro Gly Lys Gln Arg Glu Leu Val
         35                  40                  45

Ala Thr Ile Thr Ser Gly Gly Ser Thr Asn Tyr Ala Asp Pro Val Lys
     50                  55                  60

Gly Arg Phe Thr Ile Ser Arg Asp Gly Pro Lys Asn Thr Val Tyr Leu
 65                  70                  75                  80

Gln Met Asn Ser Leu Lys Pro Glu Asp Thr Ala Val Tyr Tyr Cys Tyr
                 85                  90                  95

Ala Asn Leu Lys Gln Gly Ser Tyr Gly Tyr Arg Phe Asn Asp Tyr Trp
             100                 105                 110

Gly Gln Gly Thr Gln Val Thr Val Ser Ser Gly Gly Gly Gly Ser Gly
         115                 120                 125

Gly Gly Ser Gly Gly Gly Gly Ser Gly Gly Gly Gly Ser Gly Gly Gly
130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Leu Ala
                 165                 170                 175
```

```
Ser Gly Arg Ile Phe Ser Ile Gly Ala Met Gly Met Tyr Arg Gln Ala
            180                 185                 190

Pro Gly Lys Gln Arg Glu Leu Val Ala Thr Ile Thr Ser Gly Gly Ser
            195                 200                 205

Thr Asn Tyr Ala Asp Pro Val Lys Gly Arg Phe Thr Ile Ser Arg Asp
            210                 215                 220

Gly Pro Lys Asn Thr Val Tyr Leu Gln Met Asn Ser Leu Lys Pro Glu
225                 230                 235                 240

Asp Thr Ala Val Tyr Tyr Cys Tyr Ala Asn Leu Lys Gln Gly Ser Tyr
                245                 250                 255

Gly Tyr Arg Phe Asn Asp Tyr Trp Gly Gln Gly Thr Gln Val Thr Val
            260                 265                 270

Ser Ser

<210> SEQ ID NO 8
<211> LENGTH: 259
<212> TYPE: PRT
<213> ORGANISM: Artificial Sequence
<220> FEATURE:
<223> OTHER INFORMATION: Nanobody Sequence

<400> SEQUENCE: 8

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
            35                  40                  45

Ala Ala Ile Ser Arg Thr Gly Gly Ser Thr Tyr Tyr Ala Arg Ser Val
        50                  55                  60

Glu Gly Arg Phe Thr Ile Ser Arg Asp Asn Ala Lys Arg Met Val Tyr
65                  70                  75                  80

Leu Gln Met Asn Ala Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Ala Gly Gly Ala Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Glu Arg
                165                 170                 175

Asp Val Val Ala Ala Ile Ser Arg Thr Gly Gly Ser Thr Tyr Tyr Ala
            180                 185                 190

Arg Ser Val Glu Gly Arg Phe Thr Ile Ser Arg Asp Asn Ala Lys Arg
            195                 200                 205

Met Val Tyr Leu Gln Met Asn Ala Leu Lys Pro Glu Asp Thr Ala Val
            210                 215                 220

Tyr Tyr Cys Ala Ala Ala Gly Val Arg Ala Glu Asp Gly Arg Val Arg
225                 230                 235                 240

Thr Leu Pro Ser Glu Tyr Asn Phe Trp Gly Gln Gly Thr Gln Val Thr
                245                 250                 255
```

Val Ser Ser

<210> SEQ ID NO 9
<211> LENGTH: 265
<212> TYPE: PRT
<213> ORGANISM: Artificial Sequence
<220> FEATURE:
<223> OTHER INFORMATION: Nanobody Sequence

<400> SEQUENCE: 9

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ala Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Gly Gly Gly Gly Ser Gly Gly Ser Glu Val Gln Leu Val Glu Ser
    130                 135                 140

Gly Gly Gly Leu Val Gln Ala Gly Gly Ala Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Glu Arg Asp Val Val Ala Ala Ile Ser Arg Thr Gly
            180                 185                 190

Gly Ser Thr Tyr Tyr Ala Arg Ser Val Glu Gly Arg Phe Thr Ile Ser
        195                 200                 205

Arg Asp Asn Ala Lys Arg Met Val Tyr Leu Gln Met Asn Ala Leu Lys
    210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Asn Phe Trp Gly
                245                 250                 255

Gln Gly Thr Gln Val Thr Val Ser Ser
            260                 265

<210> SEQ ID NO 10
<211> LENGTH: 286
<212> TYPE: PRT
<213> ORGANISM: Artificial Sequence
<220> FEATURE:
<223> OTHER INFORMATION: Nanobody Sequence

<400> SEQUENCE: 10

Gln Val Gln Leu Val Glu Ser Gly Gly Gly Leu Val Gln Ala Gly Gly
1               5                   10                  15

Ala Leu Arg Leu Ser Cys Ala Ser Gly Arg Thr Phe Ser Tyr Asn
            20                  25                  30

Pro Met Gly Trp Phe Arg Gln Ala Pro Gly Lys Glu Arg Asp Val Val
        35                  40                  45

Ala Ala Ile Ser Arg Thr Gly Gly Ser Thr Tyr Tyr Ala Arg Ser Val
 50                  55                  60

Glu Gly Arg Phe Thr Ile Ser Arg Asp Asn Ala Lys Arg Met Val Tyr
 65                  70                  75                  80

Leu Gln Met Asn Ala Leu Lys Pro Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

Ser Glu Tyr Asn Phe Trp Gly Gln Gly Thr Gln Val Thr Val Ser Ser
                115                 120                 125

Gly Gly Gly Gly Ser Gly Gly Gly Ser Gly Gly Gly Gly Ser Gly
        130                 135                 140

Gly Gly Gly Ser Gly Gly Gly Ser Gly Gly Gly Ser Glu Val
 145                 150                 155                 160

Gln Leu Val Glu Ser Gly Gly Leu Val Gln Ala Gly Gly Ala Leu
                165                 170                 175

Arg Leu Ser Cys Ala Ala Ser Gly Arg Thr Phe Ser Tyr Asn Pro Met
                180                 185                 190

Gly Trp Phe Arg Gln Ala Pro Gly Lys Glu Arg Asp Val Val Ala Ala
        195                 200                 205

Ile Ser Arg Thr Gly Gly Ser Thr Tyr Tyr Ala Arg Ser Val Glu Gly
        210                 215                 220

Arg Phe Thr Ile Ser Arg Asp Asn Ala Lys Arg Met Val Tyr Leu Gln
225                 230                 235                 240

Met Asn Ala Leu Lys Pro Glu Asp Thr Ala Val Tyr Tyr Cys Ala Ala
                245                 250                 255

Ala Gly Val Arg Ala Glu Asp Gly Arg Val Arg Thr Leu Pro Ser Glu
                260                 265                 270

Tyr Asn Phe Trp Gly Gln Gly Thr Gln Val Thr Val Ser Ser
                275                 280                 285

<210> SEQ ID NO 11
<211> LENGTH: 259
<212> TYPE: PRT
<213> ORGANISM: Artificial Sequence
<220> FEATURE:
<223> OTHER INFORMATION: Nanobody Sequence

<400> SEQUENCE: 11

Glu Val Gln Leu Val Glu Ser Gly Gly Gly Leu Val Gln Pro Gly Gly
 1               5                   10                  15

Ser Leu Arg Leu Ser Cys Ala Ala Ser Gly Arg Thr Phe Ser Tyr Asn
                20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Ser Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

-continued

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
            195                 200                 205

Ser Val Tyr Leu Gln Met Asn Ser Leu Arg Ala Glu Asp Thr Ala Val
        210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 12
<211> LENGTH: 259
<212> TYPE: PRT
<213> ORGANISM: Artificial Sequence
<220> FEATURE:
<223> OTHER INFORMATION: Nanobody Sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
        35                  40                  45

Ala Ala Ile Ser Arg Thr Gly Gly Ser Thr Tyr Tyr Ala Arg Ser Val
50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Val Val Ala Ala Ile Ser Arg Thr Gly Gly Ser Thr Tyr Tyr Ala
            180                 185                 190

Arg Ser Val Glu Gly Arg Phe Thr Ile Ser Arg Asp Asn Ala Lys Arg
            195                 200                 205

Met Val Tyr Leu Gln Met Asn Ser Leu Arg Ala Glu Asp Thr Ala Val

Tyr Tyr Cys Ala Ala Ala Gly Val Arg Ala Glu Asp Gly Arg Val Arg
225                 230                 235                 240

Thr Leu Pro Ser Glu Tyr Asn Phe Trp Gly Gln Gly Thr Gln Val Thr
                245                 250                 255

Val Ser Ser

<210> SEQ ID NO 13
<211> LENGTH: 265
<212> TYPE: PRT
<213> ORGANISM: Artificial Sequence
<220> FEATURE:
<223> OTHER INFORMATION: Nanobody Sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Leu Val Ala Ala Ile Ser Arg Thr Gly
            180                 185                 190

Gly Ser Thr Tyr Tyr Pro Asp Ser Val Glu Gly Arg Phe Thr Ile Ser
        195                 200                 205

Arg Asp Asn Ala Lys Arg Met Val Tyr Leu Gln Met Asn Ser Leu Arg
    210                 215                 220

Ala Glu Asp Thr Ala Val Tyr Tyr Cys Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
            260                 265

<210> SEQ ID NO 14
<211> LENGTH: 265
<212> TYPE: PRT
<213> ORGANISM: Artificial Sequence
<220> FEATURE:
<223> OTHER INFORMATION: Nanobody Sequence

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Leu Val Ala Ala Ile Ser Arg Thr Gly
            180                 185                 190

Gly Ser Thr Tyr Tyr Pro Asp Ser Val Glu Gly Arg Phe Thr Ile Ser
        195                 200                 205

Arg Asp Asn Ala Lys Arg Ser Val Tyr Leu Gln Met Asn Ser Leu Arg
    210                 215                 220

Ala Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
            260                 265

<210> SEQ ID NO 15
<211> LENGTH: 265
<212> TYPE: PRT
<213> ORGANISM: Artificial Sequence
<220> FEATURE:
<223> OTHER INFORMATION: Nanobody Sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys

```
                    85                  90                  95
Ala Ala Ala Gly Val Arg Ala Glu Asp Gly Arg Val Arg Thr Leu Pro
                100                 105                 110

Ser Glu Tyr Asn Phe Trp Gly Gln Gly Thr Gln Val Thr Val Ser Ser
                115                 120                 125

Gly Gly Gly Gly Ser Gly Gly Ser Glu Val Gln Leu Val Glu Ser
            130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Val Val Ala Ala Ile Ser Arg Thr Gly
                180                 185                 190

Gly Ser Thr Tyr Tyr Ala Arg Ser Val Glu Gly Arg Phe Thr Ile Ser
                195                 200                 205

Arg Asp Asn Ala Lys Arg Met Val Tyr Leu Gln Met Asn Ser Leu Arg
                210                 215                 220

Ala Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Asn Phe Trp Gly
                245                 250                 255

Gln Gly Thr Gln Val Thr Val Ser Ser
                260                 265

<210> SEQ ID NO 16
<211> LENGTH: 286
<212> TYPE: PRT
<213> ORGANISM: Artificial Sequence
<220> FEATURE:
<223> OTHER INFORMATION: Nanobody Sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
                20                  25                  30

Pro Met Gly Trp Phe Arg Gln Ala Pro Gly Lys Gly Arg Glu Leu Val
                35                  40                  45

Ala Ala Ile Ser Arg Thr Gly Gly Ser Thr Tyr Tyr Pro Asp Ser Val
                50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
                100                 105                 110

Ser Glu Tyr Thr Phe Trp Gly Gln Gly Thr Gln Val Thr Val Ser Ser
                115                 120                 125

Gly Gly Gly Gly Ser Gly Gly Gly Ser Gly Gly Gly Ser Gly
            130                 135                 140

Gly Gly Ser Gly Gly Gly Ser Gly Gly Gly Ser Glu Val
145                 150                 155                 160

Gln Leu Val Glu Ser Gly Gly Gly Leu Val Gln Pro Gly Gly Ser Leu
                165                 170                 175

Arg Leu Ser Cys Ala Ala Ser Gly Arg Thr Phe Ser Tyr Asn Pro Met
```

```
            180                 185                 190
Gly Trp Phe Arg Gln Ala Pro Gly Lys Gly Arg Glu Leu Val Ala Ala
                195                 200                 205
Ile Ser Arg Thr Gly Gly Ser Thr Tyr Tyr Pro Asp Ser Val Glu Gly
            210                 215                 220
Arg Phe Thr Ile Ser Arg Asp Asn Ala Lys Arg Met Val Tyr Leu Gln
225                 230                 235                 240
Met Asn Ser Leu Arg Ala Glu Asp Thr Ala Val Tyr Tyr Cys Ala Ala
                245                 250                 255
Ala Gly Val Arg Ala Glu Asp Gly Arg Val Arg Thr Leu Pro Ser Glu
            260                 265                 270
Tyr Thr Phe Trp Gly Gln Gly Thr Gln Val Thr Val Ser Ser
            275                 280                 285

<210> SEQ ID NO 17
<211> LENGTH: 286
<212> TYPE: PRT
<213> ORGANISM: Artificial Sequence
<220> FEATURE:
<223> OTHER INFORMATION: Nanobody Sequence

<400> SEQUENCE: 17

Glu Val Gln Leu Val Glu Ser Gly Gly Gly Leu Val Gln Pro Gly Gly
1               5                   10                  15
Ser Leu Arg Leu Ser Cys Ala Ala Ser Gly Arg Thr Phe Ser Tyr Asn
            20                  25                  30
Pro Met Gly Trp Phe Arg Gln Ala Pro Gly Lys Gly Arg Glu Leu Val
        35                  40                  45
Ala Ala Ile Ser Arg Thr Gly Gly Ser Thr Tyr Tyr Pro Asp Ser Val
    50                  55                  60
Glu Gly Arg Phe Thr Ile Ser Arg Asp Asn Ala Lys Arg Ser Val Tyr
65                  70                  75                  80
Leu Gln Met Asn Ser Leu Arg Ala Glu Asp Thr Ala Val Tyr Tyr Cys
                85                  90                  95
Ala Ala Ala Gly Val Arg Ala Glu Asp Gly Arg Val Arg Thr Leu Pro
            100                 105                 110
Ser Glu Tyr Thr Phe Trp Gly Gln Gly Thr Gln Val Thr Val Ser Ser
        115                 120                 125
Gly Gly Gly Gly Ser Gly Gly Gly Ser Gly Gly Gly Gly Ser Gly
        130                 135                 140
Gly Gly Gly Ser Gly Gly Gly Ser Gly Gly Gly Gly Ser Glu Val
145                 150                 155                 160
Gln Leu Val Glu Ser Gly Gly Gly Leu Val Gln Pro Gly Gly Ser Leu
                165                 170                 175
Arg Leu Ser Cys Ala Ala Ser Gly Arg Thr Phe Ser Tyr Asn Pro Met
            180                 185                 190
Gly Trp Phe Arg Gln Ala Pro Gly Lys Gly Arg Glu Leu Val Ala Ala
                195                 200                 205
Ile Ser Arg Thr Gly Gly Ser Thr Tyr Tyr Pro Asp Ser Val Glu Gly
            210                 215                 220
Arg Phe Thr Ile Ser Arg Asp Asn Ala Lys Arg Ser Val Tyr Leu Gln
225                 230                 235                 240
Met Asn Ser Leu Arg Ala Glu Asp Thr Ala Val Tyr Tyr Cys Ala Ala
                245                 250                 255
Ala Gly Val Arg Ala Glu Asp Gly Arg Val Arg Thr Leu Pro Ser Glu
```

```
                    260                 265                 270
Tyr Thr Phe Trp Gly Gln Gly Thr Gln Val Thr Val Ser Ser
                275                 280                 285

<210> SEQ ID NO 18
<211> LENGTH: 286
<212> TYPE: PRT
<213> ORGANISM: Artificial Sequence
<220> FEATURE:
<223> OTHER INFORMATION: Nanobody Sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Gly Ser Glu Val
145                 150                 155                 160

Gln Leu Val Glu Ser Gly Gly Gly Leu Val Gln Pro Gly Gly Ser Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Gly Arg Glu Val Val Ala Ala
        195                 200                 205

Ile Ser Arg Thr Gly Gly Ser Thr Tyr Tyr Ala Arg Ser Val Glu Gly
    210                 215                 220

Arg Phe Thr Ile Ser Arg Asp Asn Ala Lys Arg Met Val Tyr Leu Gln
225                 230                 235                 240

Met Asn Ser Leu Arg Ala Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Asn Phe Trp Gly Gln Gly Thr Gln Val Thr Val Ser Ser
        275                 280                 285

<210> SEQ ID NO 19
<211> LENGTH: 128
<212> TYPE: PRT
<213> ORGANISM: Artificial Sequence
<220> FEATURE:
<223> OTHER INFORMATION: Nanobody Sequence

<400> SEQUENCE: 19
```

Glu Val Gln Leu Val Glu Ser Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
            35                  40                  45

Ala Ala Ile Ser Arg Thr Gly Gly Ser Thr Tyr Tyr Pro Asp Ser Val
50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
            85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

<210> SEQ ID NO 20
<211> LENGTH: 2804
<212> TYPE: PRT
<213> ORGANISM: Homo sapiens

<400> SEQUENCE: 20

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
            85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Phe Met Thr Gln
            165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
            210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

```
Cys Ala Gly Gly Leu Glu Cys Ala Cys Pro Ala Leu Leu Glu Tyr Ala
            260                 265                 270
Arg Thr Cys Ala Gln Glu Gly Met Val Leu Tyr Gly Trp Thr Asp His
            275                 280                 285
Ser Ala Cys Ser Pro Val Cys Pro Ala Gly Met Glu Tyr Arg Gln Cys
            290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Cys Pro Cys Val His
            340                 345                 350
Ser Gly Lys Arg Tyr Pro Pro Gly Thr Ser Leu Ser Arg Asp Cys Asn
            355                 360                 365
Thr Cys Ile Cys Arg Asn Ser Gln Trp Ile Cys Ser Asn Glu Glu Cys
370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
                420                 425                 430
Ala Asp Asp Arg Asp Ala Val Cys Thr Arg Ser Val Thr Val Arg Leu
                435                 440                 445
Pro Gly Leu His Asn Ser Leu Val Lys Leu Lys His Gly Ala Gly Val
            450                 455                 460
Ala Met Asp Gly Gln Asp Ile Gln Leu Pro Leu Leu Lys Gly Asp Leu
465                 470                 475                 480
Arg Ile Gln His Thr Val Thr Ala Ser Val Arg Leu Ser Tyr Gly Glu
                485                 490                 495
Asp Leu Gln Met Asp Trp Asp Gly Arg Gly Arg Leu Leu Val Lys Leu
            500                 505                 510
Ser Pro Val Tyr Ala Gly Lys Thr Cys Gly Leu Cys Gly Asn Tyr Asn
            515                 520                 525
Gly Asn Gln Gly Asp Asp Phe Leu Thr Pro Ser Gly Leu Ala Glu Pro
530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
                565                 570                 575
Thr Arg Phe Ser Glu Glu Ala Cys Ala Val Leu Thr Ser Pro Thr Phe
            580                 585                 590
Glu Ala Cys His Arg Ala Val Ser Pro Leu Pro Tyr Leu Arg Asn Cys
            595                 600                 605
Arg Tyr Asp Val Cys Ser Cys Ser Asp Gly Arg Glu Cys Leu Cys Gly
            610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
                645                 650                 655
Val Tyr Leu Gln Cys Gly Thr Pro Cys Asn Leu Thr Cys Arg Ser Leu
            660                 665                 670
```

```
Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
        915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn Asp Leu Thr
        995                 1000                1005

Ser Ser Asn Leu Gln Val Glu  Glu Asp Pro Val Asp  Phe Gly Asn
    1010                1015                1020

Ser Trp Lys Val Ser Ser Gln  Cys Ala Asp Thr Arg  Lys Val Pro
    1025                1030                1035

Leu Asp Ser Ser Pro Ala Thr  Cys His Asn Asn Ile  Met Lys Gln
    1040                1045                1050

Thr Met Val Asp Ser Ser Cys  Arg Ile Leu Thr Ser  Asp Val Phe
    1055                1060                1065

Gln Asp Cys Asn Lys Leu Val  Asp Pro Glu Pro Tyr  Leu Asp Val
    1070                1075                1080

Cys Ile Tyr Asp Thr Cys Ser  Cys Glu Ser Ile Gly  Asp Cys Ala
```

```
                    1085                1090                1095
Cys Phe Cys Asp Thr Ile Ala Ala Tyr Ala His Val Cys Ala Gln
            1100                1105                1110
His Gly Lys Val Val Thr Trp Arg Thr Ala Thr Leu Cys Pro Gln
            1115                1120                1125
Ser Cys Glu Glu Arg Asn Leu Arg Glu Asn Gly Tyr Glu Cys Glu
            1130                1135                1140
Trp Arg Tyr Asn Ser Cys Ala Pro Ala Cys Gln Val Thr Cys Gln
            1145                1150                1155
His Pro Glu Pro Leu Ala Cys Pro Val Gln Cys Val Glu Gly Cys
            1160                1165                1170
His Ala His Cys Pro Pro Gly Lys Ile Leu Asp Glu Leu Leu Gln
            1175                1180                1185
Thr Cys Val Asp Pro Glu Asp Cys Pro Val Cys Glu Val Ala Gly
            1190                1195                1200
Arg Arg Phe Ala Ser Gly Lys Lys Val Thr Leu Asn Pro Ser Asp
            1205                1210                1215
Pro Glu His Cys Gln Ile Cys His Cys Asp Val Val Asn Leu Thr
            1220                1225                1230
Cys Glu Ala Cys Gln Glu Pro Gly Gly Leu Val Val Pro Pro Thr
            1235                1240                1245
Asp Ala Pro Val Ser Pro Thr Thr Leu Tyr Val Glu Asp Ile Ser
            1250                1255                1260
Glu Pro Pro Leu His Asp Phe Tyr Cys Ser Arg Leu Leu Asp Leu
            1265                1270                1275
Val Phe Leu Leu Asp Gly Ser Ser Arg Leu Ser Glu Ala Glu Phe
            1280                1285                1290
Glu Val Leu Lys Ala Phe Val Val Asp Met Met Glu Arg Leu Arg
            1295                1300                1305
Ile Ser Gln Lys Trp Val Arg Val Ala Val Val Glu Tyr His Asp
            1310                1315                1320
Gly Ser His Ala Tyr Ile Gly Leu Lys Asp Arg Lys Arg Pro Ser
            1325                1330                1335
Glu Leu Arg Arg Ile Ala Ser Gln Val Lys Tyr Ala Gly Ser Gln
            1340                1345                1350
Val Ala Ser Thr Ser Glu Val Leu Lys Tyr Thr Leu Phe Gln Ile
            1355                1360                1365
Phe Ser Lys Ile Asp Arg Pro Glu Ala Ser Arg Ile Ala Leu Leu
            1370                1375                1380
Leu Met Ala Ser Gln Glu Pro Gln Arg Met Ser Arg Asn Phe Val
            1385                1390                1395
Arg Tyr Val Gln Gly Leu Lys Lys Lys Lys Val Ile Val Ile Pro
            1400                1405                1410
Val Gly Ile Gly Pro His Ala Asn Leu Lys Gln Ile Arg Leu Ile
            1415                1420                1425
Glu Lys Gln Ala Pro Glu Asn Lys Ala Phe Val Leu Ser Ser Val
            1430                1435                1440
Asp Glu Leu Glu Gln Gln Arg Asp Glu Ile Val Ser Tyr Leu Cys
            1445                1450                1455
Asp Leu Ala Pro Glu Ala Pro Pro Pro Thr Leu Pro Pro His Met
            1460                1465                1470
Ala Gln Val Thr Val Gly Pro Gly Leu Arg Asn Ser Met Val Leu
            1475                1480                1485
```

```
Asp Val Ala Phe Val Leu Glu Gly Ser Asp Lys Ile Gly Glu Ala
    1490            1495                1500

Asp Phe Asn Arg Ser Lys Glu Phe Met Glu Glu Val Ile Gln Arg
    1505            1510                1515

Met Asp Val Gly Gln Asp Ser Ile His Val Thr Val Leu Gln Tyr
    1520            1525                1530

Ser Tyr Met Val Thr Val Glu Tyr Pro Phe Ser Glu Ala Gln Ser
    1535            1540                1545

Lys Gly Asp Ile Leu Gln Arg Val Arg Glu Ile Arg Tyr Gln Gly
    1550            1555                1560

Gly Asn Arg Thr Asn Thr Gly Leu Ala Leu Arg Tyr Leu Ser Asp
    1565            1570                1575

His Ser Phe Leu Val Ser Gln Gly Asp Arg Glu Gln Ala Pro Asn
    1580            1585                1590

Leu Val Tyr Met Val Thr Gly Asn Pro Ala Ser Asp Glu Ile Lys
    1595            1600                1605

Arg Leu Pro Gly Asp Ile Gln Val Val Pro Ile Gly Val Gly Pro
    1610            1615                1620

Asn Ala Asn Val Gln Glu Leu Glu Arg Ile Gly Trp Pro Asn Ala
    1625            1630                1635

Pro Ile Leu Ile Gln Asp Phe Glu Thr Leu Pro Arg Glu Ala Pro
    1640            1645                1650

Asp Leu Val Leu Gln Arg Cys Cys Ser Gly Glu Gly Leu Gln Ile
    1655            1660                1665

Pro Thr Leu Ser Pro Ala Pro Asp Cys Ser Gln Pro Leu Asp Val
    1670            1675                1680

Ile Leu Leu Leu Asp Gly Ser Ser Ser Phe Pro Ala Ser Tyr Phe
    1685            1690                1695

Asp Glu Met Lys Ser Phe Ala Lys Ala Phe Ile Ser Lys Ala Asn
    1700            1705                1710

Ile Gly Pro Arg Leu Thr Gln Val Ser Val Leu Gln Tyr Gly Ser
    1715            1720                1725

Ile Thr Thr Ile Asp Val Pro Trp Asn Val Val Pro Glu Lys Ala
    1730            1735                1740

His Leu Leu Ser Leu Val Asp Val Met Gln Arg Glu Gly Gly Pro
    1745            1750                1755

Ser Gln Ile Gly Asp Ala Leu Gly Phe Ala Val Arg Tyr Leu Thr
    1760            1765                1770

Ser Glu Met His Gly Ala Arg Pro Gly Ala Ser Lys Ala Val Val
    1775            1780                1785

Ile Leu Val Thr Asp Val Ser Val Asp Ser Val Asp Ala Ala Ala
    1790            1795                1800

Asp Ala Ala Arg Ser Asn Arg Val Thr Val Phe Pro Ile Gly Ile
    1805            1810                1815

Gly Asp Arg Tyr Asp Ala Ala Gln Leu Arg Ile Leu Ala Gly Pro
    1820            1825                1830

Ala Gly Asp Ser Asn Val Val Lys Leu Gln Arg Ile Glu Asp Leu
    1835            1840                1845

Pro Thr Met Val Thr Leu Gly Asn Ser Phe Leu His Lys Leu Cys
    1850            1855                1860

Ser Gly Phe Val Arg Ile Cys Met Asp Glu Asp Gly Asn Glu Lys
    1865            1870                1875
```

```
Arg Pro Gly Asp Val Trp Thr Leu Pro Asp Gln Cys His Thr Val
    1880                1885                1890

Thr Cys Gln Pro Asp Gly Gln Thr Leu Leu Lys Ser His Arg Val
    1895                1900                1905

Asn Cys Asp Arg Gly Leu Arg Pro Ser Cys Pro Asn Ser Gln Ser
    1910                1915                1920

Pro Val Lys Val Glu Glu Thr Cys Gly Cys Arg Trp Thr Cys Pro
    1925                1930                1935

Cys Val Cys Thr Gly Ser Ser Thr Arg His Ile Val Thr Phe Asp
    1940                1945                1950

Gly Gln Asn Phe Lys Leu Thr Gly Ser Cys Ser Tyr Val Leu Phe
    1955                1960                1965

Gln Asn Lys Glu Gln Asp Leu Glu Val Ile Leu His Asn Gly Ala
    1970                1975                1980

Cys Ser Pro Gly Ala Arg Gln Gly Cys Met Lys Ser Ile Glu Val
    1985                1990                1995

Lys His Ser Ala Leu Ser Val Glu Leu His Ser Asp Met Glu Val
    2000                2005                2010

Thr Val Asn Gly Arg Leu Val Ser Val Pro Tyr Val Gly Gly Asn
    2015                2020                2025

Met Glu Val Asn Val Tyr Gly Ala Ile Met His Glu Val Arg Phe
    2030                2035                2040

Asn His Leu Gly His Ile Phe Thr Phe Thr Pro Gln Asn Asn Glu
    2045                2050                2055

Phe Gln Leu Gln Leu Ser Pro Lys Thr Phe Ala Ser Lys Thr Tyr
    2060                2065                2070

Gly Leu Cys Gly Ile Cys Asp Glu Asn Gly Ala Asn Asp Phe Met
    2075                2080                2085

Leu Arg Asp Gly Thr Val Thr Thr Asp Trp Lys Thr Leu Val Gln
    2090                2095                2100

Glu Trp Thr Val Gln Arg Pro Gly Gln Thr Cys Gln Pro Ile Leu
    2105                2110                2115

Glu Glu Gln Cys Leu Val Pro Asp Ser Ser His Cys Gln Val Leu
    2120                2125                2130

Leu Leu Pro Leu Phe Ala Glu Cys His Lys Val Leu Ala Pro Ala
    2135                2140                2145

Thr Phe Tyr Ala Ile Cys Gln Gln Asp Ser Cys His Gln Glu Gln
    2150                2155                2160

Val Cys Glu Val Ile Ala Ser Tyr Ala His Leu Cys Arg Thr Asn
    2165                2170                2175

Gly Val Cys Val Asp Trp Arg Thr Pro Asp Phe Cys Ala Met Ser
    2180                2185                2190

Cys Pro Pro Ser Leu Val Tyr Asn His Cys Glu His Gly Cys Pro
    2195                2200                2205

Arg His Cys Asp Gly Asn Val Ser Ser Cys Gly Asp His Pro Ser
    2210                2215                2220

Glu Gly Cys Phe Cys Pro Pro Asp Lys Val Met Leu Glu Gly Ser
    2225                2230                2235

Cys Val Pro Glu Glu Ala Cys Thr Gln Cys Ile Gly Glu Asp Gly
    2240                2245                2250

Val Gln His Gln Phe Leu Glu Ala Trp Val Pro Asp His Gln Pro
    2255                2260                2265

Cys Gln Ile Cys Thr Cys Leu Ser Gly Arg Lys Val Asn Cys Thr
```

```
              2270               2275               2280
Thr Gln Pro Cys Pro Thr Ala Lys Ala Pro Thr Cys Gly Leu Cys
    2285               2290               2295
Glu Val Ala Arg Leu Arg Gln Asn Ala Asp Gln Cys Cys Pro Glu
    2300               2305               2310
Tyr Glu Cys Val Cys Asp Pro Val Ser Cys Asp Leu Pro Pro Val
    2315               2320               2325
Pro His Cys Glu Arg Gly Leu Gln Pro Thr Leu Thr Asn Pro Gly
    2330               2335               2340
Glu Cys Arg Pro Asn Phe Thr Cys Ala Cys Arg Lys Glu Glu Cys
    2345               2350               2355
Lys Arg Val Ser Pro Pro Ser Cys Pro Pro His Arg Leu Pro Thr
    2360               2365               2370
Leu Arg Lys Thr Gln Cys Cys Asp Glu Tyr Glu Cys Ala Cys Asn
    2375               2380               2385
Cys Val Asn Ser Thr Val Ser Cys Pro Leu Gly Tyr Leu Ala Ser
    2390               2395               2400
Thr Ala Thr Asn Asp Cys Gly Cys Thr Thr Thr Cys Leu Pro
    2405               2410               2415
Asp Lys Val Cys Val His Arg Ser Thr Ile Tyr Pro Val Gly Gln
    2420               2425               2430
Phe Trp Glu Glu Gly Cys Asp Val Cys Thr Cys Thr Asp Met Glu
    2435               2440               2445
Asp Ala Val Met Gly Leu Arg Val Ala Gln Cys Ser Gln Lys Pro
    2450               2455               2460
Cys Glu Asp Ser Cys Arg Ser Gly Phe Thr Tyr Val Leu His Glu
    2465               2470               2475
Gly Glu Cys Cys Gly Arg Cys Leu Pro Ser Ala Cys Glu Val Val
    2480               2485               2490
Thr Gly Ser Pro Arg Gly Asp Ser Gln Ser Ser Trp Lys Ser Val
    2495               2500               2505
Gly Ser Gln Trp Ala Ser Pro Glu Asn Pro Cys Leu Ile Asn Glu
    2510               2515               2520
Cys Val Arg Val Lys Glu Glu Val Phe Ile Gln Gln Arg Asn Val
    2525               2530               2535
Ser Cys Pro Gln Leu Glu Val Pro Val Cys Pro Ser Gly Phe Gln
    2540               2545               2550
Leu Ser Cys Lys Thr Ser Ala Cys Cys Pro Ser Cys Arg Cys Glu
    2555               2560               2565
Arg Met Glu Ala Cys Met Leu Asn Gly Thr Val Ile Gly Pro Gly
    2570               2575               2580
Lys Thr Val Met Ile Asp Val Cys Thr Thr Cys Arg Cys Met Val
    2585               2590               2595
Gln Val Gly Val Ile Ser Gly Phe Lys Leu Glu Cys Arg Lys Thr
    2600               2605               2610
Thr Cys Asn Pro Cys Pro Leu Gly Tyr Lys Glu Glu Asn Asn Thr
    2615               2620               2625
Gly Glu Cys Cys Gly Arg Cys Leu Pro Thr Ala Cys Thr Ile Gln
    2630               2635               2640
Leu Arg Gly Gly Gln Ile Met Thr Leu Lys Arg Asp Glu Thr Leu
    2645               2650               2655
Gln Asp Gly Cys Asp Thr His Phe Cys Lys Val Asn Glu Arg Gly
    2660               2665               2670
```

```
Glu Tyr Phe Trp Glu Lys Arg Val Thr Gly Cys Pro Pro Phe Asp
    2675                2680                2685

Glu His Lys Cys Leu Ala Glu Gly Gly Lys Ile Met Lys Ile Pro
    2690                2695                2700

Gly Thr Cys Cys Asp Thr Cys Glu Glu Pro Glu Cys Asn Asp Ile
    2705                2710                2715

Thr Ala Arg Leu Gln Tyr Val Lys Val Gly Ser Cys Lys Ser Glu
    2720                2725                2730

Val Glu Val Asp Ile His Tyr Cys Gln Gly Lys Cys Ala Ser Lys
    2735                2740                2745

Ala Met Tyr Ser Ile Asp Ile Asn Asp Val Gln Asp Gln Cys Ser
    2750                2755                2760

Cys Cys Ser Pro Thr Arg Thr Glu Pro Met Gln Val Ala Leu His
    2765                2770                2775

Cys Thr Asn Gly Ser Val Val Tyr His Glu Val Leu Asn Ala Met
    2780                2785                2790

Glu Cys Lys Cys Ser Pro Arg Lys Cys Ser Lys
    2795                2800

<210> SEQ ID NO 21
<211> LENGTH: 5
<212> TYPE: PRT
<213> ORGANISM: Artificial Sequence
<220> FEATURE:
<223> OTHER INFORMATION: CDR1

<400> SEQUENCE: 21

Tyr Asn Pro Met Gly
1               5

<210> SEQ ID NO 22
<211> LENGTH: 17
<212> TYPE: PRT
<213> ORGANISM: Artificial Sequence
<220> FEATURE:
<223> OTHER INFORMATION: CDR2

<400> SEQUENCE: 22

Ala Ile Ser Arg Thr Gly Gly Ser Thr Tyr Tyr Pro Asp Ser Val Glu
1               5                   10                  15

Gly

<210> SEQ ID NO 23
<211> LENGTH: 19
<212> TYPE: PRT
<213> ORGANISM: Artificial Sequence
<220> FEATURE:
<223> OTHER INFORMATION: CDR3

<400> SEQUENCE: 23

Ala Gly Val Arg Ala Glu Asp Gly Arg Val Arg Thr Leu Pro Ser Glu
1               5                   10                  15

Tyr Thr Phe

<210> SEQ ID NO 24
<211> LENGTH: 260
<212> TYPE: PRT
<213> ORGANISM: Artificial Sequence
<220> FEATURE:
<223> OTHER INFORMATION: Nanobody Sequence
```

```
<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Ala
            260
```

METHODS OF TREATING INITIAL EPISODE OF TTP WITH IMMUNOGLOBULIN SINGLE VARIABLE DOMAINS

RELATED APPLICATIONS

This Application is a national stage filing under 35 U.S.C. 371 of International Patent Application Serial No. PCT/EP2019/052929, filed Feb. 6, 2019, which claims the benefit under 35 U.S.C. § 119(e) of U.S. Provisional Application Ser. No. 62/662,381, filed Apr. 25, 2018, and U.S. Provisional Application Ser. No. 62/627,082, filed Feb. 6, 2018. The entire contents of each of these applications are incorporated herein by reference in its entirety.

1. FIELD OF THE INVENTION

The present invention is based on the finding that administration of polypeptides comprising at least one immunoglobulin single variable domain (ISVD) against von Willebrand Factor (vWF) to human patients with a thrombotic thrombocytopenic purpura (TTP) episode, e.g. an initial episode and/or recurrent episode of TTP, results in improved outcomes, including a faster time to platelet count response lower proportion of patients with either death, recurrence or a major thromboembolic event (TE) during the treatment period, lower recurrence rate, and prevention of refractoriness. The invention provides a polypeptide comprising at least one ISVD against vWF for use in treating a vWF-related disease, preferably TTP, in a human in need thereof. The invention further relates to dosage unit forms, kits and medical uses for treating TTP.

2. BACKGROUND OF THE INVENTION 2.1 Role of vWF in Platelet Aggregation

The multimeric plasma protein vWF is essential for recruiting circulating platelets to the damaged vessel wall upon vascular injury. This recruitment is mediated through binding of the vWF A1-domain with the platelet receptor glycoprotein GPIb-IX-V.

Upon expression by endothelial cells, vWF is secreted into the circulation as ultra-large multimers or ultra-large vWF (ULvWF). These multimers are processed into smaller regular sized multimers through enzymatic cleavage by a disintegrin-like and metalloprotease with thrombospondin repeats 13 (ADAMTS13). In these regular sized multimers of vWF, the GPIb-IX-V platelet receptor binding site in the A1 domain is cryptic and will not spontaneously react with platelets. A conformational activation of the GPIb-IX-V platelet receptor binding site in the A1 domain is triggered by immobilisation or under conditions of shear stress resulting in platelet adhesion and subsequently in thrombus formation.

2.2 Role of vWF and vWF Processing in Pathophysiology of TTP

TTP is a rare and life-threatening disease of the blood coagulation system, in which accumulation of ULvWF multimers has been implicated, leading to an increased risk of thrombus formation in small blood vessels due to excessive platelet aggregation. The condition is characterised by systemic platelet aggregation in the microcirculation, producing fluctuating ischaemia in many organs. If sustained, this may cause tissue infarction, associated with profound thrombocytopenia and erythrocyte fragmentation.

ULvWF multimers have the natural ability to spontaneously interact with the platelet receptor GPIb-IX-V. ADAMTS13 activity was found to be severely deficient in hereditary TTP as well as acquired idiopathic TTP (aTTP). The majority of patients with TTP have autoantibodies against ADAMTS13 resulting in impaired processing of the ULvWF multimers. As a consequence, the A1 domain of the ULvWF is constitutively active and readily interacting with the GPIb-IX-V platelet receptor. This eventually results in formation of the characteristic blood clots found in the TTP patient population.

The current therapy of TTP with Plasma Exchange (abbreviated herein as "PE" or "PEX") and transfusion provides replacement ADAMTS13 and removes antibodies against the enzyme, thus progressively leading to a normalisation of ULvWF processing. However, this treatment requires multiple exchanges and transfusions over many days, during which time there is no direct pharmacological targeting of the active process of ULvWF-mediated platelet aggregation.

Although the introduction of PE and transfusion has significantly reduced the mortality rates from TTP over the last three decades, the condition still carries a significant risk of mortality and morbidity. The mortality rate of acute episodes in acute idiopathic TTP, in patients managed with the current therapies remains in the order of 10% to 30% (Vesely et al. Blood 2003; 102: 60-68; Allford et al. Br. J. Haematol. 2003; 120: 556-573; Sadler et al. Hematology. Am. Soc. Hematol. Educ. Program. 2004; 407-423). In the case of secondary TTP, PE and transfusion are recognised to be less effective and the mortality rate is considerably higher. In cases when the disease is secondary to pregnancy, in which PE is regarded as reasonably effective the mortality rate of an acute episode of TTP is approximately 25%, rising to over 40% in cases with concurrent pre-eclampsia (Martin et al. Am. J. Obstet. Gynecol. 2008; 199: 98-104). However, in cases secondary to, for example, underlying malignancies or bone marrow transplant the mortality rate remains at 40% to 60% despite the use of such treatment regimens (Sadler et al. 2004 supra; Elliott et al. Mayo Clin. Proc. 2003; 78: 421-430; Kremer Hovinga and Meyer Curr. Opin. Hematol. 2008; 15: 445-450.)

Given the continuing significant level of mortality from TTP and the observed complications of PE and transfusion, there is a clear need for the development of additional therapeutic approaches to supplement, or potentially reduce the need for, the contemporaneous methods of treatment.

The research conducted into TTP over the past three decades has improved the understanding of the pathophysiology of the disease allowing for the potential development of novel agents targeting the underlying disease processes.

Immunoglobulin single variable domains (ISVDs) against/binding vWF have been described in, for example, WO2004/015425, WO2004/062551, WO2006/074947, WO2006/122825, WO2009/115614 and WO2011/067160.

WO2015/193326 in the name of Ablynx describes, inter alia the unexpected finding that the administration of polypeptides comprising at least one ISVD binding vWF to human TTP patients provides a decrease in the time-to-response, objectified by a recovery of platelets ≥150,000/μL. This is reflected by a hazard (or platelet count normalization) ratio of 2.2, meaning that subjects treated with caplacizumab were 2.2 times more likely to achieve a platelet count response at any given time point. Thereby decreasing the thrombotic process initiated by the platelet-vWF complexes characteristic of this disease. Hence, proof of concept of the polypeptide of the invention was demonstrated with statistically significant and clinically meaningful reduction of time to confirmed platelet response. Furthermore, there was a reduction in the number of exacerbations from 11 in the Placebo arm to 3 in the treatment arm. There were no deaths in the treatment arm compared to 2 deaths in the Placebo arm. Indeed, it has been shown in phase II (TITAN) and phase III (HERCULES) studies that ISVDs against vWF (e.g. ALX 0081) are efficacious and safe in treating TTP patients.

However, WO2015/193326 and communications on the TITAN and HERCULES results have been silent on patients with an initial episode of aTTP.

If untreated, the mortality of TTP is 90%, which can be reduced with the prompt delivery of plasma exchange. Nevertheless, early death still occurs: approximately half of the deaths in the regional UK registry occurred within 24 h of presentation, primarily in women (Scully et al., 2008 BJH 142: 819-826). Hence, it is of the utmost importance to have a correct diagnosis of an aTTP episode (cf. Bindi et al. 2010 Transf Aph Sci 43:167-170). However, diagnosis can be difficult as there is clinical overlap with haemolytic uraemic syndrome (HUS), autoimmune disease and a spectrum of pregnancy-related problems (cf. Scully et al., 2012 BJH 158:323-335; George and Al-Nouri 2012 Hematology 604-609, Scully et al. 2017 J Thromb Haem 15:312-322). Indeed, the guidelines for diagnosing TTP—and related microangiopathies—have changed several times in recent years, from a pentad of thrombocytopenia, MAHA (microangiopathic hemolytic anemia, fluctuating neurological signs, renal impairment and fever, often with insidious onset, a diagnosis based on clinical history, examination of the patient and the blood film (Scully et al., 2012 BJH 158:323-335) to a diagnosis including (i) isolated MAHAT (microangiopathic hemolytic anemia and thrombocytopenia), (ii) new focal neurological symptoms, seizures, or myocardial infarction (MI), with unexplained MAHAT, and (iii) prior history of TTP (Scully et al. 2017 J Thromb Haem 15:312-322). ADAMTS13 assays help to confirm the diagnosis, monitoring the course of disease and even direct further treatment options. Correct diagnosis is complicated by the rare frequency of TTP in a population, because of which most physicians are not familiar with the symptoms, especially when a subject presents an initial episode of TTP. Indeed, initial episodes of TTP are often diagnosed later than recurrent episodes. In the latter cases, the patient and medical staff is aware of the medical history and recognizes the symptoms more easily. As a consequence, patients with an initial episode of TTP have a delayed presentation and more severe disease when entering the clinic than those with recurrent disease.

Therefore, it remains to be elucidated whether polypeptides comprising at least one ISVD against vWF, such as ALX 0081 or ALX 0081-A, are beneficial in patients with an initial episode of TTP, whether polypeptides comprising at least one ISVD against vWF, such as ALX 0081 or ALX 0081-A, have a positive effect, and what an effective treatment and dose regimen would be.

There is a need for improved therapies for TTP patients, especially when a subject presents an initial episode of TTP.

3. SUMMARY OF THE INVENTION

The present invention is based on the unexpected finding that the administration of polypeptides comprising at least one ISVD against vWF to human TTP patients improves outcomes of patients with an initial episode of TTP, who have a delayed presentation and more severe disease at baseline than those with recurrent disease, i.e. recurrent episode of TTP (cf. Example 7.11).

Moreover, the present invention also demonstrates that the polypeptides of the present invention (e.g. ALX 0081 or ALX 0081-A) led to faster normalization of platelet counts, prevented exacerbations, and prevented patients from becoming refractory to treatment. This was reflected inter alia in a reduction in plasma exchange parameters, days spent in the hospital and in the intensive care unit (ICU) (cf. Example 7.12).

In addition, the present invention shows that open-label (OL) therapy with the polypeptides of the present invention (e.g. ALX 0081 or ALX 0081-A) was efficacious in patients who experienced an exacerbation of aTTP (cf. Example 7.13).

The currently available data demonstrate, therefore, that the reduction in PE and transfusion and their associated complications are achieved without significant adverse effects from the use of the polypeptides of the invention itself. This represents a clear safety benefit for the use of the polypeptides of the invention in the treatment of patients with TTP.

Hence, the administration of polypeptides comprising at least one ISVD against vWF to human TTP patients provides an unexpectedly decreased time-to-response, a sustained and prolonged effect, reduced exacerbations, reduced hospitalization, including ICU occupation, reduced morbidity, reduced deaths and/or a reduced number of PEs in patients with an episode of TTP, e.g. an initial episode and/or recurrent episode of TTP.

Based on extensive mechanism-based pharmacokinetic-pharmacodynamic (PKPD) modelling, different scenarios were elaborated to support the dosing regimen. The model adequately described the drug-vWF complex interaction over time, including disease progression in aTTP patients and the effects governed by PE treatment. The model was successfully applied to facilitate the understanding of the PKPD interplay between caplacizumab and vWF in the target population, and by the use of simulations supported the dosing rational in both adult and paediatric patients and allowed bridging to Japanese aTTP patients (cf. Example 7.18). The population pharmacokinetic analysis in aTTP patients showed that age, gender, race, and blood group did not affect the pharmacokinetics of caplacizumab. Bodyweight and renal function, as expressed by the creatinine clearance (CrCL), had a statistically significant effect on the pharmacokinetics, with an expected higher exposure in patients with a lower bodyweight and CrCL. However, the expected exposure range in patient populations with extreme values of these covariates were largely overlapping and no specific dose-adjustment was deemed necessary. Baseline vWF levels had a statistically significant effect on drug exposure, but the increased drug exposure for patients with elevated vWF did not result in a different pharmacodynamic effect, and no individual dose-adjustment was deemed necessary (cf. Example 7.16.5).

Since no pediatric patients were enrolled in clinical trials with caplacizumab, this PKPD model was also used for dosing recommendations in adolescents and children. In contrast to above, the recommended dose in adolescents 12-18 years with a body weight ≥40 kg is 10 mg, and 5 mg if <40 kg. Since no differences in vWF:Ag suppression were expected based on differences in age, the same dosing recommendation applies for children 2-12 years: 10 mg if the body weight is ≥40 kg and 5 mg if <40 kg (cf. Example 7.19)

The current therapy of TTP with PE and transfusion provides replacement ADAMTS13 and removes antibodies against the enzyme, thus progressively leading to a normalisation of ULvWF processing. However, this treatment requires multiple exchanges and transfusions over many days, during which time there is no direct pharmacological targeting of the active process of ULvWF-mediated platelet aggregation.

During clinical trials in patients with aTTP, caplacizumab was administered as a 10 mg intravenous (i.v.) bolus prior to PE, followed by 10 mg daily subcutaneous (s.c.) doses during the daily PE period and at least 30 days thereafter. The potential effect of different time intervals between the first i.v. bolus and the subsequent PE, and the effect of different PE schedules, were also investigated. Surprisingly, effective drug levels are expected until PE is started up to 5 h following the first i.v. dose of caplacizumab. For longer delays, an additional 10 mg or 11 mg s.c. dose prior to PE can be envisaged. In case of bid (twice a day) PE for 7 days, the s.c. administration schedule of caplacizumab could be adjusted with bid caplacizumab after each PE treatment (cf. Example 7.17).

During a managed access program (MAP), patients received caplacizumab as frontline therapy or for the treatment of a refractory course of aTTP. The spontaneous safety reports were in line with the safety profile observed in clinical studies, without new safety signals. The first real world evidence with caplacizumab in aTTP patients confirm the important benefits of caplacizumab observed in clinical trials, particularly if started as frontline therapy.

The polypeptides of the present invention do not interfere with the enzyme replaced by plasma transfusion. The polypeptides of the invention (e.g. ALX 0081 or ALX 0081-A) can be utilized, in combination with PE and transfusion, to directly inhibit the continuing formation of small thrombi and platelet consumption in the microvasculature. This permits more rapid control of the underlying thrombotic process and accompanying platelet consumption, with the benefits of a reduced degree of ischaemic and haemorrhagic complications. It also results in a more rapid clinical recovery and less morbidity with a shorter period and reduced number of PEs and transfusions. Indeed, an analysis on the specific and clinically relevant organ damage biomarkers LDH, troponin T or I and creatinine suggested that more rapidly curtailing microvascular tissue ischemia have a clinical benefit. In addition, the demonstrated inhibition of ULvWF-mediated platelet interaction by the polypeptides of the invention (e.g. ALX 0081 or ALX 0081-A) and the observed antithrombotic effects show the positive effects for its longer-term use after patients have recovered from an acute episode of TTP, e.g. an initial episode and/or recurrent episode of TTP to prevent relapses and/or exacerbations of the disease. A reduced frequency of acute TTP episodes, e.g. an initial TTP episode and/or recurrent TTP episodes represents a significant benefit, with a potential for a reduction in the mortality and morbidity associated with TTP and a further reduction in the need for PE and transfusions over a patient's lifetime.

While a more rapid recovery from TTP and a reduction in exacerbations and relapses is a clear clinical benefit in terms of treatment efficacy, the reduction in the duration and frequency of PE and transfusion also provides additional benefits in terms of patient safety. Although PE and transfusion are currently regarded as the standard treatment in the management of TTP (Scully et al. Br. J. Haem. 2012; 158:323-335), the procedures carry the risk of significant complications. The PE procedure requires high fluid volumes and flow rates necessitating the use of central venous dual lumen haemodialysis catheters. Complications from the procedure include haemorrhage from catheter insertion, sepsis, catheter thrombosis, pneumothorax, fluid overload, hypoxia and hypotension (Fontana et al. Semin. Hematol. 2004; 41: 48-59; George J. Intensive Care Med. 2007; 22: 82-91; Howard et al. Transfusion 2006; 46: 154-156; Rizvi et al. Transfusion 2000; 40: 896-901; Nguyen et al. Transfusion 2009; 49: 392-394). Anaphylactoid reactions complicate 0.25% to 0.5% of procedures (Allford et al 2003 supra; George 2007 supra). In addition, the infusion of plasma containing blood products can cause a non-infective Transfusion related acute lung injury (TRALI). This condition is recognized as one of the most frequent causes of transfusion-related fatalities with an incidence estimated to be 0.02% to 0.05% per plasma containing unit. With a daily average of 17 plasma units, the daily risk can be calculated to a range of 0.34% to 0.85%. Most patients with TTP require multiple PEs and transfusions. Patients with acute idiopathic TTP require daily treatments, and an average of approximately 16 treatments is required to achieve remission (Allford et al. 2003 supra). In refractory cases the frequency of treatment may be increased to twice-daily (Allford et al. 2003 supra). In the case of patients with familial TTP, regular prophylactic plasma infusions at two to three week intervals are recommended (Lammle et al. J. Thromb. Haemost. 2005; 3: 1663-1675). Anaphylaxis and TRALI thus represent clear risks to patients with TTP whose treatment requires such a frequency and regularity of PEs and transfusions. While it is thought that this risk may be lower if solvent/detergent (S/D) treated plasma is used instead of fresh frozen plasma, the use of large volumes of S/D plasma may be associated with an increased risk of venous thromboembolism (Allford et al. 2003 supra; Fontana et al. 2004 supra). Overall, it is estimated that approximately 30% to 40% of patients will experience adverse effects from PE and transfusion, and the mortality rate from the procedure is of the order of 2% to 3% (George et al. Semin. Hematol. 2004; 41: 60-67; George 2007 supra; George and Al-Nouri 2012 supra). Hence, the reduction in the duration and frequency of PE and transfusion also provides additional benefits in terms of patient safety.

Following recovery from a TTP episode, e.g. an initial TTP episode and/or recurrent TTP episode, many patients describe cognitive abnormalities for many years and report troublesome problems with memory, concentration, decreased energy and fatigue. Such symptoms have a negative impact on the quality of patients' daily lives. Furthermore, this deficit in quality of life may occur in all patients who have TTP, regardless of the aetiology and severity (Lewis et al. Transfusion 2009; 49: 118-124). It is thought that these symptoms may be reflective of the residual effects of tissue ischaemia. On this basis, it can be reasonably proposed that a more rapid recovery from TTP and the limitation of thrombus formation in the microvasculature that the polypeptides of the present invention, such as ALX 0081 or ALX 0081-A, provide, results in an improved longer-term outcome for the patients in terms of their quality of life.

Surprisingly, it was shown in various in vitro experiments, comparative nuclear magnetic resonance (NMR) and Surface Plasmon Resonance (SPR) studies that caplacizumab and C-terminally-extended caplacizumab had similar characteristics and had similar binding profiles to the target vWF, although the C-terminally-extended caplacizumab had less pre-existing antibody binding. In view of the similar characteristics and profiles between caplacizumab and C-terminally extended caplacizumab, it is expected that these C-terminally extended caplacizumab compounds can be used in treating and/or preventing aTTP as well, similar to caplacizumab (cf. Example 7.21).

Accordingly, the present invention provides methods for treating or alleviating vWF-related diseases, such as TTP, in a subject by administering to the subject a polypeptide comprising at least one ISVD against vWF, wherein the amount of the polypeptide administered is effective to reduce the time-to-response, to reduce exacerbations, to reduce relapses, to reduce hospitalization, including ICU occupation, to reduce ischemia, to reduce the death toll and/or to reduce the number of required PEs. The present invention provides specific dose ranges and dosing schedules for the polypeptides of the invention that result in one or more of these beneficial effects on vWF-related disease, such as TTP. In particular, the invention provides pharmacologically active agents, compositions, methods and/or dosing schedules that have certain advantages compared to the agents, compositions, methods and/or dosing schedules that are currently used and/or known in the art, including the requirement to less frequently give PE. These advantages will become clear from the further description below.

In a preferred aspect, the invention relates to a polypeptide comprising two anti-human vWF immunoglobulin single variable domains (ISVDs) for use in treating (the symptoms of) an vWF-related disease in a human, preferably TTP, by administering to the human a dose of 10 mg or 11 mg of said polypeptide if said human has body weight ≥40 kg, and 5 mg if said body weight is <40 kg.

In an aspect the invention relates to a polypeptide comprising two anti-human von Willebrand Factor (vWF) immunoglobulin single variable domains (ISVDs) for use in treating (the symptoms of) an initial episode of an vWF-related disease in a human, preferably TTP, by administering to the human a dose of 1-80 mg, preferably 5-40 mg, even more preferably 10 mg or 11 mg of said polypeptide.

In an aspect the invention relates to a polypeptide comprising two anti-human von Willebrand Factor (vWF) immunoglobulin single variable domains (ISVDs) for use in a frontline treatment of a vWF-related disease in a human, preferably TTP, by administering to the human a dose of 1-80 mg, preferably 5-40 mg, even more preferably 10 mg or 11 mg of said polypeptide.

In a further aspect the invention relates to the polypeptide described herein for use in treating (the symptoms of) an initial episode of an vWF-related disease in a human, preferably TTP, wherein said step of administering the polypeptide of the invention is repeated for at least 1, 2, 3, 4, 5, 6, 7, 8, 9, or 10 days, or even more than 10 days, such as 20 days, preferably more than 30 days, such as 2 months, 3 months, 4 months, 5 months, 6 months or even more (treatment period).

In a further aspect the invention relates to the polypeptide described herein for use in treating (the symptoms of) an initial episode of an vWF-related disease in a human, preferably TTP, wherein said treatment results in a faster time to platelet count response, lower proportion of patients with either death, recurrence or a major TE event during the treatment period, lower recurrence rate, and/or prevention of refractoriness.

In a further aspect the invention relates to the polypeptide described herein for use in treating (the symptoms of) an initial episode of an vWF-related disease in a human, preferably TTP, wherein said polypeptide comprises at least one ISVD binding human vWF (SEQ ID NO: 20).

In a further aspect the invention relates to the polypeptide described herein for use in treating (the symptoms of) an vWF-related disease in a human, preferably TTP, wherein said polypeptide is at least 90% identical to SEQ ID NO: 1 and comprising a C-terminal extension (X)n, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I); even more preferably alanine.

In a further aspect the invention relates to the polypeptide described herein for use in treating (the symptoms of) an initial episode of an vWF-related disease in a human, wherein at least one ISVD is represented by SEQ ID NO: 19 (12A02H1).

In a further aspect the invention relates to the polypeptide described herein for use in treating (the symptoms of) an initial episode of an vWF-related disease in a human, preferably TTP, wherein said polypeptide is at least 90% identical to SEQ ID NO: 1.

In a further aspect the invention relates to the polypeptide described herein for use in treating (the symptoms of) an initial episode of an vWF-related disease in a human, preferably TTP, wherein said polypeptide is ALX 0081 (SEQ ID NO: 1) or ALX 0081-A (SEQ ID NO: 24).

In a further aspect the invention relates to the polypeptide described herein for use in treating (the symptoms of) an initial episode of an vWF-related disease in a human, preferably TTP, wherein said dose is administered 1 time per day or two times per day.

In a further aspect the invention relates to the polypeptide described herein for use in treating (the symptoms of) an initial episode of an vWF-related disease in a human, preferably TTP, comprising repeating administering said polypeptide until the platelet number in said human is at least 150,000/µl.

In a further aspect the invention relates to the polypeptide described herein for use in treating (the symptoms of) an initial episode of an vWF-related disease in a human, comprising repeating administering said polypeptide until the platelet number in said human is at least 150,000/µl on at least 2 consecutive measurements.

In a further aspect the invention relates to the polypeptide described herein for use in treating (the symptoms of) an initial episode of an vWF-related disease in a human, preferably TTP, wherein said step of administering the polypeptide of the invention is repeated for at least 1, 2, 3, 4, 5, 6, 7, 8, 9, or 10 days, or even more than 10 days, such as 20 days, preferably more than 30 days or even more, after said platelet number is at least 150,000/µl on at least 2 consecutive measurements.

In a further aspect the invention relates to the polypeptide described herein for use in treating (the symptoms of) an initial episode of an vWF-related disease in a human, wherein said 2 consecutive measurements are at least 24 h, more preferably 48 h apart, such as at least 3 days apart, or even more such as 4, 5, 6, or even 7 days apart, preferably a week apart.

In a further aspect the invention relates to the polypeptide described herein for use in treating (the symptoms of) an initial episode of an vWF-related disease in a human, preferably TTP, comprising repeating administering said polypeptide until the ADAMTS13 activity in said human is at least 10% such as at least 15%, 20%, 25%, 30%, 35%, 45% or even 50% of an ADAMTS13 reference activity.

In a further aspect the invention relates to the polypeptide described herein for use in treating (the symptoms of) an initial episode of an vWF-related disease in a human, preferably TTP, comprising repeating administering said polypeptide until the level of an organ damage marker, such as LDH level, troponin T level, troponin I level, and/or creatinine level, in said human returns to at least 40%, or even at least 50%, such as 60%, 70%, 80%, 90% or even to 100% of normal levels In a further aspect the invention relates to the polypeptide described herein for use in treating (the symptoms of) an initial episode of an vWF-related disease in a human, preferably TTP, comprising performing a Plasma Exchange.

In a further aspect the invention relates to the polypeptide described herein for use in treating (the symptoms of) an initial episode of an vWF-related disease in a human, wherein said vWF-related disease is chosen from acute coronary syndrome (ACS), transient cerebral ischemic attack, unstable or stable angina pectoris, stroke, myocardial infarction or thrombotic thrombocytopenic purpura (TTP), preferably TTP.

In an aspect the invention relates to a polypeptide comprising two anti-human von Willebrand Factor (vWF) immunoglobulin single variable domains (ISVDs) for use in reducing days in hospital and/or intensive care unit (ICU) during treating an acute episode of a vWF-related disease in a human in need thereof, preferably TTP, comprising administering to the human a dose of 1-80 mg, preferably 5-40 mg, even more preferably 10 mg or 11 mg of said polypeptide.

In a further aspect the invention relates to the polypeptide described herein for use in reducing days in hospital and/or intensive care unit (ICU) during treating an acute episode of a vWF-related disease in a human in need thereof, preferably TTP, wherein said step of administering the polypeptide of the invention is repeated for at least 1, 2, 3, 4, 5, 6, 7, 8, 9, or 10 days, or even more than 10 days, such as 20 days, preferably more than 30 days, such as 2 months, 3 months, 4 months, 5 months, 6 months or even more (treatment period).

In a further aspect the invention relates to the polypeptide described herein for use in reducing days in hospital and/or intensive care unit (ICU) during treating an acute episode of a vWF-related disease in a human in need thereof, preferably TTP, wherein said treatment results in a faster time to platelet count response, lower proportion of patients with either death, recurrence or a major TE event during the treatment period, lower recurrence rate, and/or prevention of refractoriness.

In a further aspect the invention relates to the polypeptide described herein for use in reducing days in hospital and/or intensive care unit (ICU) during treating an acute episode of a vWF-related disease in a human in need thereof, preferably TTP, wherein said polypeptide comprises at least one ISVD binding SEQ ID NO: 20.

In a further aspect the invention relates to the polypeptide described herein for use in reducing days in hospital and/or intensive care unit (ICU) during treating an acute episode of a vWF-related disease in a human in need thereof, preferably TTP, wherein at least one ISVD is represented by SEQ ID NO: 19 (12A02H1).

In a further aspect the invention relates to the polypeptide described herein for use in reducing days in hospital and/or intensive care unit (ICU) during treating an acute episode of a vWF-related disease in a human in need thereof, preferably TTP, wherein said polypeptide is at least 90% identical to SEQ ID NO: 1.

In a further aspect the invention relates to the polypeptide described herein for use in reducing days in hospital and/or intensive care unit (ICU) during treating an acute episode of a vWF-related disease in a human in need thereof, preferably TTP, wherein said polypeptide is ALX 0081 (SEQ ID NO: 1) or ALX 0081-A (SEQ ID NO: 24).

In a further aspect the invention relates to the polypeptide described herein for use in reducing days in hospital and/or intensive care unit (ICU) during treating an acute episode of a vWF-related disease in a human in need thereof, preferably TTP, wherein said dose is administered 1 time per day or two times per day.

In a further aspect the invention relates to the polypeptide described herein for use in reducing days in hospital and/or intensive care unit (ICU) during treating an acute episode of a vWF-related disease in a human in need thereof, preferably TTP, comprising repeating administering said polypeptide until the platelet number in said human is at least 150,000/µl.

In a further aspect the invention relates to the polypeptide described herein for use in reducing days in hospital and/or intensive care unit (ICU) during treating an acute episode of a vWF-related disease in a human in need thereof, preferably TTP, comprising repeating administering said polypeptide until the platelet number in said human is at least 150,000/µl on at least 2 consecutive measurements.

In a further aspect the invention relates to the polypeptide described herein for use in reducing days in hospital and/or intensive care unit (ICU) during treating an acute episode of a vWF-related disease in a human in need thereof, preferably TTP, wherein said step of administering the polypeptide of the invention is repeated for at least 1, 2, 3, 4, 5, 6, 7, 8, 9, or 10 days, or even more than 10 days, such as 20 days, preferably more than 30 days or even more, after said platelet number is at least 150,000/µl on at least 2 consecutive measurements.

In a further aspect the invention relates to the polypeptide described herein for use in reducing days in hospital and/or intensive care unit (ICU) during treating an acute episode of a vWF-related disease in a human in need thereof, preferably TTP, wherein said 2 consecutive measurements are at least 24 h, more preferably 48 h apart, such as at least 3 days apart, or even more such as 4, 5, 6, or even 7 days apart, preferably a week apart.

In a further aspect the invention relates to the polypeptide described herein for use in reducing days in hospital and/or intensive care unit (ICU) during treating an acute episode of a vWF-related disease in a human in need thereof, preferably TTP, comprising repeating administering said polypeptide until the ADAMTS13 activity in said human is at least 10% such as at least 15%, 20%, 25%, 30%, 35%, 45% or even 50% of an ADAMTS13 reference activity.

In a further aspect the invention relates to the polypeptide described herein for use in reducing days in hospital and/or intensive care unit (ICU) during treating an acute episode of a vWF-related disease in a human in need thereof, preferably TTP, comprising repeating administering said polypeptide until the level of an organ damage marker, such as LDH level, troponin T level, troponin I level, and/or creatinine level, in said human returns to at least 40%, or even at least 50%, such as 60%, 70%, 80%, 90% or even to 100% of normal levels In a further aspect the invention relates to the polypeptide described herein for use in reducing days in hospital and/or intensive care unit (ICU) during treating an acute episode of a vWF-related disease in a human in need thereof, preferably TTP, comprising performing a Plasma Exchange.

In a further aspect the invention relates to the polypeptide described herein for use in reducing days in hospital and/or intensive care unit (ICU) during treating an acute episode of a vWF-related disease in a human in need thereof, wherein said vWF-related disease is chosen from acute coronary syndrome (ACS), transient cerebral ischemic attack, unstable or stable angina pectoris, stroke, myocardial infarction or thrombotic thrombocytopenic purpura (TTP), preferably TTP.

In an aspect the invention relates to a polypeptide comprising two anti-human von Willebrand Factor (vWF) immunoglobulin single variable domains (ISVDs) for use in preventing patients from becoming refractory to treatment of an acute episode, e.g. an initial episode and/or recurrent episode of a vWF-related disease in a human in need thereof, preferably TTP, comprising administering to the human a dose of 1-80 mg, preferably 5-40 mg, even more preferably 10 mg or 11 mg of said polypeptide.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said step of administering the polypeptide of the invention is repeated for at least 1, 2, 3, 4, 5, 6, 7, 8, 9, or 10 days, or even more than 10 days, such as 20 days, preferably more than 30 days, such as 2 months, 3 months, 4 months, 5 months, 6 months or even more (treatment period).

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said treatment results in a faster time to platelet count response, lower proportion of patients with either death, recurrence or a major TE event during the treatment period, lower recurrence rate, and/or prevention of refractoriness.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said polypeptide comprises at least one ISVD binding SEQ ID NO: 20.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein at least one ISVD is represented by SEQ ID NO: 19 (12A02H1).

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said polypeptide is at least 90% identical to SEQ ID NO: 1.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said polypeptide is ALX 0081 (SEQ ID NO: 1) or ALX 0081-A (SEQ ID NO: 24).

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said dose is administered 1 time per day or two times per day.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, comprising repeating administering said polypeptide until the platelet number in said human is at least 150,000/µl.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, comprising repeating administering said polypeptide until the platelet number in said human is at least 150,000/µl on at least 2 consecutive measurements.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said step of administering the polypeptide of the invention is repeated for at least 1, 2, 3, 4, 5, 6, 7, 8, 9, or 10 days, or even more than 10 days, such as 20 days, preferably more than 30 days or even more, after said platelet number is at least 150,000/µl on at least 2 consecutive measurements.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, wherein said 2 consecutive measurements are at least 24 h, more preferably 48 h apart, such as at least 3 days apart, or even more such as 4, 5, 6, or even 7 days apart, preferably a week apart.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, comprising repeating administering said polypeptide until the ADAMTS13 activity in said human is at least 10% such as at least 15%, 20%, 25%, 30%, 35%, 45% or even 50% of an ADAMTS13 reference activity.

In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, comprising repeating administering said polypeptide until the level of an organ damage marker, such as LDH level, troponin T level, troponin I level, and/or creatinine level, in said human returns to at least 40%, or even at least 50%, such as 60%, 70%, 80%, 90% or even to 100% of normal levels In a further aspect the invention relates to the polypeptide described herein for use in preventing patients from becoming refractory to treatment of an acute episode, e.g. an initial episode and/or recurrent episode of a vWF-related disease in a human in need thereof, preferably TTP, comprising performing a Plasma Exchange.

In a further aspect the invention relates to the polypeptide described herein for use in preventing patients from becoming refractory to treatment of an acute episode, e.g. an initial episode and/or recurrent episode of a vWF-related disease in a human in need thereof, wherein said vWF-related disease is chosen from acute coronary syndrome (ACS), transient cerebral ischemic attack, unstable or stable angina pectoris, stroke, myocardial infarction or thrombotic thrombocytopenic purpura (TTP), preferably TTP.

Accordingly, the present invention provides a polypeptide comprising at least one ISVD against vWF, preferably 2 ISVDs, even more preferably ALX 0081 or ALX 0081-A, for use in treating and/or preventing a vWF-related disease in a human in need thereof as described herein, preferably TTP, comprising administering to said human a first dose of 1-80 mg, such as 5-40 mg, preferably 10 mg or 11 mg of said polypeptide.

The present invention provides a polypeptide as described herein, for use in treating and/or preventing a vWF-related disease in a human in need thereof as described herein, preferably TTP, wherein said administering said polypeptide is followed within 5 min to 8 h by performing a first PE.

The present invention provides a polypeptide as described herein, for use in treating and/or preventing a vWF-related disease in a human in need thereof as described herein, preferably TTP, wherein said administering of said first dose is preceded by performing a preceded PE, preferably within 36 h, such as within 32 h, 30 h, 28 h, 26 h, 24 h, 22 h, 20 h, 18 h, 16 h, 14 h, 12 h, 10 h, 8 h, for instance within 7 h, 6 h, 5 h, 4 h, 3 h, 3 h, 1 h, 45 min, 30 min, 20 min, 15 min, 10 min or even 5 min of said first PE.

The present invention provides a polypeptide as described herein, for use in treating and/or preventing a vWF-related disease in a human in need thereof as described herein, preferably TTP, wherein said first PE is followed by administering a second dose of 1-80 mg, such as 5-40 mg, preferably 10 mg or 11 mg, of said polypeptide, preferably by subcutaneous injection, preferably within 1-60 min, more preferably within 30 min of said first PE.

The present invention provides a polypeptide as described herein, for use in treating and/or preventing a vWF-related disease in a human in need thereof as described herein, preferably TTP, wherein said preceded PE is performed within 36 h, preferably 32, 30, 28, 26, 24, 22, 20, 18, or 16 h, preferably about 24 h of said first PE.

The present invention provides a polypeptide as described herein, for use in treating and/or preventing a vWF-related disease in a human in need thereof as described herein, preferably TTP, wherein said polypeptide is administered parenterally, preferably by subcutaneous, intraperitoneal, intravenous or intra-muscular injection, preferably by an intravenous (i.v.) bolus push injection.

The present invention provides a polypeptide as described herein, for use in treating and/or preventing a vWF-related disease in a human in need thereof as described herein, preferably TTP, wherein administering said polypeptide is followed by performing a PE within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min, preferably within less than 5 h.

The present invention provides a polypeptide as described herein, for use in treating and/or preventing a vWF-related disease in a human in need thereof as described herein, preferably TTP, wherein said treating a vWF-related disease, such as TTP, in a human in need thereof, preferably TTP, further comprises:
  (i) performing a PE; and (followed by)
  (ii) administering a dose of 1-80 mg, such as 5-40 mg of said polypeptide 5 min to 4 h after said PE of step (i); and
  (iii) optionally measuring the platelet count and/or ADAMTS13 activity of said patient,
wherein step (i) and step (ii) are repeated once per day, preferably until the platelet count of said patient is ≥150000/μl and/or said ADAMTS13 activity is at least 10% such as at least 15%, 20%, 25%, 30%, 35%, 45% or even 50% of the ADAMTS13 reference activity.

The present invention provides a polypeptide as described herein, for use in treating and/or preventing a vWF-related disease in a human in need thereof as described herein, preferably TTP, further comprising administering once per day a dose of 1-80 mg, such as 5-40 mg, preferably 10 mg or 11 mg of said polypeptide for at least 5, 10, 15, 20, 25, 30, 40, 50 60, 90 or even 120 days after the platelet count of said patient is ≥150.000/μl for the first time.

The present invention provides a polypeptide as described herein, for use in treating and/or preventing a vWF-related disease in a human in need thereof as described herein, preferably TTP, further comprising administering once per day a dose of 1-80 mg, such as 5-40 mg, preferably 10 mg or 11 mg of said polypeptide until said human enters remission.

The present invention provides a polypeptide as described herein, for use in treating and/or preventing a vWF-related disease in a human in need thereof as described herein, preferably TTP, comprising administering said polypeptide until the ADAMTS13 activity is at least 10% such as at least 15%, 20%, 25%, 30%, 35%, 45% or even 50% of the ADAMTS13 reference activity.

The present invention provides a polypeptide as described herein, wherein said dose is about 1-80 mg, or 5-40 mg, such as 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably about 10 mg or 11 mg of said polypeptide.

The present invention provides a polypeptide as described herein, for use in treating and/or preventing a vWF-related disease in a human in need thereof as described herein, preferably TTP, wherein said human suffers from a TTP episode, e.g. an initial TTP episode and/or recurrent TTP episode, an exacerbation of TTP and/or a relapse of TTP.

In a preferred aspect, the present invention provides a polypeptide comprising at least one ISVD against vWF for use in treating a vWF-related disease, such as TTP, in a human in need thereof, preferably TTP, as described herein, comprising
  (1) optionally performing a preceding PE;
  (2) administering to said human a first dose of 1-80 mg, such as 5-40 mg, preferably 10 mg or 11 mg of said polypeptide, and if step (1) is performed preferably within 36 h, such as within 32 h, 30 h, 28 h, 26 h, 24 h, 22 h, 20 h, 18 h, 16 h, 14 h, 12 h, 10 h, 8 h, for instance within 7 h, 6 h, 5 h, 4 h, 3 h, 3 h, 1 h, 45 min, 30 min, 20 min, 15 min, 10 min or even 5 min of (the end of) step (1);
  (3) performing a PE, optionally within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min of step (2);
  (4) administering a further dose of 1-80 mg, such as 5-40 mg, preferably 10 mg or 11 mg of said polypeptide preferably within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min of (the end of) step (3);
  (5) repeating step (3) and step (4) once per day; optionally until the platelet count of said patient is ≥150000/μl and/or said ADAMTS13 activity is at least 10% such as at least 15%, 20%, 25%, 30%, 35%, 45% or even 50% of the ADAMTS13 reference activity.
  (6) optionally administering once per day a dose of 1-80 mg, such as 5-40 mg, preferably 10 mg or 11 mg of said polypeptide for at least 5, 10, 15, 20, 25, 30, 40, 50 60, 90 or even 120 days after the platelet count of said patient is ≥150.000/μl for the first time or until the ADAMTS13 activity is at least 10% such as at least 15%, 20%, 25%, 30%, 35%, 45% or even 50% of the ADAMTS13 reference activity.

If step (3) is performed after 5 h of step (2), then administering a further dose of 1-80 mg, such as 5-40 mg, preferably 10 mg or 11 mg of said polypeptide.

In another preferred aspect, the present invention provides a polypeptide comprising at least one ISVD against vWF for use in treating a vWF-related disease, such as TTP, in a human in need thereof, preferably TTP, as described herein, comprising
(1) performing a PE twice a day;
(2) administering to said human a dose of 1-80 mg, such as 5-40 mg, preferably 10 mg or 11 mg of said polypeptide after each PE of step (1).

In addition, the present invention provides a polypeptide comprising two anti-human vWF ISVDs for use in preventing (the symptoms of) a relapse of an vWF-related disease in a human, by administering to the human 1-80 mg, such as 5-40 mg, preferably 10 mg or 11 mg doses of said polypeptide.

The present invention provides a polypeptide as described herein, wherein said ISVD against vWF comprises at least one immunoglobulin single variable domain binding to SEQ ID NO: 20.

The present invention provides a polypeptide as described herein, wherein said ISVD against vWF comprises a heavy chain variable domain which is derived from a conventional four-chain antibody or a heavy chain variable domain which is derived from a heavy chain antibody or a Nanobody.

The present invention provides a polypeptide as described herein, wherein said Nanobody is a VHH.

The present invention provides a polypeptide as described herein, wherein said the ISVD against vWF essentially consists of 4 framework regions (FR1 to FR4, respectively) and 3 complementarity determining regions (CDR1 to CDR3, respectively), in which:
a) CDR1 comprises or essentially consists of:
the amino acid sequence YNPMG; or
an amino acid sequence that has 2 or only 1 amino acid difference(s) with the amino acid sequence YNPMG; and
b) CDR2 comprises or essentially consists of:
the amino acid sequence AISRTGGSTYYPDSVEG; or
an amino acid sequence that has at least 80%, preferably at least 90%, more preferably at least 95%, even more preferably at least 99% sequence identity with the amino acid sequence AISRTGGSTYYPDSVEG; or
an amino acid sequence that has 2 or only 1 amino acid difference(s) with the amino acid sequence AISRTGGSTYYPDSVEG;
and
c) CDR3 comprises or essentially consists of:
the amino acid sequence AGVRAEDGRVRTLPSEYTF; or
an amino acid sequence that has at least 80%, preferably at least 90%, more preferably at least 95%, even more preferably at least 99% sequence identity with the amino acid sequence AGVRAEDGRVRTLPSEYTF; or
an amino acid sequence that has 2 or only 1 amino acid difference(s) with the amino acid sequence AGVRAEDGRVRTLPSEYTF.

The present invention provides a polypeptide as described herein, in which:
a) CDR1 is YNPMG (SEQ ID NO: 21);
b) CDR2 is AISRTGGSTYYPDSVEG (SEQ ID NO: 22); and
c) CDR3 is AGVRAEDGRVRTLPSEYTF (SEQ ID NO: 23).

The present invention provides a polypeptide as described herein, wherein the ISVD against vWF is represented by SEQ ID NO: 19 (12A02H1).

The present invention provides a polypeptide as described herein, comprising or consisting of at least two ISVDs against vWF.

The present invention provides a polypeptide as described herein, wherein each ISVD of said at least two ISVDs against vWF essentially consists of 4 framework regions (FR1 to FR4, respectively) and 3 complementarity determining regions (CDR1 to CDR3, respectively), in which:
a) CDR1 comprises or essentially consists of:
the amino acid sequence YNPMG; or
an amino acid sequence that has 2 or only 1 amino acid difference(s) with the amino acid sequence YNPMG; and
b) CDR2 comprises or essentially consists of:
the amino acid sequence AISRTGGSTYYPDSVEG; or
an amino acid sequence that has at least 80%, preferably at least 90%, more preferably at least 95%, even more preferably at least 99% sequence identity with the amino acid sequence AISRTGGSTYYPDSVEG; or
an amino acid sequence that has 2 or only 1 amino acid difference(s) with the amino acid sequence AISRTGGSTYYPDSVEG;
and
c) CDR3 comprises or essentially consists of:
the amino acid sequence AGVRAEDGRVRTLPSEYTF; or
an amino acid sequence that has at least 80%, preferably at least 90%, more preferably at least 95%, even more preferably at least 99% sequence identity with the amino acid sequence AGVRAEDGRVRTLPSEYTF; or
an amino acid sequence that has 2 or only 1 amino acid difference(s) with the amino acid sequence AGVRAEDGRVRTLPSEYTF.

The present invention provides a polypeptide as described herein, in which each ISVD against vWF essentially consists of 4 framework regions (FR1 to FR4, respectively) and 3 complementarity determining regions (CDR1 to CDR3, respectively), in which:
a) CDR1 is YNPMG (SEQ ID NO: 21);
b) CDR2 is AISRTGGSTYYPDSVEG (SEQ ID NO: 22); and
c) CDR3 is AGVRAEDGRVRTLPSEYTF (SEQ ID NO: 23).

The present invention provides a polypeptide as described herein, wherein said polypeptide comprises or consists of SEQ ID NO:s 1-18 or 24, preferably SEQ ID NO: 1 or 24.

The present invention provides a polypeptide as described herein, wherein said ISVD against vWF is a single chain polypeptide comprising one or more immunoglobulin single variable domains.

The present invention provides a polypeptide as described herein, wherein said ISVD against vWF is monovalent or multivalent.

The present invention provides a polypeptide as described herein, wherein said ISVD against vWF is monospecific or multispecific.

The present invention provides a polypeptide as described herein, wherein one or more immunoglobulin single variable domains are CDR-grafted, humanized, camelized, de-immunized, or selected by phage display.

The present invention provides a polypeptide as described herein, wherein said ISVD against vWF comprises an amino acid sequence which is at least 90% identical to SEQ ID NO: 1.

The present invention provides a polypeptide as described herein, comprising two anti-human vWF immunoglobulin single variable domains (ISVDs) and an anti-human serum albumin (HSA) ISVD The present invention provides a polypeptide as described herein, wherein said polypeptide is formulated in a pharmaceutically acceptable formulation.

The present invention provides a polypeptide as described herein, wherein said formulation comprises a citrate or phosphate buffer with a pH in the range of 5.0 to 7.5.

The present invention provides a polypeptide as described herein, wherein said formulation is suitable for parenteral administration, such as one or more selected from intravenous injection, subcutaneous injection, intramuscular injection or intraperitoneal injection.

The present invention provides a polypeptide as described herein, wherein said formulation is in liquid, lyophilized, spray-dried, reconstituted lyophilized or frozen form.

The present invention provides a kit or an article of manufacture, comprising a container containing the polypeptide as described herein or the formulation as described herein, and instructions for use.

The present invention provides a kit or article of manufacture as described herein, wherein the formulation is present in a vial or an injectable syringe.

The present invention provides a kit or article of manufacture as described herein, wherein the formulation is present in a prefilled injectable syringe.

The present invention provides a kit or article of manufacture as described herein, wherein the syringe or a vial is composed of glass, plastic, or a polymeric material chosen from a cyclic olefin polymer or copolymer.

The present invention provides a formulation comprising:
(a) a polypeptide as described herein at a concentration from about 0.1 mg/mL to about 80 mg/mL;
(b) an excipient chosen from sucrose, glycine, mannitol, trehalose or NaCl at a concentration of about 1% to about 15% (w/v);
(c) Tween-80 at a concentration of about 0.001% to 0.5% (v/v); and
(d) a buffer chosen from citrate buffer at a concentration of about 5 mM to about 200 mM such that the pH of the formulation is about 6.0 to 7.0 and a phosphate buffer at a concentration of about 10 mM to about 50 mM such that the pH of the formulation is about 6.5 to 7.5,
for use in treating a vWF-related disease in a human in need thereof, preferably TTP, by administering to the human a 1-80 mg, such as 5-40 mg dose, preferably 10 mg or 11 mg of said polypeptide, wherein said dose is optionally followed within 5 min to 8 h, such as 15 min to 4 h by a first Plasma Exchange (PE).

The present invention provides a pharmaceutical unit dosage form suitable for parenteral administration to a patient, preferably a human patient, comprising a polypeptide as described herein or a formulation as described herein.

The present invention provides a polypeptide as described herein, wherein said vWF-related disease is chosen from acute coronary syndrome (ACS), transient cerebral ischemic attack, unstable or stable angina pectoris, stroke, myocardial infarction or (acquired and/or congenital) thrombotic thrombocytopenic purpura (TTP), preferably TTP.

The present invention provides a method for the treatment of a human patient susceptible to or diagnosed with a vWF-related disease, such as TTP, comprising administering an effective amount of a polypeptide comprising at least one immunoglobulin single variable domain (ISVD) against von Willebrand Factor (vWF) to the human patient.

The present invention provides a method of treating or preventing a vWF-related disease, such as TTP, comprising administering to a human, 1-80 mg, such as 5-40 mg, preferably 10 mg or 11 mg dose of a polypeptide comprising at least one immunoglobulin single variable domain (ISVD) against von Willebrand Factor (vWF), thereby reducing one or more symptoms associated with the vWF-related disease.

The present invention provides a treatment as described herein, wherein said administering a polypeptide as described herein is followed within 5 min to 8 h, such as 15 min to 4 h by performing a first Plasma Exchange (PE).

The present invention provides a treatment as described herein, wherein said administering of a polypeptide as described herein is preceded by performing a preceded Plasma Exchange (PE), within 36 h, preferably 32, 30, 28, 26, 24, 22, 20, 18, or 16 h, preferably about 24 h of said first PE.

The present invention provides a treatment as described herein, wherein said first PE is followed by administering a second dose of 1-80 mg, such as 5-40 mg, preferably 10 mg or 11 mg of a polypeptide as described herein within 5 min to 8 h, such as within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min, for instance wherein said second dose of said polypeptide is administered within 1-60 min, such as 30 min of said first PE, preferably by subcutaneous injection.

The present invention provides a treatment as described herein, further comprising:
(i) performing a PE; (followed by)
(ii) administering a dose of 1-80 mg such as 5-40 mg, preferably 10 mg or 11 mg of a polypeptide as described herein 15 min to 4 h after said PE of step (i); and
(iii) optionally measuring the platelet count and/or ADAMTS13 activity of said patient, wherein step (i) and step (ii) are repeated once per day optionally until the platelet count of said patient is ≥150000/µl and/or the ADAMTS13 activity is at least 10% such as at least 15%, 20%, 25%, 30%, 35%, 45% or even 50% of the ADAMTS13 reference activity.

The present invention provides also a treatment as described herein, further comprising administering once per day a dose of 1-80 mg, such as 5-40 mg, preferably 10 mg or 11 mg of a polypeptide as described herein for at least 5, 10, 15, 20, 25, or even 30 days after the platelet count of said patient is ≥150.000/µl.

The present invention provides a treatment as described herein, further comprising administering once per day a dose of 1-80 mg, such as 5-40 mg, preferably 10 mg or 11 mg of a polypeptide as described herein until said human enters remission.

The present invention provides a treatment as described herein, comprising administering said polypeptide until the ADAMTS13 activity is at least 10% such as at least 15%, 20%, 25%, 30%, 35%, 45% or even 50% of the ADAMTS13 reference activity.

In an embodiment, the present invention relates to a method for reducing the risk of and/or preventing an acute episode of a vWF-related disease in a human in need thereof, such as an episode of TTP, e.g. an initial episode and/or recurrent episode of TTP, comprising or consisting of: (i) administering to said human a dose of 5-40 mg, preferably 10 mg or 11 mg, of a polypeptide comprising at least one immunoglobulin single variable domain (ISVD) against von Willebrand Factor (vWF); wherein administration of said polypeptide reduces the risk of and/or prevents an acute episode of a vWF-related disease, such as an episode of TTP, e.g. an initial episode and/or recurrent episode of TTP. Preferably, said risk is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100. Preferably, said risk is reduced by 10% or even more such as 20%, 30%, 40%, 50%, 60% or more, such as 80% or even 100%.

In an embodiment, the present invention relates to a method as described herein, wherein said step (i) of administering the polypeptide of the invention is repeated for at least 1, 2, 3, 4, 5, 6, 7, 8, 9, or times, or even more than 10 times, such as 20 times, preferably more than 30 times or even more.

In an embodiment, the present invention relates to a method as described herein, wherein said step (i) of administering the polypeptide of the invention is repeated for at least 1, 2, 3, 4, 5, 6, 7, 8, 9, or 10 days, or even more than 10 days, such as 20 days, preferably more than 30 days, such as 2 months, 3 months, 4 months, 5 months, 6 months or even more.

In an embodiment, the present invention relates to a method as described herein, wherein said dose is administered 1 time per day or two times per day (bid).

In an embodiment, the present invention relates to a method as described herein, further comprising
  (ii) optionally measuring the ADAMTS13 activity of said patient;
  (iii) optionally comparing the ADAMTS13 activity of said patient with a reference ADAMTS13 activity; and
  (iv) if said ADAMTS13 activity is lower than 30%, such as 20%, 15% or 10% of said reference ADAMTS13 activity, then repeating said step (i) of administering the polypeptide of the invention.

In an embodiment, the present invention relates to a method as described herein, wherein said ADAMTS13 activity of said patient is measured every day, or every 2, 3, 4, 5, 6, 7, 8, 9, or 10 days, preferably at least once every week.

In an embodiment, the present invention relates to a method as described herein, wherein said step of administering the polypeptide of the invention is repeated until said ADAMTS13 activity is at least 10%, 15%, such 20%, or even 30% or higher of said reference ADAMTS13 activity.

In an embodiment, the present invention relates to a method as described herein, wherein step (i) is repeated until said ADAMTS13 activity is at least 10%, 15%, such as 20% or 30% of said reference ADAMTS13 activity on at least 2 consecutive measurements. Preferably, said 2 consecutive measurements are at least 24 h, more preferably 48 h apart, such as at least 3 days apart, or even more such as, 4, 5, 6, or even 7 days apart, preferable a week apart.

In an embodiment, the present invention relates to a method as described herein, wherein said step (i) of administering the polypeptide of the invention is repeated for at least at least 1, 2, 3, 4, 5, 6, 7, 8, 9, or 10 days, or even more than 10 days, such as 20 days, preferably more than 30 days or even more, after said ADAMTS13 activity is at least 10% or 15%, such as 20% or 30% of said reference activity on at least 2 consecutive measurements.

In an embodiment, the present invention relates to a method as described herein, further comprising
  optionally measuring the ADAMTS13 activity of said patient;
  optionally comparing the ADAMTS13 activity of said patient with a reference ADAMTS13 activity; and
  if said ADAMTS13 activity is ≥10%, such as more than 15%, or more than 20% or 30% of said reference ADAMTS13 activity, then repeating said step (i) of administering the polypeptide of the invention for at most 30 days, such as at most 20 days, or even 15, 10, 9, 8, 7, 6, 5, 4, 3, 2 days or even 1 day.

In an embodiment, the present invention relates to a method for reducing the risk of and/or preventing an acute episode of a vWF-related disease in a human in need thereof, such as an episode of TTP, e.g. an initial episode and/or recurrent episode of TTP, comprising at least the following steps:
  (i) measuring the ADAMTS13 activity of said patient;
  (ii) comparing said ADAMTS13 activity with a reference ADAMTS13 activity; and
  (iii) if said ADAMTS13 activity is lower than 30%, 20%, 15% or 10% of said reference activity, then administering to said human a dose of 5-40 mg, such as 10 mg or 11 mg, of a polypeptide comprising at least one immunoglobulin single variable domain (ISVD) against von Willebrand Factor (vWF);

In an embodiment, the present invention relates to a method as described herein, wherein
  the risk of organ damage, ischaemic damage and/or microthrombi formation is reduced by 10%, 20%, 30%, preferably by at least 40%, or even at least 50%, such as 60%, 70%, 80%, 90% or even to 100%;
  the risk of organ damage, ischaemic damage and/or microthrombi formation is reduced by a factor 1.2. 1.3, 1.4, 1.5, 1.75, 2 or more, such as 3, 4, 5, 6, 7, 8, 9, or even 10, or even more such as 20, 50 or even 100;
  organ damage, ischaemic damage and/or microthrombi formation is reduced preferably by at least 10%, 20%, 30%, 40%, or even at least 50%, such as 60%, 70%, 80%, 90% or even to 100%;
  organ damage, ischaemic damage and/or microthrombi formation is reduced by a factor, 2 or more, such as 3, 4, 5, 6, 7, 8, 9, or even 10, or even more such as 20, 50 or even 100;
  organ damage markers, such as LDH levels, troponin T, troponin I levels, and/or creatinine levels, return to at least 40%, or even at least 50%, such as 60%, 70%, 80%, 90% or even to 100% of normal levels;
  organ damage markers, such as LDH levels, troponin T, troponin I levels, and/or creatinine levels, improve by at least 20%, such 30% or even higher, such as 40%, or even at least 50%, such as 60%, 70%, 80%, 90% or even to 100% of normal levels. Preferably, said organ damage, such as LDH levels, troponin T, troponin I levels, and/or creatinine levels, markers improve in less than 30 days of treatment, preferably, in less than 20 days of treatment, such as, less than 15, 10, 9, 8, 7, 6, 5, 4, 3, 2 days or even within 1 day.

the number of platelets is kept at ≥150000/µl.

the risk of exacerbations is reduced by at least 10%, 20%, 30%, 40%, or even at least 50%, such as 60%, 70%, 80%, 90% or even to 100%;

the risk of exacerbations is reduced by a factor, 2 or more, such as 3, 4, 5, 6, 7, 8, 9, or even 10, or even more such as 20, 50 or even 100;

mortality due to said vWF related disease is reduced by 10%, 20%, 30%, preferably by at least 40%, or even at least 50%, such as 60%, 70%, 80%, 90% or even to 100%;

mortality due to said vWF related disease is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100;

refractoriness is reduced preferably by at least 10%, 20%, 30%, 40%, or even at least 50%, such as 60%, 70%, 80%, 90% or even to 100%; and/or refractoriness is reduced by a factor, 2 or more, such as 3, 4, 5, 6, 7, 8, 9, or even 10, or even more such as 20, 50 or even 100.

In an embodiment, the present invention relates to a method as described herein, further comprising measuring the platelet number; and if said platelet number is lower than 150,000/µl, then repeating said step of administering the polypeptide of the invention.

In an embodiment, the present invention relates to a method as described herein, wherein said platelet number of said patient is measured every day, or every 2, 3, 4, 5, 6, 7, 8, 9, or 10 days, preferably at least every week.

In an embodiment, the present invention relates to a method as described herein, wherein said step of administering the polypeptide of the invention is repeated until said platelet number is at least 150,000/µl.

In an embodiment, the present invention relates to a method as described herein, wherein said step of administering the polypeptide of the invention is repeated until said platelet number is at least 150,000/µl on at least 2 consecutive measurements. Preferably, said 2 consecutive measurements are at least 24 h, more preferably 48 h apart, such as at least 3 days apart, or even more such as, 4, 5, 6, or even 7 days apart, preferable a week apart.

In an embodiment, the present invention relates to a method as described herein, wherein said step of administering the polypeptide of the invention is repeated for at least at least 1, 2, 3, 4, 5, 6, 7, 8, 9, or 10 days, or even more than 10 days, such as 20 days, preferably more than 30 days or even more, after said platelet number is at least 150,000/µl on at least 2 consecutive measurements. Preferably, said 2 consecutive measurements are at least 24 h, more preferably 48 h apart, such as at least 3 days apart, or even more such as, 4, 5, 6, or even 7 days apart, preferably a week apart.

In an embodiment, the present invention relates to a method as described herein, further comprising measuring the platelet number of said patient; and if said platelet number ≥150,000/µl, then repeating said step (i) of administering the polypeptide of the invention for at most 30 days, such as at most 20 days, or even 15, 10, 9, 8, 7, 6, 5, 4, 3, 2 days or even 1 day.

In an embodiment, the present invention relates to a method for reducing the risk of and/or preventing an acute episode of a vWF-related disease in a human in need thereof, such as an episode of TTP, e.g. an initial episode and/or recurrent episode of TTP preferably TTP, comprising at least the following steps:

(i) measuring the platelet number of said patient; and (ii) if said platelet number is lower than 150,000/µl, then administering to said human a dose of 5-40 mg, such as 10 mg or 11 mg, of a polypeptide comprising at least one immunoglobulin single variable domain (ISVD) against von Willebrand Factor (vWF);

wherein administration of said polypeptide reduces the risk of and/or prevents an acute episode of a vWF-related disease, such as an episode of TTP, e.g. an initial episode and/or recurrent episode of TTP preferably TTP.

In an embodiment, the present invention relates to a method for treating a TTP episode, e.g. an initial TTP episode and/or recurrent TTP episode in a human in need thereof, preferably TTP, comprising at least the following steps;

(i) administering to said human a first dose of 5-40 mg, preferably 10 mg or 11 mg of a polypeptide comprising at least one immunoglobulin single variable domain (ISVD) against von Willebrand Factor (vWF).

(ii) performing a first Plasma Exchange (PE), preferably within 5 min to 8 h of step (i), preferably within 5 h.

In an embodiment, the present invention relates to a method for treating a TTP episode, e.g. an initial TTP episode and/or recurrent TTP episode, in a human in need thereof, preferably TTP, as described herein, wherein step (i), i.e. administering to said human the polypeptide of the invention, is preceded by performing a preceding PE, preferably within 24 h of step (ii), i.e. performing a first PE.

In an embodiment, the present invention relates to a method for treating a TTP episode, e.g. an initial TTP episode and/or recurrent TTP episode in a human in need thereof, preferably TTP, comprising at least the following steps: (i) performing a Plasma Exchange (PE); (ii) administering to said human a dose of 5-40 mg, preferably 10 mg or 11 mg of a polypeptide comprising at least one immunoglobulin single variable domain (ISVD) against von Willebrand Factor (vWF). Preferably said step (i), i.e. performing a PE, and said step (ii) i.e. administering to said human said polypeptide of the invention, are repeated once or twice per day, for at most for 1, 2, 3, 4, 5, 6, or 7 days.

In an embodiment, the present invention relates to a method for treating a TTP episode, e.g. an initial TTP episode and/or recurrent TTP episode, in a human in need thereof, as described herein, wherein step (ii) i.e. administering to said human said polypeptide of the invention, is performed within 15 min to 4 h of step (i), i.e. performing a PE.

In an embodiment, the present invention relates to a method for treating a TTP episode, e.g. an initial TTP episode and/or recurrent TTP episode, in a human in need thereof, as described herein, further comprising measuring the platelet count of said human, preferably after step (ii) i.e. administering to said human said polypeptide of the invention; and if said platelet count is <150,000/µl, repeating said step (i) i.e. performing a PE, and said step (ii) i.e. administering to said human said polypeptide.

In an embodiment, the present invention relates to a method for treating a TTP episode, e.g. an initial TTP episode and/or recurrent TTP episode, in a human in need thereof, as described herein, further comprising measuring the platelet count of said human [preferably after step (ii) i.e. administering to said human said polypeptide of the invention]; and repeating step (i), i.e. performing a PE, and step (ii) i.e. administering to said human said polypeptide, [once/twice per day] until said platelet number is at least 150,000/µl on at least 2 consecutive measurements. Preferably, said 2 consecutive measurements are at least 24 h, more preferably 48 h apart, such as at least 3 days apart, or even more such as, 4, 5, 6, or even 7 days apart, preferable a week apart.

In an embodiment, the present invention relates to a method for treating a TTP episode, e.g. an initial TTP episode and/or recurrent TTP episode, in a human in need thereof, as described herein, further comprising administering once per day a dose of 5-40 mg, preferably 10 mg or 11 mg of said polypeptide for at least 1-30 days after the platelet count of said human was for the first time ≥150.000/µl.

In an embodiment, the present invention relates to a method for treating a TTP episode, e.g. an initial TTP episode and/or recurrent TTP episode, in a human in need thereof, as described herein, further comprising measuring the ADAMTS13 activity of said human, preferably after step (ii) i.e. administering to said human said polypeptide.

In an embodiment, the present invention relates to a method for treating a TTP episode, e.g. an initial TTP episode and/or recurrent TTP episode6, in a human in need thereof, as described herein, wherein step (i), i.e. performing a PE, and step (ii) i.e. administering to said human said polypeptide of the invention, are repeated until the ADAMTS13 activity is [for the first time] more than 15%, or 20% or even 30% of a reference ADAMTS13 activity.

In an embodiment, the present invention relates to a method for reducing the risk of and/or preventing ischaemic damage, organ damage, refractoriness and/or microthrombi formation [causable by a vWF-related disease, such as, TTP, an episode of TTP, e.g. an initial episode and/or recurrent episode of TTP] in a human in need thereof, comprising at least the following step: (i) administering to said human a dose of 5-40 mg/day, preferably 10 mg/day or 11 mg/day of a polypeptide comprising at least one ISVD against vWF; wherein administration of said polypeptide reduces the risk of and/or prevents ischaemic damage, organ damage, refractoriness and/or microthrombi formation by 10%, 20%, 30%, preferably by at least 40%, or even at least 50%, such as 60%, 70%, 80%, 90% or even to 100%. Preferably, administration of said polypeptide reduces the risk of and/or prevents ischaemic damage, organ damage, refractoriness and/or microthrombi formation by a factor 1.2, 1.3, 1.4, 1.5, 1.6, 1.75, 1.8, 2 or more, such as 3, 4, 5, 6, 7, 8, 9, or even 10, or even more such as 20, 50 or even 100.

In an embodiment, the present invention relates to a method wherein said step of administering said polypeptide is repeated for at least 1, 2, 3, 4, 5, 6, 7 days, or even longer such as 1 week, 2 weeks, 3 weeks, or even longer such as 1 month or even 2 months In an embodiment, the present invention relates to a method further comprising measuring ADAMTS13 activity of said patient, preferably once per week.

In an embodiment, the present invention relates to a method wherein said step of administering said polypeptide is repeated for at least 1, 2, 3, 4, 5, 6, 7 days, or even longer such as 1 week, 2 weeks, 3 weeks, or even longer such as 1 month or even 2 months when the ADAMTS13 activity is [for the first time]≥10%, such as more than 15%, or even more than 20% of a reference ADAMTS13 activity.

In an embodiment, the present invention relates to a method of treating a symptom of a vWF-related disease, such as TTP, in a human suffering from said disease, comprising administering to the subject a polypeptide of the invention, in an amount effective to treat the symptom of a vWF-related disease in a human suffering from said disease.

In an embodiment, the present invention relates to a method of inhibiting in a human the onset or progression of a vWF-related disease, such as TTP, the inhibition of which is effected by binding of a polypeptide comprising at least one immunoglobulin single variable domain (ISVD) against von Willebrand Factor (vWF) to vWF, comprising administering to the human at a predefined interval effective inhibitory doses of said polypeptide, wherein each administration of the polypeptide delivers to the human from 0.1 mg per kg to 25 mg per kg of the human's body weight, preferably 10 mg or 11 mg of said polypeptide if said human has body weight ≥40 kg, and 5 mg if said body weight is <40 kg, so as to thereby inhibit the onset or progression of the disease in the human.

In an embodiment, the present invention relates to a method of reducing the likelihood of a human contracting ischaemic organ damage by a vWF-related disease, which comprises administering to the human at a predefined dose a polypeptide comprising at least one immunoglobulin single variable domain (ISVD) against von Willebrand Factor (vWF), wherein each administration of the antibody delivers to the human from 0.1 mg per kg to 25 mg per kg of the human's body weight, preferably 10 mg or 11 mg of said polypeptide if said human has body weight ≥40 kg, and 5 mg if said body weight is <40 kg, so as to thereby reduce the likelihood of the human contracting ischaemic organ damage.

4. DETAILED DESCRIPTION

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Scully et al. 2017, supra, and Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins. Unless indicated otherwise, all terms that are not specifically defined in detail herein are known in the relevant field and will be clear to the skilled person; as well as for instance Scully et al. 2017, supra, describing the consensus on the standardization of terminology in TTP and related thrombotic microangiopathies.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The therapeutic potential of the polypeptides of the invention, in particular ALX 0081, in a TTP setting was further evaluated and demonstrated in a phase III (Hercules) study.

It was demonstrated that patients with an initial aTTP episode have a delayed presentation and more severe disease at baseline than those with recurrent disease episodes. Even in this more serious disease setting it was shown that treatment with caplacizumab improved the outcome (Example 7.11). In particular, it was demonstrated that the polypeptides of the invention, such as ALX 0081 and ALX 0081-A, improved outcomes, including faster time to platelet count response, lower proportion of patients with either death, recurrence or a major TE event during the treatment period, lower recurrence rate during the overall treatment period, and prevention of refractoriness compared to placebo.

TTP is an acute disease with recurrent bouts or outbreaks, i.e. an individual recurrent disease event, requiring immediate treatment for each episode. As used herein, an "initial episode of TTP" (also indicated as "initial TTP episode"), is the first time that a subject presents a bout or outbreak of TTP. As used herein a "recurrent episode of TTP" (also indicated as "recurrent TTP episode"), is any bout of TTP following an initial TTP episode.

The present invention is also at least partly based on the finding that through rapid blocking of vWF-mediated platelet adhesion by the polypeptides of the invention, such as ALX 0081 or ALX 0081-A, a novel treatment option for aTTP is provided. In particular, treatment with caplacizumab resulted in improved treatment outcomes as reflected by meaningful reductions in healthcare resource utilization, including PE days, duration of hospitalization and days spent in ICU (Example 7.12).

It was further demonstrated that administration of polypeptides according to the invention, comprising at least one ISVD binding vWF, such as ALX 0081 or ALX 0081-A, was efficacious in patients who experienced an exacerbation of aTTP (Example 7.13).

In addition, it was demonstrated that administration of polypeptides according to the invention, comprising at least one ISVD binding vWF, such as ALX 0081 or ALX 0081-A, was efficacious in patients in reducing refractoriness.

Although the current therapy of TTP with PE and transfusion has significantly reduced the mortality rates from TTP, it was shown that frontline therapy of administering the polypeptides according to the invention, comprising at least one ISVD binding vWF, such as ALX 0081 or ALX 0081-A, was exceptionally advantageous. For instance, valuable time can be gained when using caplacizumab as frontline therapy.

Hence, the invention provides an unexpectedly sustained and prolonged effect, reduced exacerbations, reduced hospitalization, reduced morbidity, a reduced number of required PEs, reduced ischaemia, reduced refractoriness, reduced organ damage and/or reduced death toll, even in the more severe disease setting of initial TTP episodes.

Therefore, the invention relates to the use of the polypeptides of the invention to treat or ameliorate a vWF-related disease in a patient, such as TTP, by an unexpectedly large decrease in the time-to-response, demonstrated by an accelerated platelet recovery. The invention also provides for less frequent PEs, while still maintaining the platelet recovery in the human patient at unexpectedly prolonged periods of time. Accordingly, methods are provided for decreasing the time-to-response in a human patient by administering to the patient a polypeptide of the invention, wherein the amount of the polypeptide administered is effective to change one or more disease markers of TTP, such as the number of platelets, thrombocytopenia, neurocognitive function, ADAMTS13 levels and anti-ADAMTS13 antibody titres, ADAMTS13 activity levels, cardiac marker (Troponin T (TnT or cTnT) or Troponin I (TnI or cTnI)), BNP (brain natriuretic peptide) or N-terminal pro brain natriuretic peptide (NT proBNP), and Brain damage markers (such as NSE (neuron specific enolase) and Sβ100 (S100beta)), preferentially an increase in the number of platelets.

In addition, the polypeptide of the invention when administered to a human TTP patient was safe as examined by safety laboratory markers, such as RICO, vWF and FVIII chromogene. Although there was a potential for an increased bleeding risk, this was wholly manageable.

The markers can be measured using standard methods known to and used by the skilled person, such as various immunologically based assays, including enzyme-linked immunosorbent assays (ELISA; also known as an enzyme immunoassay (EIA)), radioimmunoassays or immunoenzymetric assays. Chemical, colorimetric and enzymatic based assays also may be used when suitable.

Accordingly the present invention provides a polypeptide comprising at least one ISVD against vWF, preferably ALX 0081 or ALX 0081-A, for use in treating a vWF-related disease in a human in need thereof, such as TTP, by administering to the human a 5-40 mg dose of said polypeptide repeatedly, wherein said dose is followed within 15 min to 4 h by a first PE.

The polypeptides of the invention were administered as adjunctive treatment at specific times relative to the PE procedures to treat or prevent (e.g., reduce or ameliorate one or more symptoms associated with) a vWF-related disease, e.g., TTP.

The term "treating" (treating, treatment) refers to administering a therapy in an amount, manner, and/or mode effective to improve a condition, symptom, or parameter associated with a disease or to prevent progression of a disease, to either a statistically significant degree or to a degree detectable to one skilled in the art. In the case of therapeutic use, the treatment may improve, cure, maintain, or decrease duration of, the disease or condition in the subject. In therapeutic uses, the subject may have a partial or full manifestation of the symptoms. In a typical case, treatment improves the disease or condition of the subject to an extent detectable by a physician, or prevents worsening of the disease or condition. For instance, the clinical features and signs in an acute episode of TTP as depicted in Table 1 or as provided in the TTP treatment guidelines (Scully et al. 2012 supra) improve. For instance, due to the treatment, the platelet count normalizes, the ADAMTS13 autoantibody titre decreases and/or the ADAMTS13 activity increases, all as known in the art and/or further detailed herein (cf. infra).

An effective amount, manner, or mode can vary depending on the subject and may be tailored to the subject.

The term "treatment period" refers to the interval of time when a patient is treated, which may include PE and/or administration of the polypeptide of the invention, and optionally other medicaments such as, for instance, steroids or rituximab. In a preferred embodiment, treatment period refers to the administration of the polypeptide of the invention to a patient in need thereof, wherein said administration is repeated for at least 1, 2, 3, 4, 5, 6, 7, 8, 9, or 10 days, or even more than 10 days, such as 20 days, preferably more than 30 days, such as 2 months, 3 months, 4 months, months, 6 months or even more.

As used herein, the term "preventing" means to mitigate a symptom of the referenced disorder. In particular, said term encompasses the complete range of therapeutically positive effects of administrating a polypeptide of the invention to a subject including reduction of, alleviation of, and relief from, a vWF related disorder, e.g. TTP, and symptoms thereof. The term "prevention" includes the prevention or postponement of development of the disease, prevention or postponement of development of symptoms and/or a reduction in the severity of such symptoms that will or are expected to develop. These further include ameliorating existing symptoms, preventing additional symptoms and ameliorating or preventing the underlying causes of symptoms.

As used herein, the terms "subject" and "patient" are used interchangeably. As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgus monkey, gorilla chimpanzee and a human). A "patient" preferably refers to a human. Said patient can include elderly, adults, adolescents and children, from any age, for instance children ranging from the age of 2 years to less than 12 years, adolescents ranging from 12 years to less than 18 years, adults ranging from 18 years to less than 65 years, and elderly from 65 years and up.

Non-limiting examples of vWF-related diseases that can be treated include, but are not limited to, e.g. acute coronary syndrome (ACS), transient cerebral ischemic attack, unstable or stable angina pectoris, stroke, myocardial infarction, thrombotic thrombocytopenic purpura (TTP) and Upshaw-Schulman syndrome, preferably TTP.

The PE procedures to treat or prevent a vWF-related disease, such as e.g., TTP have been described in the consensus and guidelines on the diagnosis and management of TTP and other thrombotic microangiopathies (Scully et al. 2017 supra), which is explicitly incorporated herein by reference. Complete remission is defined as normal platelet count, i.e. ≥150,000/μl, and optionally the absence of exacerbations (cf. Scully et al. 2012, 2017, supra).

As used herein the "time-to-response" is the time between the first treatment of a patient having an acute episode of TTP, e.g. an initial episode and/or recurrent episode of TTP and a platelet count of ≥150,000/μl, in which the first treatment is a PE or the administration of a polypeptide of the invention, or both, whichever is the earliest.

As used herein, the term "refractoriness" or "refractory" refers a persistent thrombocytopenia, lack of sustained platelet count increment or platelet counts of <50*10$^9$ L$^{-1}$ and a persistently raised LDH level (>1.5 ULN) despite 5 PEs and steroid treatment, including subjects failing to achieve remission or whose platelet count and LDH level improve but worsen despite ongoing treatment The term "Plasma exchange" ("PE" or "PEX") refers to a therapeutic procedure used to treat a variety of diseases, including TTP, through the bulk removal of plasma, i.e. a procedure in which a large volume of plasma is removed, usually 1-1.5 plasma volumes, which is replaced with a replacement fluid (Winters 2012 Hematology ASH Education Book 1:7-12). Through the bulk removal and replacement of plasma, PE removes pathologic substances such as auto-antibodies against ADAMTS13 and ULvWF, but also some platelets. Plasma is used as a replacement fluid to replace ADAMTS13 when treating TTP (McLeod Best Pract Res Clin Haematol. 2006; 19:157-167). The bulk removal and replacement of plasma also has implications for laboratory testing, making patient testing intricate.

Because PE involves the bulk removal of plasma, anything circulating in the plasma will be removed. Hence, this procedure is nonselective, removing both normal and pathologic plasma components, but also any medicaments to treat TTP administered before PE.

Notwithstanding the benefits of PE in treating TTP, in the present invention it was shown that caplacizumab is beneficial when started as frontline therapy. The term "frontline" therapy (or frontline treatment) refers to the first treatment (also known as "first-line" treatment) given for a disease, e.g. TTP. Next to the frontline therapy, additional treatment may be added or used instead, such as PE and adjunctive immunosuppressive treatment (e.g. corticosteroids such as (methyl)-prednisolone or (methyl)-prednisone; or rituximab), antiplatelet agents (e.g. aspirin), supportive therapy with red cell transfusion or folate supplementation, treatment with vincristine or cyclosporin, anti-autoADAMTS13 antibodies, or ADAMTS13.

The person skilled in the art is well acquainted in determining the number of platelets. Platelet counts can be done by any method known in the art, such as manually using a hemocytometer or with an automated analyzer, e.g. electronic counting. Counts can also be estimated during blood smear examination. The microscopic method uses a phase contrast microscope to view blood on a hemacytometer slide. Electronic counting of platelets is the most common method. There are two types of electronic counting, voltage-pulse and electro-optical counting systems. For instance, the ADVIA® hematology analyzer can be used for obtaining platelet counts and verify the obtained count by estimating counts on a Wright's-stained blood smear. The ADVIA measures platelets by flow cytometry based on principles of light scattering. For instance, platelets are identified by their size (<30 FL, low angle light scatter) and refractive index (n=1.35 to n=1.40 or high angle light scatter).

In various patients following an acute episode of TTP, e.g. an initial TTP episode and/or recurrent TTP episode(s), the polypeptide of invention comprising at least one ISVD against vWF, e.g. ALX 0081 or ALX 0081-A, was administered after said patient had received a PE ("preceding PE"; a PE preceding the administration of the first dose of the polypeptide of the invention).

Accordingly, the present invention relates to performing a PE (preceding PE) to a patient in need thereof, e.g. a patient with an acute episode of TTP, e.g. an initial TTP episode and/or recurrent TTP episodes, followed by a next PE within 24 h of said preceding PE, and administering a polypeptide of the invention ("first dose") about 8 h, 7 h, 6 h, 5 h, 4 h, 3 h, 3 h, 1 h, 45 min, 30 min, 20 min, 15 min, 10 min or even 5 min before starting said next PE, such as from 6 h to 15 min before starting said next PE (the "first PE"). In the present invention, the term "first dose" means the first administration of a polypeptide of the invention to a patient in need thereof, e.g. after an acute episode of TTP, e.g. an initial TTP episode and/or recurrent TTP episode(s).

In an embodiment, an administration of the polypeptide of the invention to a patient, preferably a first dose is followed within 5 min to 8 h, such within 10 min to 6 h or 15 min to 4 h, for instance within 8 h, 7 h, 6 h, 5 h, 4 h, 3 h, 3 h, 1 h, 45 min, 30 min, 20 min, 15 min, 10 min or even 5 min by a PE.

In the present invention, the term "first PE" means the first PE performed after (or in some cases concurrent with) administration to a patient of a first dose of the polypeptide of the invention.

The polypeptide of the invention can be administered or used for administration in the form of a liquid solution (e.g., injectable and infusible solutions). Such compositions can be administered by a parenteral mode (e.g., subcutaneous, intraperitoneal, or intramuscular injection), or by inhalation. The phrases "parenteral administration" and "administered parenterally" as used herein mean modes of administration other than enteral and topical administration, usually by injection, and include, subcutaneous (s.c.) or intramuscular administration, as well as intravenous (i.v.), intra-capsular, intraorbital, intracardiac, intradermal, intraperitoneal, transtracheal, subcuticular, subcapsular, subarachnoid, intraspinal, epidural and intrastemal injection and infusion. Preferably the second or further doses of the polypeptides of the invention described herein are administered subcutaneously.

Preferably, the administration of the first dose of a polypeptide of the invention following an acute acute episode of TTP, e.g. an initial TTP episode and/or recurrent TTP episode(s) is an intravenous bolus injection, e.g. delivering the polypeptide through an intravenous line, administered all at once, over a period of a minute or two. Even more preferably, the administration of the first dose of a polypeptide of the invention following an acute episode of TTP, e.g. an initial TTP episode and/or recurrent TTP episode(s) is an intravenous push injection, e.g. delivering the polypeptide through an intravenous line, administered all at once, over a period of about 30 seconds or less.

The inventors considering that the polypeptide of the invention is safe to use as was demonstrated in previous studies in healthy volunteers and the present study with TTP patients (cf. Examples), that TTP might be hard to diagnose, especially an initial TTP episode, and that any time lost before starting a treatment results in adversities, concluded that this finding has the benefit that a treatment with the polypeptide of the invention can already be started timely, even before the patient enters a hospital, such as e.g. in an ambulance. Preferably, the polypeptide of the invention such as ALX 0081 or ALX 0081-A is administered by an intravenous push injection, since this can easily be performed outside hospitals, thus saving valuable time.

Accordingly, the present invention relates to administering to a patient in need thereof, such as e.g. patients with acute episodes (acute bouts) of TTP, e.g. an initial TTP episode and/or recurrent TTP episode(s), a polypeptide of the invention about 8 h, 7 h, 6 h, 5 h, 4 h, 3 h, 3 h, 1 h, 45 min, 30 min, 20 min, 15 min, 10 min or even 5 min before starting PE, such as from 6 h to 15 min before starting PE ("first dose").

In an embodiment, the administration of a first dose of a polypeptide of the invention following an acute episode of TTP, e.g. an initial TTP episode and/or recurrent TTP episode(s) is followed by a PE ("first PE"). This first PE, whether or not preceded by a preceding PE, is followed by administration of a second or further dose of the polypeptide of the invention ("second dose" or "further dose"). Preferably, the second dose or further dose is administered within 120, 90 or 60 min, such as within 1-60 min, for instance, within 50, 45, 40, 35, 30, 25, 20, 15, 10, 5, 4, 3, 2 or even 1 min after the first PE. In some cases, it may be advantageous to administer the second or further dose together or concurrently with the replacement fluid, e.g. the plasma of the PE.

In additional embodiments, a first dose, a second dose or further dose of the polypeptide of the invention is about 1, 2, 3, 4, 5, 6, 7, 8, 9, 10, 11, 12, 13, 14, 15, 16, 17, 18, 19, 20, 25, 30, 35, or 40, 50, 60, 70 or 80 mg, preferably 5-40 mg even more preferably 10 mg or 11 mg, which can be administered to a patient in need thereof, preferably per day. For administration to juvenile patients, such as e.g. children and adolescents, the dose may be adjusted to the weight of the patient. In particular embodiments, the dose is about 0.01, 0.025, 0.05, 0.075, 0.1, 0.12, 0.14, 0.15, 0.16, 1.08, 0.2, 0.22, 0.24 or 0.25 mg/kg, preferably 0.143 mg/kg which corresponds to a 10 mg dose in a 70 kg adult. In other embodiments the dose is about 5 mg if the body weight of said child or adolescent is <40 kg.

In an embodiment, the present invention relates to the administration of about 5 to 40 mg, preferably 10 mg or 11 mg of a polypeptide of the invention, e.g. ALX 0081 or ALX 0081-A, within 1-60 min after a PE procedure, e.g. the first PE, the second PE or a further PE.

In an embodiment, the polypeptide of the invention, e.g. ALX 0081 or ALX 0081-A, is administered once per day or twice per day to a TTP patient in need thereof, preferably a patient with a platelet count below 100,000/μl plasma and/or a patient with an ADAMTS13 activity of ≤10% such as ≤5%.

In a further embodiment, a TTP patient in need thereof is treated with (i) PE; and (ii) a dose of 5-40 mg preferably 10 mg or 11 mg of said polypeptide 60 min to 1 min after said PE of step (i), wherein step (i) and step (ii) are repeated once or twice per day until the platelet count of said patient is at least 50,000/μl plasma, such as 75,000, 100,000, 125,000 or even 150,000 per μl plasma.

In some cases it may be advantageous to repeat step (i) and step (ii) for a minimum of two days after complete remission (a platelet count of ≥150,000/μl plasma).

In an embodiment, 5-40 mg of the polypeptide of the invention is administered daily or twice daily for at least 5, 10, 15, 20, 25, 30, 60, 90 or even 120 days after the platelet count of said patient is ≥150.000/μl plasma, particularly when the ADAMTS13 activity of said patient is ≤10% such as ≤5%, or after the last PE.

Hence, the administration of polypeptides comprising at least one ISVD against vWF, such as ALX 0081 or ALX 0081-A, to human TTP patients following an acute episode of TTP, e.g. an initial TTP episode and/or recurrent TTP episode(s) provides an unexpected decrease in the time-to-response, independent of the order of administration of said polypeptide and said PE, e.g. whether the PE is performed before or after the administration of the first dose of the polypeptide of the invention.

It was further surprisingly found that the number of exacerbations decreased during the double-blind (DB) treatment period, when patients were switched to open label ("OL") caplacizumab, together with re-initiation of daily plasma exchange (PEX) and immunosuppression, while maintaining the blind for the initial treatment allocation (cf. Example 7.13).

The term "exacerbation" as used herein refers to a recurrent thrombocytopenia following a confirmed platelet response and requiring a re-initiation of daily PE treatment after ≥1 day but ≤30 days after the last daily PE.

This indicates that the polypeptide of the invention, such as ALX 0081 or ALX 0081-A, can be solely responsible for treating and/or alleviating (the symptoms of) TTP.

Accordingly, the present invention relates to a polypeptide comprising at least one ISVD against vWF, such as ALX 0081 or ALX 0081-A, for use in treating a vWF-related disease, such as TTP, in a human in need thereof, by administering to the human a dose of 1-80 mg or 5-40 mg, such as 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably 10 mg or 11 mg of said polypeptide if said human has body weight ≥40 kg, and 5 mg if said body weight is <40 kg.

Based on the surprising observations herein, a further optimized treatment protocol was designed by the present inventors, in essence based on the idea that the distribution of confirmed platelet response time is shorter and not skewed and biased to the right (longer time to response) in the CAP (caplacizumab) arm in comparison to the placebo arm. In the further optimized treatment protocol, all subjects are treated with a fixed PE treatment period, which is set for 3-5 days, such as 3 days or 4 days or 5 days, preferably 3 days. In this case, the PE treatment period can be independent of the recovery of platelets (≥150,000/µl). In the further optimized treatment protocol, the burden for the patient and the costs are decreased.

Accordingly, the present invention relates to a polypeptide comprising at least one ISVD against vWF, such as ALX 0081 or ALX 0081-A, for use in treating a vWF-related disease in a human in need thereof, comprising: (i) performing a PE; and (ii) administering a dose of 5-40 mg, such as 10 mg or 11 mg of the polypeptide of the invention 15 min to 4 h after said PE of step (i), wherein step (i) and step (ii) are repeated once per day for 3-5 days, such as 3 days, 4 days or 5 days, preferably 3 days; followed by further comprising administering once per day a dose of 5-40 mg, such as 10 mg or 11 mg of said polypeptide for at least 10 days, such as at least 20 days or at least 30 days and/or for at least 10 days, such as at least 20 days or at least 30 days after the platelet count of said patient was for the first time ≥150.000/µl.

In the present study, for up to one year TTP patients have been followed-up for remission. The term "remission" as used herein refers to as confirmed platelet response and the absence of exacerbation. The term "confirmed platelet response" as used herein refers to the time-to-response of treatment as defined by a recovery of platelets ≥150,000/µL, which response must be confirmed at 48 hours after the initial reporting of platelet recovery above 150,000/µL by a de novo measure of platelets ≥150,000/µL, and preferably LDH≤2×ULN.

As noted above, the platelet count is the primary means for assessing remission. Measurement of ADAMTS13 activity in patients with a history of classical TTP is important because low levels have been shown to be predictive of relapse. However, it is unclear at present (and the data is conflicting) as to whether the titre of an inhibitory antibody to ADAMTS13 is significant i.e. are those individuals with a high titre anti-ADAMTS13 antibody more likely to relapse than those with a low titre. The person skilled in the art appreciates that current tests of ADAMTS13 are performed under static conditions and do not always accurately reflect the physiological changes that occur in vivo (http://practical-haemostasis.com/Miscellaneous/Miscellaneous%20Tests/adamts13_assays.html).

Remission appears more pronounced for the subgroup of subjects with low baseline ADAMTS13 activity (i.e. less than 10%, such as less than 5%), when starting treatment, e.g. administering the first dose, of the polypeptide of the invention, such as ALX 0081 or ALX 0081-A.

Accordingly, the present invention relates to a polypeptide comprising at least one ISVD against vWF for use in treating a vWF-related disease in a human in need thereof, by administering to said human a first dose of 1-40 mg, preferably 10 mg or 11 mg of said polypeptide, until the platelet count of said human is ≥150000/µl. In a preferred aspect, said human has an ADAMTS13 activity of less than 10%, such as less than 5% when administering said polypeptide.

The term "relapse" as used herein refers to a de novo event of TTP that occurs later than 30 days after the last daily PE.

ADAMTS13 activity is predictive marker for recurrences of TTP and its potential for treatment decisions. ADAMTS13 activity is able to predict relapses which occur shortly after stopping caplacizumab treatment. These relapses are considered as relapses of the presenting TTP episode (unresolved disease activity, based on continuously low ADAMTS13 activity). A 30-day treatment period (post PE) with caplacizumab has demonstrated to have a significant impact on the number of exacerbations. Hence, extending the caplacizumab treatment period for those patients at risk for relapse (i.e. with underlying disease activity based on ADAMTS13 activity) will maintain the protective effects of caplacizumab until the underlying disease is adequately treated and resolved. Conversely, precautionary treatment with caplacizumab will reduce the risk of a-new-acute episode of TTP.

Hence, treatment with polypeptide of the invention, such as ALX 0081 or ALX 0081-A, should be continued for longer periods compared to patients with higher ADAMTS13 activity. The polypeptide of the invention should be administered to a TTP patient to reduce the risk of and/or prevent the chance of relapse(s) until the ADAMTS13 activity was at least 10%, such at least 15%, 20%, 25%, 30%, 35%, 40%, 45%, or even 50% compared to the normal or reference activity.

Accordingly, the present invention relates to a polypeptide comprising at least one ISVD against vWF for use in reducing the risk of and/or preventing an acute episode of TTP, e.g. an initial TTP episode and/or recurrent TTP episode(s) in a human in need thereof, comprising a step (i): administering to said human a dose of 5-40 mg, preferably 10 mg or 11 mg, of said polypeptide. Preferably, said risk is reduced by a factor of at least 1.2, 1.3, 1.4, 1.5, 1.6, 1.75, 1.8, 2 or more, such as 3, 4, 5, 6, 7, 8, 9, or even 10, or even more such as 20, 50 or even 100. Preferably said risk is reduced by 10% or even more such as 20%, 30%, 40%, 50%, 60% or more, such as 80% or even 100%.

Accordingly, the present invention relates to a polypeptide as described herein, for use in treating and/or preventing a vWF-related disease in a human in need thereof as described herein, wherein said step of administering to said human said polypeptide is repeated for at least 1, 2, 3, 4, 5, 6, 7, 8, 9, or 10 times, or even more than 10 times, such as 20 times, preferably more than 30 times or even more.

Accordingly, the present invention relates to a polypeptide as described herein, for use in treating and/or preventing a vWF-related disease in a human in need thereof as described herein, wherein said step of administering to said human said polypeptide is repeated for at least 1, 2, 3, 4, 5, 6, 7, 8, 9, or 10 days, or even more than 10 days, such as 20 days, preferably more than 30 days, such as 2 months, 3 months, 4 months, 5 months, 6 months or even more.

Accordingly, the present invention relates to a polypeptide as described herein, for use in treating and/or preventing a vWF-related disease in a human in need thereof as described herein, wherein said dose is administered 1 time per day or two times per day.

Accordingly, the present invention relates to a polypeptide as described herein, for use in treating and/or preventing a vWF-related disease in a human in need thereof as described herein, further comprising
 (ii) comparing the ADAMTS13 activity with a reference ADAMTS13 activity; and
 (iii) if said ADAMTS13 activity is lower than 30%, such as 20%, 15%, 10% or 5% of said reference ADAMTS13 activity, then repeating said step (i) of administering to said human said polypeptide.

Accordingly, the present invention relates to a polypeptide as described herein, for use in treating and/or preventing a vWF-related disease in a human in need thereof as described herein, wherein said ADAMTS13 activity of said patient is measured and/or compared every day, or every 2, 3, 4, 5, 6, 7, 8, 9, or 10 days, preferably at least once every week.

Accordingly, the present invention relates to a polypeptide as described herein, for use in treating and/or preventing a vWF-related disease in a human in need thereof as described herein, wherein step of administering the polypeptide of the invention to said human is repeated until said ADAMTS13 activity is at least 5%, 10%, 15%, such 20%, or even 30% or higher of said reference ADAMTS13 activity.

Accordingly, the present invention relates to a polypeptide comprising two anti-human von Willebrand Factor (vWF) immunoglobulin single variable domains (ISVDs) for use in treating (the symptoms of) an exacerbation of a vWF-related disease in a human, comprising administering to said human a dose of 1-80 mg, preferably 5-40 mg, even more preferably 10 mg or 11 mg of said polypeptide, 1 time per day or 2 times per day, until an ADAMTS13 activity is higher than 10% of a reference ADAMTS13 activity; optionally repeating said administration step until said ADAMTS13 activity is higher than 10% of a reference ADAMTS13 activity for at least 2 days, such as at least 5 days, 7 days or even longer, such as 14 days, 21 days or even at least 1 month.

Accordingly, the present invention relates to a polypeptide comprising two anti-human von Willebrand Factor (vWF) immunoglobulin single variable domains (ISVDs) for use in treating (the symptoms of) a relapse of a vWF-related disease in a human, comprising administering to said human a dose of 1-80 mg, preferably 5-40 mg, even more preferably 10 mg or 11 mg of said polypeptide, 1 time per day or 2 times per day, until an ADAMTS13 activity is higher than 10% of a reference ADAMTS13 activity; optionally repeating said administration step until said ADAMTS13 activity is higher than 10% of a reference ADAMTS13 activity for at least 2 days, such as at least 5 days, 7 days or even longer, such as 14 days, 21 days or even at least 1 month.

Accordingly, the present invention relates to a polypeptide as described herein, for use in treating and/or preventing a vWF-related disease in a human in need thereof as described herein, wherein step of administering to said human said polypeptide is repeated until said ADAMTS13 activity is at least 5%, 10%, 15%, such as 20% or 30% of said reference ADAMTS13 activity on at least 2 consecutive measurements. Preferably, said 2 consecutive measurements are at least 24 h, more preferably 48 h apart, such as at least 3 days apart, or even more such as, 4, 5, 6, or even 7 days apart, preferably a week apart.

Accordingly, the present invention relates to a polypeptide as described herein, for use in treating and/or preventing a vWF-related disease in a human in need thereof as described herein, wherein said step of administering to said human said polypeptide is repeated for at least at least 1, 2, 3, 4, 5, 6, 7, 8, 9, or 10 days, or even more than 10 days, such as 20 days, preferably more than 30 days or even more, after said ADAMTS13 activity is at least 5%, at least 10%, at least 15%, such as 20% or at least 30% of said reference activity on at least 2 consecutive measurements.

Accordingly, the present invention relates to a polypeptide comprising at least one ISVD against vWF for use in reducing the risk of and/or preventing an acute episode of TTP, e.g. an initial TTP episode and/or recurrent TTP episode(s), in a human in need thereof, comprising step (i): administering to said human a dose of 5-40 mg, preferably 10 mg or 11 mg of said polypeptide, further comprising
 measuring the ADAMTS13 activity of said patient;
 comparing said ADAMTS13 activity with a reference ADAMTS13 activity; and
 if said ADAMTS13 activity is ≥5%, such as ≥10%, or even ≥15%, or more than 20% or 30% of said reference ADAMTS13 activity, then repeating said step (i) for at most 30 days, such as at most 20 days, or even 15, 10, 9, 8, 7, 6, 5, 4, 3, 2 days or even 1 day.

Accordingly, the present invention relates to a polypeptide comprising at least one ISVD against vWF for use in reducing the risk of and/or preventing an acute episode of TTP, e.g. an initial TTP episode and/or recurrent TTP episode(s), in a human in need thereof, comprising at least the following steps:
 (i) optionally measuring the ADAMTS13 activity of said patient;
 (ii) optionally comparing said ADAMTS13 activity with a reference ADAMTS13 activity; and
 (iii) if said ADAMTS13 activity is lower than 30%, 20%, 15%, 10% or 5% of said reference activity, then administering to said human a dose of 5-40 mg, preferably 10 mg or 11 mg of said polypeptide comprising at least one ISVD against vWF.

As used herein, reducing risk or incidence includes decreasing the probability or incidence of an indication, a symptom or result of vWF-related disease, such as TTP, for a subject compared to a relevant, e.g. untreated, control population, or in the same subject prior to treatment according to the invention.

An indication, a symptom or result of a vWF-related disease, such as TTP, as used herein includes any one of organ damage, ischaemic damage, microthrombi formation, exacerbations, mortality, relapses, refractoriness, one or more disease markers of a vWF related disease, such as TTP, include the number of platelets, thrombocytopenia, neurocognitive function, ADAMTS13 levels and anti-ADAMTS13 antibody titres, ADAMTS13 activity levels, cardiac marker (Troponin T or Troponin I), BNP (brain natriuretic peptide) or N-terminal pro brain natriuretic peptide (NT proBNP), creatinine, and Brain damage markers (such as NSE (neuron specific enolase) and Sβ100 (S100beta)), preferentially organ damage markers, such as LDH levels, troponin T and/or troponin I levels, and/or creatinine levels.

The reduced risk or incidence can include delaying or preventing the onset of an indication, a symptom or result of vWF-related disease, such as TTP. Risk or incidence can also be reduced if the severity of an indication, a symptom or result of vWF-related disease, such as TTP, is reduced to a level such that it is not of clinical relevance. That is, the indication, a symptom or result of a vWF-related disease, such as TTP, may be present but at a level that does not endanger the life, activities, and/or wellbeing of the subject. In some circumstances the occurrence of the vWF-related disease, such as TTP, is reduced to the extent that the subject does not present any signs of the vWF-related disease, such as TTP, during and/or after the treatment period.

It will be appreciated that no actual proof of reduced risk for an individual can be obtained because if treatment is provided then it cannot be said whether an indication, symptom or result of a vWF-related disease, such as TTP, would have occurred, or would have occurred sooner in the absence of such treatment. Thus, the concept of risk and, increased or reduced risk refer to statistical values only. Further, reduction of risk of an indication, symptom or result of a vWF-related disease, such as TTP, can be reflected in a reduction in the severity of an indication, a symptom or result of a vWF-related disease, such as TTP, as well as in the absence of observation or delay in observation of an indication, a symptom or result of a vWF-related disease, such as TTP.

It will be appreciated that the polypeptide of the invention reduces the risk of and/or preventing an acute episode of TTP, e.g. an initial TTP episode and/or recurrent TTP episode(s). Hence, an indication, a symptom or result of an acute episode of TTP, e.g. an initial TTP episode and/or recurrent TTP episode(s), is also reduced. Given the pathophysiology of acquired TTP whereby ULvWF strings consume platelets in the formation of microthrombi, it was reasoned that the recovery of platelet counts is an indirect measure of prevention of further microthrombi formation. The morbidity and the acute mortality associated with acquired TTP is a result of these microthrombi.

Indeed, this reasoning is supported by the normalization of organ damage markers. In particular, the results indicate that the organ damage markers, such as troponin I and T, LDH and creatinine, return faster to normal levels in subjects receiving the polypeptide of the invention, e.g. ALX 0081 or ALX 0081-A, than in subjects receiving placebo (cf. Examples).

Hence, the results suggest that a faster normalization rate of these organ damage markers is linked to a better clinical outcome, i.e. a reduced risk of and less organ damage due to organ ischemia caused by microthrombi, and reduced refractoriness.

Accordingly, the present invention relates to a method as described herein, wherein
  the risk of organ damage, ischaemic damage and/or microthrombi formation is reduced by 10%, 20%, 30%, preferably by at least 40%, or even at least 50%, such as 60%, 70%, 80%, 90% or even to 100% (e.g. absence of organ damage, ischaemic damage and/or microthrombi formation due to the vWF-related disease);
  the risk of organ damage, ischaemic damage and/or microthrombi formation is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100;
  organ damage, ischaemic damage and/or microthrombi formation is reduced preferably by at least 10%, 20%, 30%, 40%, or even at least 50%, such as 60%, 70%, 80%, 90% or even to 100%;
  organ damage, ischaemic damage and/or microthrombi formation is reduced by a factor 1.2, 1.3, 1.4, 1.5, 1.6, 1.75, 1.8, 2 or more, such as 3, 4, 5, 6, 7, 8, 9, or even 10, or even more such as 20, 50 or even 100;
  organ damage markers, such as LDH levels, troponin T, troponin I levels, and/or creatinine levels, return to at least 40%, or even at least 50%, such as 60%, 70%, 80%, 90% or even to 100% of normal levels;
  organ damage markers, such as LDH levels, troponin T, troponin I levels, and/or creatinine levels, improve by at least 20%, such 30% or even higher, such as 40%, or even at least 50%, such as 60%, 70%, 80%, 90% or even to 100% of normal levels. Preferably, said organ damage, such as LDH levels, troponin T, troponin I levels, and/or creatinine levels, markers improve in less than 30 days of treatment, preferably, in less than 20 days of treatment, such as, less than 15, 10, 9, 8, 7, 6, 5, 4, 3, 2 days or even within 1 day.
  the number of platelets is kept at ≥150000/µl.
  the time to platelet normalization (≥150000/µl) is reduced by at least 10%, 20%, 30%, 35%, 39%, preferably by at least 40%, or even at least 50%, such as 60%, 70%, 80%.
  the risk of exacerbations is reduced by at least 10%, 20%, 30%, 40%, or even at least 50%, such as 60%, 70%, 80%, 90% or even to 100%;
  the risk of exacerbations is reduced by a factor, 2 or more, such as 3, 4, 5, 6, 7, 8, 9, or even 10, or even more such as 20, 50 or even 100;
  mortality due to said vWF related disease is reduced by 10%, 20%, 30%, preferably by at least 40%, or even at least 50%, such as 60%, 70%, 80%, 90% or even to 100%;
  mortality due to said vWF related disease is reduced by a factor, 2 or more, such as 3, 4, 5, 6, 7, 8, 9, or even 10, or even more such as 20, 50 or even 100;
  remission is increased by a factor 1.2, 1.3, 1.4, 1.5, 1.6, 1.75, 1.8, 2 or more, such as 3, 4, 5, 6, 7, 8, 9, or even 10, or even more such as 20, 50 or even 100—refractoriness is reduced preferably by at least 10%, 20%, 30%, 40%, or even at least 50%, such as 60%, 70%, 80%, 90% or even to 100%; and/or
  refractoriness is reduced by a factor, 2 or more, such as 3, 4, 5, 6, 7, 8, 9, or even 10, or even more such as 20, 50 or even 100.

The term "reference activity" as used herein, refers to the average ADAMTS13 activity of 5 healthy subjects in the assay performed, which is set at 100%. For instance, in a fluorescence resonance energy transfer (FRET)-vWF73 assay, the calibration curve generated using a normal human plasma pool, in which the slope of the regression curve is calculated for each calibration sample, and used to generate the calibration curve (trend line: y=ax+b; with x=ADAMTS13(%) and y=delta RFU/delta time). The ADAMTS13 activity (%) of a sample is then calculated as: (y−b)×1/a, for instance as described by Kokame et al. (Br J Haematol. 2005, 129:93-100). Indeed, in general the patients that relapsed had a lower ADAMTS13 activity than the patients who did not relapse.

Accordingly, the present invention relates to a polypeptide for reducing the risk of and/or preventing ischaemic damage, organ damage and/or microthrombi formation, for instance causable by a vWF-related disease, such as TTP, an episode of TTP, e.g. an initial TTP episode and/or recurrent TTP episode(s), in a human in need thereof, comprising at least the following step (i) administering to said human a dose of 5-40 mg/day, preferably 10 mg/day or 11 mg/day of a polypeptide comprising at least one immunoglobulin single variable domain (ISVD) against von Willebrand Factor (vWF); wherein administration of said polypeptide reduces the risk of and/or prevents ischaemic damage, organ damage and/or microthrombi formation by at least 10%, 20%, 30%, preferably by at least 40%, or even at least 50%, such as 60%, 70%, 80%, 90% or even to 100%. Preferably, administration of said polypeptide reduces the risk of and/or prevents ischaemic damage, organ damage, refractoriness and/or microthrombi formation by a factor 1.2, 1.3, 1.4, 1.5, 1.6, 1.75, 1.8, 2 or more, such as 3, 4, 5, 6, 7, 8, 9, or even 10, or even more such as 20, 50 or even 100.

Accordingly, the present invention relates to a polypeptide for reducing the risk of and/or preventing ischaemic damage, organ damage, refractoriness and/or microthrombi formation as described herein, wherein said step of administrating said polypeptide is repeated for at least 1, 2, 3, 4, 5, 6, 7 days, or even longer such as 1 week, 2 weeks, 3 weeks, or even longer such as 1 month or even 2 months.

Accordingly, the present invention relates to a polypeptide for reducing the risk of and/or preventing ischaemic damage, organ damage, refractoriness and/or microthrombi formation as described herein, further comprising measuring ADAMTS13 activity of said patient, preferably once per week. Accordingly, the present invention relates to a polypeptide for reducing the risk of and/or preventing ischaemic damage, organ damage, refractoriness and/or microthrombi formation as described herein, wherein said step (i) of administrating said polypeptide is repeated for at least 1, 2, 3, 4, 5, 6, 7 days, or even longer such as 1 week, 2 weeks, 3 weeks, or even longer such as 1 month or even 2 months when the ADAMTS13 activity is [for the first time]≥5%, such as ≥10%, or even ≥15% of a reference ADAMTS13 activity.

Accordingly, the present invention relates to a polypeptide of the invention for treating a symptom of a vWF-related disease, such as TTP, as described herein in a human suffering from said disease, comprising administering to the subject a polypeptide of the invention, in an amount effective to treat the symptom of a vWF-related disease in a human suffering from said disease.

Accordingly, the present invention relates to a polypeptide of the invention for inhibiting in a human the onset or progression of a vWF-related disease, such as TTP, as described herein, the inhibition of which is effected by binding of a polypeptide comprising at least one ISVD against vWF to vWF, comprising administering to the human at a predefined interval effective inhibitory doses of said polypeptide, wherein each administration of the antibody delivers to the human from 0.1 mg per kg to 25 mg per kg of the human's body weight, preferably 10 mg or 11 mg of said polypeptide if said human has body weight ≥40 kg and 5 mg if said body weight is <40 kg, so as to thereby inhibit the onset or progression of the disease in the human.

Accordingly, the present invention relates to a polypeptide for reducing the likelihood of a human contracting ischaemic organ damage by a vWF-related disease, as described herein, which comprises administering to the human at a predefined dose a polypeptide comprising at least one immunoglobulin single variable domain (ISVD) against von Willebrand Factor (vWF), wherein each administration of the antibody delivers to the human from 0.1 mg per kg to 25 mg per kg of the human's body weight, preferably 10 mg or 11 mg of said polypeptide if said human has body weight ≥40 kg and 5 mg if said body weight is <40 kg, so as to thereby reduce the likelihood of the human contracting ischaemic organ damage.

Modeling based on these results indicates that maintaining administering polypeptides for prolonged times of the invention would be efficacious in preventing acute episodes. This advantageous profile results in a decreased health hazard. Hence, it can be concluded that the polypeptide of the invention prevents relapses.

Accordingly, the present invention relates to administering the polypeptide of the invention every 1, 2, 3, 4, 5, 6 7 days or even 2, 4, 6, or 8 weeks at doses ranging from 1-80 mg, such as 5-40 mg, preferably in preventing acute episodes of TTP. Particular efficacious doses are 10-20 mg. In particular embodiments, the dose comprises about 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably 10 mg or 11 mg of a polypeptide comprising at least one ISVD against vWF, such as ALX 0081 or ALX 0081-A. Particular efficacious doses in humans with a body weight <40 kg, such as children and adolescents are 2-10 mg. In particular embodiments, the dose comprises about 2, 3, 4, 5, 6, 7, 8, 9 or 10 mg, preferably 5 mg of a polypeptide comprising at least one ISVD against vWF, such as ALX 0081 or ALX 0081-A.

In an embodiment the present invention relates to a method of preventing relapse in a TTP patient, comprising
(1) optionally measuring ADAMTS13 activity from a TTP patient by an assay, such as a direct or an indirect assay;
(2) optionally comparing the ADAMTS1313 activity from a TTP patient with a reference value (normal value); and
(3) if the ADAMTS13 activity from a TTP patient is less than 15%, such as less than 10% and less than 5%, of the reference value, then administering the polypeptide of the invention, e.g. ALX 0081 or ALX 0081-A;
thereby preventing relapse.

Preliminary results suggest that administration of the first dose of the polypeptide of the invention before the first PE already results in an increase in the number of platelets.

Accordingly, the present invention relates to administering the polypeptide of the invention in a patient in need thereof, such as e.g. a patient experiencing an acute episode of TTP, such as an initial and/or recurrent episode(s) of TTP, a dose of about 1, 2, 3, 4, 5, 6, 7, 8, 9, 10, 11, 12, 13, 14, 15, 16, 17, 18, 19, 20, 25, 30, 35, 40, 50, 60, 70 or 80 mg, preferably 10 mg or 11 mg of a polypeptide comprising at least one ISVD against vWF, such as ALX 0081 or ALX 0081-A.

The polypeptides of invention comprising at least one ISVD against vWF, e.g. ALX 0081 or ALX 0081-A, can be administered to a subject (e.g., a human subject) alone or combination with a second agent, e.g., a second therapeutically or pharmacologically active agent, to treat or prevent (e.g., reduce or ameliorate one or more symptoms associated with) a vWF-related disease, e.g., TTP.

Non-limiting examples of agents that can be used as a second therapeutically or pharmacologically active agent or co-formulated or with the polypeptides of invention comprising at least one ISVD against vWF, e.g. ALX 0081 or ALX 0081-A, include, for example, adjunctive immunosuppressive treatment (e.g. corticosteroids such as (methyl) prednisolone or (methyl)-prednisone; or rituximab), anti-platelet agents (e.g. aspirin), supportive therapy with red cell transfusion or folate supplementation, treatment with vincristine or cyclosporin, anti-autoADAMTS13 antibodies, or ADAMTS13. Such combination therapies may advantageously utilize lower dosages of the administered therapeutic agents, thus avoiding possible toxicities or complications associated with the various monotherapies.

In an embodiment, the present invention relates to a combination therapy of the polypeptide of the invention together with an immunosuppressive treatment, in particular rituximab, which efficiently prevents relapses in TTP patients. Preferably, the combination therapy is provided until the ADAMTS13 activity is at least ≥5%, such as ≥10%, >15%, >20%, 25%, 30%, 35%, 40%, 45% or even normalised such as ≥50% of the normal activity, TTP remains a diagnosis based on clinical history, examination of the patient and the blood film. ADAMTS13 assays help to confirm the diagnosis and monitor the course of the disease and possible need for additional treatments. Acute episodes of TTP can be diagnosed according to Table 1 and the guidelines of, for instance, Scully et al. (2012, 2017 supra)

TABLE 1

Clinical signs and symptoms of an acute episode of TTP (initial or recurrent).

| | |
|---|---|
| Thrombocytopenia | Purpura, epistaxis, bruising, petechiae, gingival bleeding, haematuria, menorrhagia, gastrointestinal bleeding, etc |
| Neurological signs | Confusion, headache, paresis, aphasia, dysarthria, visual problems, encephalopathy, coma, etc |
| Fever | Body temperature >37.5° C. |
| Non-specific symptoms | Pallor, jaundice, fatigue, arthralgia or Myalgia, etc |
| Renal Impairment | Proteinuria, microhaematuria, etc |
| Cardiac | Chest pain, heart failure, hypotension, etc |
| Gastro-intestinal tract | Abdominal pain, etc |

The efficacy of any particular polypeptide of the invention or dosing regimen may be determined by methods available to those of skill in the art. Briefly, during a clinical trial, the patients may be observed by medical personnel and the state of disease is assessed by any combination of criteria. The improvement of a patient's disease state is determined based on these criteria at numerous time points and the combination of these determinations on a patient population is plotted to assess the efficacy of treatment.

In exemplary embodiments, assessment of efficacy may be measured by any or all of the criteria set forth below:
  Time-to-response of treatment, defined by a recovery of platelets ≥150,000/μL. This response must be confirmed at 48 hours after the initial reporting of platelet recovery above 150,000/μL by a de novo measure of platelets ≥150,000/μL and preferably by LDH≤2×ULN
  Number of subjects with complete remission
  Number of (subjects with) exacerbations of TTP and time to first exacerbation of TTP. Exacerbation is defined as recurrent thrombocytopenia following a response and requiring a re-initiation of daily PE treatment after 1 day but 30 days after the last daily PE.
  Number of subjects relapsing of TTP (defined as de novo event of TTP that occurs later than 30 days after the last daily PE) for a maximum of 1 year, and time to first relapse of TTP
  Daily PE data, including serious adverse events (SAEs) related to daily PE treatment
  Neurocognitive function, as measured by a neurocognitive test battery, at complete remission and at 1 year follow up. This test will be preceded by the Glasgow Coma Score to measure the state of consciousness of the subject
  Improvement of organ dysfunction and improvement of TTP related signs and symptoms
  Total mortality within the daily PE treatment period and within the subsequent study drug treatment period (including tapering)
  Determination of biomarkers of TTP including but not limited to a disintegrin-like and metalloprotease with thrombospondin repeats 13 (ADAMTS13) levels and anti-ADAMTS13 antibody titres.

The person skilled in the art is familiar to determine the efficacies.

For instance, ADAMTS13 activity can be evaluated using electrophoresis of vWF multimers to detect ultra-large multimers uncleaved by the protease (Moake et al. (1982) The New England journal of medicine 307, 1432-1435; Furlan, et al. (1997) Blood 89, 3097-3103 7, 8). ADAMTS13 activity can be tested employing FRETS-vWF73, a fragment of vWF chemically modified to emit fluorescence when cleaved by ADAMTS13. In the assay, FRETS-vWF73 is added to a sample of the patient's plasma, and the change in fluorescence is measured over time to determine ADAMTS13 activity. If an inhibitor is present, it is frequently a neutralizing IgG antibody directed against ADAMTS13, which can be measured by ELISA (Kokame et al. (2005) British journal of haematology 129, 93-100). Alternatively or in addition, ADAMTS13 activity can be determined as described in for instance Vesely et al. (2003, supra), Fontana et al. (2004, supra) or Remuzzi et al. (Blood 2002; 100: 778-7852002). For instance, indirect ADAMTS13 activity assays involve the detection of cleavage of products either of a full-length VWF molecule or a VWF fragment that encompasses the ADAMTS13 cleavage site in the A2 domain of VWF. (1) Collagen Binding Assays. Normal plasma or purified VWF is incubated with the test plasma sample in the presence of $BaCl_2$ and 1.5M urea which denatures the VWF. VWF is cleaved by ADAMTS13 and residual VWF is measured by its binding to collagen Type III. The bound VWF is quantitated using an ELISA assay with a conjugated anti-VWF antibody. (2) Ristocetin-Induced Aggregation. This is similar to the collagen-binding assay above but residual VWF is measured by ristocetin-induced platelet aggregation using a platelet aggregometer. (3) Functional ELISA assays. In this assay, a recombinant VWF fragment is immobilised onto an ELISA plate using an antibody to a tag on the VWF. The VWF fragment encodes the A2 domain and the ADAMTS13 cleavage site at Tyr1605-Met1606 and is tagged with Glutathion-S-transferase [GST]-histidine [GST-VWF73-His]. Plasma is added to the immobilised GST-VWF73-His fragment and cleavage of the immobilised fragment occurs at the ADAMTS13 cleavage site. The residual, cleaved VWF fragment is measured by using a second monoclonal antibody that recognises only the cleaved VWF fragment and not the interact fragment. ADAMTS13 activity is, therefore, inversely proportional to the residual substrate concentration. This method forms the basis for the TECHNOZYM® ADAMTS13 Activity ELISA.

The person skilled in the art is familiar in determining autoantibodies against ADAMTS13, for instance, anti-ADAMTS13 autoantibodies can be determined by ELISA, such as the TECHNOZYM® ADAMTS13 INH ELISA (Technoclone).

The person skilled in the art is familiar in determining of Ristocetin Cofactor activity in human samples, for instance, the Ristocetin Cofactor can be determined by the vW Select® of Bio/Data corp. on an aggregometer PAP-8E analyzer (Bio/Data corp.).

The person skilled in the art is familiar in determining Factor VIII in human samples, for instance using Coamatic Factor VIII (Chromogenix) on a STA-R evolution analyzer (Diagnostica Stago).

The person skilled in the art is familiar in determining von Willebrand Factor antigen in human samples, for instance using a immunoturbidimetric assay (e.g. using a STA Lia test vWF:Ag) on a STA-R evolution analyzer (Diagnostica Stago).

The person skilled in the art is familiar in determining LDH levels. Most methods are based on a lactate dehydrogenase-based enzymatic analysis on a spectrophotometer. A convenient review is provided by Medbø et al. (2000) "Examination of four different instruments for measuring blood lactate concentration". Scand J Clin Lab Invest 60:367-380. Various companies provide assays, such as Abnova (Catalog Number KA1653) which measures the catalysis by LDH of the interconversion of lactate and pyruvate, i.e. a non-radioactive colorimetric LDH assay based on the reduction of the tetrazolium salt MTT in a NADH-coupled enzymatic reaction to a reduced form of MTT which exhibits an absorption maximum at 565 nm. The intensity of the purple color formed is directly proportional to the enzyme activity. Similarly, in the Sigma Aldrich kit (MAK066-1KT), LDH reduces NAD to NADH, which is specifically detected by colorimetric (450 nm) assay. Normal levels are provided in the Table 1.1 below.

The person skilled in the art is familiar in determining troponin I and T. In general, troponin T and I are measured by immunoassay methods, which are available on many different immunoassay platforms, e.g. DPC Immulite, Abbott AxSYM, Bayer ACS:Centaur, Ortho Vitros, Roche Elecsys, third generation. A convenient review is provided by Wu et al. (1999) National Academy of Clinical Biochemistry Standards of Laboratory Practice: recommendations for the use of cardiac markers in coronary artery diseases. *Clin Chem.* July 1999; 45(7):1104-21. Normal levels are provided in the Table 1.1 below.

The person skilled in the art is familiar in determining creatinine. A convenient review is provided by Peake and Whiting "Measurement of Serum Creatinine—Current Status and Future Goals" Clin Biochem Rev. 2006 November; 27(4): 173-184. For instance, creatinine levels can be determined by Abcam Creatinine Assay Kit (ab65340) or BioVision's Creatinine Assay Kit. In the assay, creatinine is converted to creatine by creatininase, creatine is converted to sarcosine, which is specifically oxidized to produce a product which reacts with a probe to generate red color ($\lambda$max=570 nm) and fluorescence (Ex/Em=538/587 nm). Normal levels are provided in the Table 1.1 below. Since the amount of creatinine in the blood increases with muscle mass, men usually have higher creatinine levels than do women.

TABLE 1.1

| | | normal values | |
|---|---|---|---|
| Test | Specimen | Conventional Units | SI Units |
| Creatinine | Serum | 0.7-1.3 mg/dL | 61.9-115 µmol/L |
| Lactate dehydrogenase (LDH) | Serum | 60-160 U/L | 1-1.67 µkat/L |
| Troponin I | Plasma | <0.1 ng/ml | <0.1 µg/L |
| Troponin T | Serum | ≤0.03 ng/ml | ≤0.03 µg/L |

It will be appreciated that the normal levels provided in Table 1.1 can vary from lab to lab, between men and women, and by age. Nevertheless, the person skilled in the art will consider that depending on the assay used, the normal levels provided by the manufacturer can normally be used as a reference, or alternatively, the normal levels as assessed by the clinician in the specific setting.

The polypeptides of the invention typically comprise at least one ISVD against vWF. The ISVDs of the present invention bind to and/or have affinity for vWF ("against vWF"). In the context of the present invention, "vWF" includes, but is not limited, to cynomolgus, baboon, pig, guinea pig, mouse, and/or human vWF and most preferred human vWF, i.e. SEQ ID NO: 20 or GenBank entry: NP_000543.

Preferably, the ISVD against vWF essentially consists of 4 framework regions (FR1 to FR4, respectively) and 3 complementarity determining regions (CDR1 to CDR3, respectively), in which:
a) CDR1 comprises or essentially consists of:
   the amino acid sequence YNPMG; or
   an amino acid sequence that has 2 or only 1 amino acid difference(s) with the amino acid sequence YNPMG;
   and
b) CDR2 comprises or essentially consists of:
   the amino acid sequence AISRTGGSTYYPDSVEG; or
   an amino acid sequence that has at least 80%, preferably at least 90%, more preferably at least 95%, even more preferably at least 99% sequence identity with the amino acid sequence AISRTGGSTYYPDSVEG; or
   an amino acid sequence that has 2 or only 1 amino acid difference(s) with the amino acid sequence AISRTGGSTYYPDSVEG;
   and
c) CDR3 comprises or essentially consists of:
   the amino acid sequence AGVRAEDGRVRTLPSEYTF; or
   an amino acid sequence that has at least 80%, preferably at least 90%, more preferably at least 95%, even more preferably at least 99% sequence identity with the amino acid sequence AGVRAEDGRVRTLPSEYTF; or
   an amino acid sequence that has 2 or only 1 amino acid difference(s) with the amino acid sequence AGVRAEDGRVRTLPSEYTF.

Even more preferably, the ISVD against vWF essentially consists of 4 framework regions (FR1 to FR4, respectively) and 3 complementarity determining regions (CDR1 to CDR3, respectively), in which:
a) CDR1 is YNPMG (SEQ ID NO: 21);
b) CDR2 is AISRTGGSTYYPDSVEG (SEQ ID NO: 22); and
c) CDR3 is AGVRAEDGRVRTLPSEYTF (SEQ ID NO: 23).

Even more preferably, the ISVD against vWF is represented by SEQ ID NO: 19 (12A02H1).

Preferably, the polypeptides of the invention comprise or consist of at least two ISVDs against vWF.

Even more preferably, the polypeptides of the present invention comprise or consist of two ISVDs against vWF defined by SEQ ID NO:s 1-18 or 24, and most preferably SEQ ID NO: 1 (ALX 0081; INN "caplacizumab") or SEQ ID NO: 24. ALX 0081 is a bivalent Nanobody, consisting of two identical monovalent building blocks, that target vWF. ALX 0081-A is ALX 0081 plus a C-terminal alanine.

The polypeptides comprising at least one ISVD against vWF, e.g. SEQ ID NO:s 1-19 or 24, may be used in a treatment of a vWF-related disease, in particular thrombotic thrombocytopenic purpura (TTP).

The terms "polypeptide" and "amino acid sequence" are used interchangeably herein.

Thus, for example, suitable polypeptides for use in the invention may include the compounds in Table A-1, e.g. SEQ ID NO: 1-19 or 24, or a compound having 80% or more, more preferably 85% or more, most preferred 90%, 95%, 96%, 97%, 98%, 99% or more, amino acid sequence identity to a compound defined by any of SEQ ID NO: 1-19 or 24 in Table A-1 (see Definition section for "sequence identity").

Preferably the ISVD against vWF for use in the polypeptides of the invention are 12A02H1-like compounds. For the purposes of the present description a 12A02H1-like compound is a compound which comprises 12A02H1 (i.e. SEQ ID NO: 19) or a compound having 80% or more, more preferably 85% or more, most preferably 90%, 95%, 96%, 97%, 98%, 99% or more, amino acid sequence identity to 12A02H1 (SEQ ID NO: 19). A particularly preferred polypeptide comprising two ISVDs against vWF is ALX 0081 (SEQ ID NO: 1) or ALX 0081-A (SEQ ID NO: 24).

Immunoglobulin single variable domains, such as camelid VHH domains, camelized VH domains or humanized VHH domains, represent a rapidly growing class of therapeutics. For example, immunoglobulin single variable domains against vWF have been described in WO2004/015425, WO2004/062551, WO2006/074947, WO2006/122825, WO2009/115614, and WO2011/067160. Further preferred immunoglobulin single variable domains for use in the polypeptides of the invention include the improved Nanobodies described in WO06/122825.

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "variable domain sequence", "VHH sequence" or "protein sequence"), should generally be understood to include both the relevant amino acid sequence as well as nucleic acids or nucleotide sequences encoding the same, unless the context requires a more limited interpretation.

The term "immunoglobulin single variable domain" ("ISVD"), interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs.

The term "immunoglobulin single variable domain" hence does not comprise conventional immunoglobulins or their fragments which require interaction of at least two variable domains for the formation of an antigen binding site. This is also the case for embodiments of the invention which "comprise" or "contain" an immunoglobulin single variable domain. In the context of the present invention, such embodiments exclude conventional immunoglobulins or their fragments. Thus, a polypeptide or a composition that "comprises" or "contains" an immunoglobulin single variable domain may relate to e.g. constructs comprising more than one immunoglobulin single variable domain. Alternatively, there may be further constituents other than the immunoglobulin single variable domains, e.g. auxiliary agents of different kinds, protein tags, colorants, dyes, etc. However, these terms do comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a VL-sequence) or a suitable fragment thereof; or a heavy chain variable domain sequence (e.g. a VH-sequence or VHH sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments (single chain variable fragment) that need to interact with another variable domain—e.g. through a VH/VL interaction—to form a functional antigen binding domain).

In one embodiment of the invention, the immunoglobulin single variable domains are light chain variable domain sequences (e.g. a VL-sequence), or heavy chain variable domain sequences (e.g. a VH-sequence); more specifically, the immunoglobulin single variable domains can be heavy chain variable domain sequences that are derived from a conventional four-chain antibody or heavy chain variable domain sequences that are derived from a heavy chain antibody (e.g. a VHH).

For a general description of heavy chain antibodies and the variable domains thereof, reference is inter alia made to the prior art cited herein, as well as to the prior art mentioned on page 59 of WO 08/020079 and to the list of references mentioned on pages 41-43 of the International application WO 06/040153, which prior art and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

For example, the single variable domain or immunoglobulin single variable domain (or an amino acid sequence that is suitable for use as an immunoglobulin single variable domain) may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH sequence); other single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-6), to Holt et al. 2003 (Trends Biotechnol. 21(11): 484-490); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

The amino acid sequence and structure of an immunoglobulin sequence, in particular an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in an immunoglobulin single variable domain can be in the region of 110-120, is preferably 112-115, and is most preferably 113. It should however be noted that parts, fragments, analogs or derivatives of an immunoglobulin single variable domain are not particularly limited as to their length and/or size, as long as such parts, fragments, analogs or derivatives meet the further requirements outlined herein and are also preferably suitable for the purposes described herein.

Thus, in the meaning of the present invention, the term "immunoglobulin single variable domain" or "single variable domain" comprises peptides which are derived from a non-human source, preferably a camelid, preferably a camel heavy chain antibody. They may be humanized, as previously described, e.g. in WO 08/101985 and WO 08/142164. Moreover, the term comprises polypeptides derived from non-camelid sources, e.g. mouse or human, which have been "camelized", as previously described, e.g. in WO 08/101985 and WO 08/142164.

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences and humanized camelid immunoglobulin sequences, or camelized immunoglobulin single variable domains, e.g. camelized dAb as described by Ward et al (see for example WO 94/04678 and Davies and Riechmann 1994, Febs Lett. 339: 285 and 1996, Protein Engineering 9: 531).

All the ISVDs against vWF (or vWF binders) mentioned above are well known from the literature. This includes their manufacture (see in particular e.g. WO2006/122825 but also WO2004/062551). For example, ALX 0081 or ALX 0081-A is prepared as described e.g. in WO2006/122825 or WO2009/115614.

The immunoglobulin single variable domains provided by the invention are preferably in isolated form or essentially isolated form, or form part of a protein or polypeptide of the invention, which may comprise or essentially consist of one or more immunoglobulin single variable domains and which may optionally further comprise one or more further amino acid sequences (all optionally linked via one or more suitable linkers). For example, and without limitation, the one or more immunoglobulin single variable domains may be used as a binding unit in such a protein or polypeptide, which may optionally contain one or more further amino acid sequences that can serve as a binding unit (i.e. against one or more other targets than cell associated antigens), so as to provide a monovalent, multivalent or multispecific polypeptide of the invention, respectively, all as described herein. Such a protein or polypeptide may also be in isolated or essentially isolated form. Thus, according to the invention, immunoglobulin single variable domains comprise constructs comprising two or more antigen binding units in the form of single domains, as outlined above. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific etc. constructs can be formed. For example, a polypeptide according to the invention may comprise two immunoglobulin single variable domains directed against target A, and one immunoglobulin single variable domain against target B, making it bivalent for A and monovalent for B. Such constructs and modifications thereof, which the skilled person can readily envisage, are all encompassed by the present invention. In particular embodiments, the invention relates to bi-paratopic constructs comprising at least two immunoglobulin single variable domains directed to different epitopes within the same target antigen.

All these molecules are also referred to as "polypeptide of the invention", which is synonymous with "immunoglobulin sequences" or "immunoglobulin single variable domains" of the invention.

In addition, the term "sequence" as used herein (for example in terms like "immunoglobulin sequence", "antibody sequence", "variable domain sequence", "$V_{HH}$-sequence" or "protein sequence"), should generally be understood to include both the relevant amino acid sequence as well as nucleic acid sequences or nucleotide sequences encoding the same, unless the context requires a more limited interpretation.

According to one non-limiting embodiment of the invention, the immunoglobulin sequences, Nanobody® or polypeptide of the invention is glycosylated. According to another non-limiting embodiment of the invention, the immunoglobulin sequences, Nanobody® or polypeptide of the invention is non-glycosylated.

As mentioned supra, the present invention relates to polypeptides typically comprising at least one, such as 2 or more ISVDs against vWF, i.e. ISVDs that bind and/or have affinity for an antigen as defined herein, e.g. von Willebrand Factor (vWF) and preferably human vWF (SEQ ID NO: 20).

In the context of the present invention, "binding to and/or having affinity for" a certain antigen has the usual meaning in the art as understood e.g. in the context of antibodies and their respective antigens.

In particular embodiments of the invention, the term "binds to and/or having affinity for" means that the immunoglobulin sequence specifically interacts with an antigen, and is used interchangeably with immunoglobulin sequences "against" the said antigen.

The term "specificity" refers to the number of different types of antigens or antigenic determinants to which a particular immunoglobulin sequence, antigen-binding molecule or antigen-binding protein (such as a Nanobody® or a polypeptide of the invention) can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody® or polypeptide of the invention) and the pertinent antigen. Avidity is related to both the affinity between an antigenic determinant and its antigen binding site on the antigen-binding molecule and the number of pertinent binding sites present on the antigen-binding molecule.

Typically, immunoglobulin sequences of the present invention (such as the amino acid sequences, Nanobodies® and/or polypeptides of the invention) will bind to their antigen with a dissociation constant (KD) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant (KA) of $10^5$ to $10^{12}$ liter/moles or more, and preferably $10^7$ to $10^{12}$ liter/moles or more and more preferably $10^8$ to $10^{12}$ liter/moles), and/or bind to cell associated antigens as defined herein with a kon-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$; and/or bind to cell associated antigens as defined herein with a koff rate between 1 $s^{-1}$ (t½=0.69 s) and $10^{-6}$ $s^{-1}$ (providing a near irreversible complex with a t½ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Any KD value greater than $10^{-4}$ M (or any KA value lower than $10^4$ $M^{-1}$) is generally considered to indicate non-specific binding.

Preferably, a monovalent immunoglobulin sequence of the invention will bind to the desired antigen with an affinity less than 500 nM, preferably less than 200 nM, more preferably less than 10 nM, such as less than 500 pM.

Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant (KD) may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant (KA), by means of the relationship [KD=1/KA].

The affinity denotes the strength or stability of a molecular interaction. The affinity is commonly given as by the KD, or dissociation constant, which has units of mol/liter (or M). The affinity can also be expressed as an association constant, KA, which equals 1/KD and has units of (mol/liter)$^{-1}$ (or $M^{-1}$). In the present specification, the stability of the interaction between two molecules (such as an amino acid sequence, immunoglobulin sequence, Nanobody® or polypeptide of the invention and its intended target) will mainly be expressed in terms of the KD value of their interaction; it being clear to the skilled person that in view of the relation KA=1/KD, specifying the strength of molecular interaction by its KD value can also be used to calculate the corresponding KA value. The KD-value characterizes the strength of a molecular interaction also in a thermodynamic sense as it is related to the free energy (DG) of binding by the well-known relation DG=RT·ln(KD) (equivalently DG=−RT·ln(KA)), where R equals the gas constant, T equals the absolute temperature and ln denotes the natural logarithm.

The KD for biological interactions, such as the binding of the immunoglobulin sequences of the invention to the cell associated antigen as defined herein, which are considered meaningful (e.g. specific) are typically in the range of $10^{-10}$ M (0.1 nM) to $10^{-5}$ M (10000 nM). The stronger an interaction is, the lower is its KD.

The KD can also be expressed as the ratio of the dissociation rate constant of a complex, denoted as koff, to the rate of its association, denoted kon (so that KD=koff/kon and KA=kon/koff). The off-rate koff has units $s^{-1}$ (where s is the SI unit notation of second). The on-rate kon has units $M^{-1}$ $s^{-1}$.

As regards immunoglobulin sequences of the invention, the on-rate may vary between $10^2$ $M^{-1}$ $s^{-1}$ to about $10^7$ $M^{-1}$ $s^{-1}$, approaching the diffusion-limited association rate constant for bimolecular interactions. The off-rate is related to the half-life of a given molecular interaction by the relation t½=ln(2)/koff. The off-rate of immunoglobulin sequences of the invention may vary between $10^{-6}$ $s^{-1}$ (near irreversible complex with a t½ of multiple days) to 1 $s^{-1}$ (t½=0.69 s).

The affinity of a molecular interaction between two molecules can be measured via different techniques known per se, such as the well-known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding kon, koff measurements and hence KD (or KA) values. This can for example be performed using the well-known Biacore instruments.

It will also be clear to the skilled person that the measured KD may correspond to the apparent KD if the measuring process somehow influences the intrinsic binding affinity of the implied molecules for example by artefacts related to the coating on the biosensor of one molecule. Also, an apparent KD may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of KD may be quite labour-intensive and as consequence, often apparent KD values are determined to assess the binding strength of two molecules. It should be noted that as long as all measurements are made in a consistent way (e.g. keeping the assay conditions unchanged) apparent KD measurements can be used as an approximation of the true KD and hence in the present document KD and apparent KD should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result, an $IC_{50}$ value is obtained corresponding to the concentration of A at which the signal measured for C in absence of A is halved. Provided KD ref, the KD of the reference molecule, is known, as well as the total concentration $c_{ref}$ of the reference molecule, the apparent KD for the interaction A-B can be obtained from following formula: KD=IC50/(1+cref/KD ref). Note that if cref<<KD ref, KD≈IC50. Provided the measurement of the IC50 is performed in a consistent way (e.g. keeping cref fixed) for the binders that are compared, the strength or stability of a molecular interaction can be assessed by the IC50 and this measurement is judged as equivalent to KD or to apparent KD throughout this text.

The present invention relates to immunoglobulin single variable domains described in, or obtainable by the methods as disclosed in WO2004/015425, WO2004/062551, WO2006/074947, WO2006/122825, WO2009/115614, or WO2011/067160, all in the name of the present applicant.

The invention also encompasses optimized variants of these amino acid sequences. Generally, an "optimized variant" of an amino acid sequence according to the invention is a variant that comprises one or more beneficial substitutions such as a substitutions increasing i) the degree of "humanization", ii) the chemical stability, and/or iii) the level of expression; while the potency (measured e.g. by the potency assay as described in the experimental part of WO2006/122825 remains comparable (i.e. within a 10% deviation) to the wild type 12A02 (as defined in WO2006/122825) or comparable to the variant 12A02H1 (SEQ ID NO: 19), also as defined in WO2006/122825. Preferably, compared to the wild-type sequence of 12A02, an amino acid sequence of the invention contains at least one such substitution, and preferably at least two such substitutions, and preferably at least three humanizing substitutions and preferably at least 10 such humanizing substitutions.

In a particular aspect, the amino acid sequences of the invention contain a total of between 1 and 15, preferably between 2 and 14, such as between 9 and 13, e.g. 10, 11 or 12 amino acid substitutions compared to the wild-type sequence 12A02. As mentioned, these differences preferably at least comprise one and preferably at least two, such as three, four or five or ten humanizing substitutions, and may optionally comprise one or more further substitutions (such as any one of, or any suitable combination of any two or more of, the further substitutions (a) to (c) as mentioned herein). Again, based on the disclosure herein and optionally after a limited degree of trial and error, the skilled person will be able to select (a suitable combination of) one or more such suitable humanizing and/or further substitutions.

The present invention encompasses polypeptide sequences that are highly similar to any of the specific examples provided herein, or any of the specific examples defined by reference above. Highly similar means an amino acid identity of at least 90%, e.g. 95, 97, 98 or 99%. The highly similar polypeptide sequences will have the same function as the sequence they are derived from, i.e. they will bind to vWF, more specifically bind to and inhibit interaction between vWF and platelets, such as ALX 0081-A which is derived from ALX 0081.

In a particular embodiment, the invention relates to sequences highly similar to any one of SEQ ID NO:s 1-19 or 24, in particular SEQ ID NO: 1. However, for each variant sequence stability in the formulation as defined herein has to be evaluated, such that the invention in particular refers to variants or highly similar sequences which are stable in the formulations as defined herein.

Methods to generate polypeptide sequences of the invention are widely known and include e.g. recombinant expression or synthesis. The skilled person is well acquainted with suitable expression technology, e.g. suitable recombinant vectors and host cells, e.g. bacterial or yeast host cells. The skilled person is also well acquainted with suitable purification techniques and protocols.

The present invention provides also formulations of polypeptides comprising at least one immunoglobulin single variable domain against vWF, e.g. ALX 0081 or ALX 0081-A, which are stable, and preferably suitable for pharmaceutical uses, including the preparation of medicaments (also called "pharmaceutical formulation of the invention" or "formulation(s) of the invention").

In particular embodiments, the formulation comprises one or more polypeptides selected from SEQ ID NO:s 1-19 or 24, preferably SEQ ID NO: 1.

The term "pharmaceutical formulation" refers to a preparation which is in such form as to permit the biological activity of the active ingredient (the polypeptide of the invention) to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

The term "excipient" as used herein refers to an inert substance which is commonly used as a diluent, vehicle, preservative, lyoprotectant, surfactant, binder, carrier or stabilizing agent for compounds which impart a beneficial physical property to a formulation. The skilled person is familiar with excipients suitable for pharmaceutical purposes, which may have particular functions in the formulation, such as lyoprotection, stabilization, preservation, etc.

A "sterile" formulation is aseptic or free or essentially free from all living microorganisms and their spores. This is readily accomplished by filtration through sterile filtration membranes.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. In certain embodiments, the formulation is stable at about 40° C. for at least about 1, 2, 3, 4, 5, 6, 7, 8, or more weeks. Furthermore, the formulation is preferably stable following freezing (to, e.g., −20° C. or −70° C.) and thawing of the formulation, for example following 1, 2 3, 4, or 5 cycles of freezing and thawing. Stability can be evaluated qualitatively and/or quantitatively in a variety of different ways known by the person skilled in the art. Stability studies showed that ALX 0081 or ALX 0081-A is stable at −20° C. for at least 3 years.

The formulation comprises an aqueous carrier. The aqueous carrier is in particular a buffer.

As used herein, "buffer" refers to a buffered solution that resists changes in pH by the action of its acid-base conjugate components. The formulation of the invention comprises a buffer selected from at least one of citrate or phosphate buffer, preferably a citrate buffer. As determined previously, these buffers enhance the stability of the vWF binders.

The formulation according to the invention comprises a citrate buffer at a concentration in the range of 5-200 mM, preferably 7.5-80 mM, even more preferably 10-50, e.g. 10, 15, 20, 25 or 30 mM, and most preferably 20 mM, wherein each value is understood to optionally encompass a range of ±5 mM. Alternatively, the formulation according to the invention may comprise a phosphate buffer at a concentration in the range of 5-200 mM, preferably 5-80 mM, more preferably 7.5-60 mM, even more preferably 10-40, e.g. 10, 15, 20, 25 or 30 mM, and most preferably 10 mM, wherein each value is understood to optionally encompass a range of ±5 mM. It will be understood that a lower concentration of the buffer has an effect on the final osmolality, and correspondingly on the additional solutes that may have to be added.

The pH of the formulation of the invention is in the range 5.0 to 7.5, wherein each value is understood to encompass a range of ±0.2. The most advantageous pH will depend on the buffer comprised in the formulation. Hence, the invention relates particularly to a formulation comprising a phosphate buffer, which preferably has a pH in the range of 6.5 to 7.5, preferably 6.9, 7.0, 7.1, e.g. 7.1. It was shown that a formulation comprising a citrate buffer was outstandingly suitable for storage and use. Hence, the present invention relates to a formulation comprising a citrate buffer, which preferably has a pH between 6.0 and 7.0, more preferably 6.1, 6.2, 6.3, 6.4, 6.5, 6.6, 6.7, 6.8 or 6.9, e.g. 6.5, wherein each value is understood to optionally encompass a range of ±0.2.

The formulations of the invention will comprise the polypeptides of the invention, in particular the immunoglobulin single variable domains or polypeptides comprising at least one immunoglobulin single variable domain against vWF, such as ALX 0081 or ALX 0081-A, at a concentration that is suitable for clinical purposes, which includes concentrations used in stock solutions for dilution prior to use on the patient. Apart from improved stabilization, the formulations of the invention enable high concentrations of the polypeptides comprising at least one ISVD against vWF, such as ALX 0081 or ALX 0081-A.

Typical concentrations of the active agent, e.g. polypeptides comprising at least one ISVD against vWF such as ALX 0081 or ALX 0081-A, in formulations of the invention comprise the non-limiting examples of concentrations in the range of 0.1 to 150 mg/mL, such as 1-100 mg/mL, 5-80 mg/mL, or 10-40 mg/mL, preferably 10 mg/mL or 11 mg/ml, wherein each value is understood to optionally encompass a range of ±20% (e.g. a value of 10 optionally encompasses a range of 8 to 12 mg/mL).

In a further embodiment of the invention, the formulation according to any aspect of the invention may further comprise a detergent or surfactant.

Herein, a "surfactant" refers to a surface-active agent, preferably a nonionic surfactant. Examples of surfactants herein include polysorbate; poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT® series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant herein is polysorbate 80. Preferred suitable detergents or surfactants for use with the invention include, but are not limited to, polyoxyethylene sorbitan fatty acid esters e.g. polysorbate −20, −40, −60, −65, −80 or −85. Common brand names for polysorbates include Alkest, Canarcel and Tween. The skilled person knows further non-limiting examples of detergents, such as those listed e.g. in WO2010/077422. In a preferred embodiment, the detergent is a non-ionic detergent. More specifically, the detergent is polysorbate-80, also designated Tween-80 hereafter. The skilled person can readily determine a suitable concentration of detergent for a formulation of the invention. Typically, the concentration will be as low as possible, whilst maintaining the beneficial effects of the detergents, e.g. a stabilizing effect under conditions of shear stress, e.g. stirring, which reduces aggregation of the formulated polypeptides of the invention. In exemplary, non-limiting embodiments, the concentration of the detergent may be in the range of 0.001 to 0.5%, e.g. 0.001, 0.002, 0.003, 0.004, 0.005, 0.01, 0.015, 0.02, 0.025, 0.03, 0.035, 0.04, 0.045, 0.05%, 0.1%, 0.2%, 0.3%, 0.4% or 0.5%, preferably in a concentration between 0.01 and 0.05%, more preferably between 0.01 and 0.02%, e.g. 0.01% (v/v).

The formulation of the invention may further comprise excipients such as preservatives.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

The formulation of the invention may further comprise stabilizing agents, such as a polyols.

A "polyol" is a substance with multiple hydroxyl groups, and includes sugars (reducing and nonreducing sugars), sugar alcohols and sugar acids. A polyol may optionally be included in the formulation, for instance to improve stability. In certain embodiments, polyols herein have a molecular weight which is less than about 600 kD (e.g. in the range from about 120 to about 400 kD). A "reducing sugar" is one which contains a hemi-acetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it desired that the formulation is freeze-thaw stable, the polyol is preferably one which does not crystallize at freezing temperatures (e.g. −20° C.) such that it destabilizes the antibody in the formulation. In certain embodiments, nonreducing sugars such as sucrose and trehalose are examples of polyols, with sucrose being preferred, despite the solution stability of trehalose.

Therapeutic compounds of the invention used in accordance with the present invention are prepared for storage by mixing a polypeptide(s) having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed. Accordingly, the formulations according to the invention may also optionally comprise one or more excipients.

Commonly used stabilizers and preservatives are well known to the skilled person (see e.g. WO2010/077422). Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, hydrophilic polymers such as polyvinyl pyrrolidone, cellulose based substances, polyethylene glycol, sodium carboxymethylcellulose, polyacrylates, waxes, gelatin, polyethylene polyoxypropylene block polymers, polyethylene glycol and wool fat. antioxidants including ascorbic acid and methionine; preservatives; low molecular weight (less than about 10 residues) polypeptides; proteins; and amino acids such as glycine, glutamine, asparagine, histidine, arginine, or lysine. In advantageous embodiments, the excipient may be one or more selected from the list consisting of NaCl, trehalose, sucrose, mannitol or glycine.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The polypeptides of the invention may be formulated into any pharmaceutically acceptable formulation. The formulation may be liquid or dry. The formulation may be generated via mixing, drying, lyophilization, vacuum drying, or any known method for formulating pharmaceutical compositions.

A preferred formulation of the invention comprises a polypeptide comprising at least one ISVD against vWF, such as ALX 0081 or ALX 0081-A, in a phosphate buffer solution (pH 7.1). Even more preferably, a formulation of the invention comprises a polypeptide comprising at least one ISVD against vWF, such as ALX 0081 or ALX 0081-A, in a phosphate buffer solution (pH 7.1), Glycine (0.2 M) and polysorbate 80 (0.02% v/v).

The polypeptides of the invention may further be formulated as described in WO 2014/184352.

A particularly preferred formulation comprises:
(a) a polypeptide comprising at least one ISVD against vWF, such as ALX 0081 or ALX 0081-A at a concentration from about 0.1 mg/mL to about 80 mg/mL, preferably 5 mg or 10 mg or 11 mg;
(b) an excipient chosen from sucrose, glycine, mannitol, trehalose or NaCl at a concentration of about 1% to about 15% (w/v);
(c) Tween-80 at a concentration of about 0.001% to 0.5% (v/v); and
(d) a citrate buffer at a concentration of about 5 mM to about 200 mM such that the pH of the formulation is about 6.0 to 7.0.

A further preferred formulation of the invention comprises a polypeptide comprising at least one ISVD against vWF, such as ALX 0081 or ALX 0081-A, preferably at a concentration of 5 mg/ml, 10 mg/ml or 11 mg/ml, a citrate buffer at a concentration of 20 mM (pH 6.5), further comprising 7% sucrose (w/v), and Tween-80 at a concentration of 0.01% (v/v).

In some embodiments, a formulation is stored as a liquid. In other embodiments, a formulation is prepared as a liquid and then is dried, e.g., by lyophilization or spray-drying, prior to storage. A dried formulation can be used as a dry compound, e.g., as an aerosol or powder, or reconstituted to its original or another concentration, e.g., using water, a buffer, or other appropriate liquid.

The present invention also relates to vials comprising filled with lyophilisate containing 12.5 mg caplacizumab and excipients for solution for injection. Excipients (per mL of reconstituted solution): 0.21 mg citric acid, 5.58 mg tri sodium citrate di-hydrate, 70 mg sucrose, 0.11 mg polysorbate-80 per vial (pH 6.5+/−0.5). After reconstitution with 1 mL Water for injection (WFI) strength is 12.5 mg/mL caplacizumab (for administered nominal dose of 10 mg or 11 mg).

The invention also encompasses products obtainable by further processing of a liquid formulation, such as a frozen, lyophilized or spray-dried product. Upon reconstitution, these solid products can become liquid formulations as described herein (but are not limited thereto). In its broadest sense, therefore, the term "formulation" encompasses both liquid and solid formulations. However, solid formulations are understood as derivable from the liquid formulations (e.g. by freezing, freeze-drying or spray-drying), and hence have various characteristics that are defined by the features specified for liquid formulations herein. The invention does not exclude reconstitution that leads to a composition that deviates from the original composition before e.g. freeze- or spray drying. accordingly, the lyophilized formulation may be reconstituted to produce a formulation that has a concentration that differs from the original concentration (i.e., before lyophilization), depending upon the amount of water or diluent added to the lyophilate relative to the volume of liquid that was originally freeze-dried. Suitable formulations can be identified by assaying one or more parameters of antibody integrity.

In a preferred embodiment, the formulations according to the invention are isotonic in relation to human blood. Isotonic solutions possess the same osmotic pressure as blood plasma, and so can be intravenously infused into a subject without changing the osmotic pressure of the subject's blood plasma. Tonicity can be expressed in terms of osmolality, which can be a theoretical osmolality, or preferably an experimentally determined osmolality. Typically, osmolality will be in the range of 290±60 mOsm/kg, preferably 290±20 mOsm/kg.

The formulations of the invention may also comprise compounds that are specifically useful for protecting the polypeptide of the invention during freeze-drying. Such compounds are also known as lyoprotectants, and are well known to the skilled person. Specific examples include, but are not limited to sugars like sucrose, sorbitol or trehalose; amino acids such as glutamate, in particular monosodium glutamate or histidine; betain, magnesium sulfate, sugar alcohols, propylene glycol, polyethylene glycols and combinations thereof. By appreciating the invention, the required amount of such a compound to be added can readily be determined by the skilled person under consideration of stability of the formulation in liquid form and when undergoing lyophilization. Formulations that are particularly suitable for freeze-drying may furthermore comprise bulking agents. Suitable agents are widely known to the skilled person. It has been shown that a formulation comprising sucrose was not only particularly suited for maintaining the physical stability, during e.g. storage and freeze-thawing, of the vWF binders, but also as lyoprotectant.

As outlined, any of the above formulations can be further processed e.g. by lyophilization, spray-drying or freezing, e.g. bulk freezing. The resulting processed product has characteristics derived from the liquid starting formulation, as defined above. Where necessary, additional agents may be included for further processing, such as, for instance, lyoprotectants, etc.

The formulations of the present invention have the effect after lyophilization of maintaining the chemical and physical integrity of the polypeptides of the present invention, in particular ALX 0081 or ALX 0081-A, i.e. even after prolonged storage, e.g. for durations as defined above, at temperatures between −70° C. and +40° C., the purity/impurity profile of the product is essentially not changing. For example, prolonged storage after lyophilization did not have a significant effect on Reverse Phase High Performance Liquid Chromatography (RP-HPLC), Size Exclusion High Performance Liquid Chromatography (SE-HPLC) or Capillary IsoElectric Focusing (cIEF) profiles.

The polypeptides of the invention can be produced by any commonly used method. Typical examples include the recombinant expression in suitable host systems, e.g. bacteria or yeast. The polypeptides of the invention will undergo a suitable purification regimen prior to being formulated in accordance to the present invention.

In general, the polypeptides of the invention are produced by living host cells that have been genetically engineered to produce the polypeptide. Methods of genetically engineering cells to produce proteins are well known in the art. See e.g. Ausubel et al., eds. (1990), Current Protocols in Molecular Biology (Wiley, New York). Such methods include introducing nucleic acids that encode and allow expression of the polypeptide into living host cells. These host cells can be bacterial cells, fungal cells, or animal cells grown in culture. Bacterial host cells include, but are not limited to, *Escherichia coli* cells. Examples of suitable *E. coli* strains include: HB101, DH5a, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well known by those skilled in the art (e.g., by transformation, viral infection, and/or selection). Optionally, the polypeptide can be secreted by the host cells into the medium.

In some embodiments, the polypeptides can be produced in bacterial cells, e.g., *E. coli* cells. For example, if the polypeptide is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the polypeptide is not fused to the gene III protein and is secreted into the periplasm and/or media.

The polypeptides can also be produced in eukaryotic cells. In one embodiment, the polypeptides are expressed in a yeast cell such as *Pichia* (see, e.g., Powers et al. 2001 J Immunol Methods 251:123-35), *Hansenula*, or *Saccharomyces*.

In one embodiment, polypeptides are produced in mammalian cells. Typical mammalian host cells for expressing the clone antibodies or antigen-binding fragments thereof include Chinese Hamster Ovary (CHO cells) (including dhfr-CHO cells, described in Urlaub and Chasin, 1980 Proc. Natl. Acad. Sci. USA 77:4216-4220, used with a DHFR selectable marker, e.g., as described in Kaufman and Sharp, 1982 Mol. Biol. 159:601-621), lymphocytic cell lines, e.g., NSO myeloma cells and SP2 cells, COS cells, and a cell from a transgenic animal, e.g., a transgenic mammal. For example, the cell is a mammary epithelial cell.

In addition to the nucleic acid sequences encoding the polypeptide, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). For example, typically the selectable marker gene confers resistance to drugs, such as G418, hygromycin, or methotrexate, on a host cell into which the vector has been introduced.

Standard molecular biology techniques can be used to prepare the recombinant expression vector, transfect the host cells, select for transformants, culture the host cells and recover the antibody molecule from the culture medium. For example, the polypeptides of the invention can be isolated by affinity chromatography.

In one embodiment, the polypeptide of the invention is purified as described in WO 10/056550. In an exemplary embodiment, the polypeptide is purified from one or more contaminants by: contacting a mixture of polypeptide and contaminant(s) with a Protein A-based support and/or an ion exchange support, under conditions that allow the polypeptide to bind to or adsorb to the support; removing one or more contaminants by washing the bound support under conditions where the polypeptide remains bound to the support, and selectively eluting the polypeptide from the support by eluting the adsorbed polypeptide molecule with an elution buffer.

The polypeptides of the invention can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody molecule and a signal sequence for secretion. The milk produced by females of such transgenic mammals includes, secreted therein, the single domain of interest. The antibody molecule can be purified from the milk, or for some applications, used directly.

The present invention encompasses methods of producing the formulations as defined herein.

The purification and formulation steps may coincide, e.g. when the polypeptides of the invention are eluted from a column using a buffer according to the present invention. Alternatively, the formulations of the invention can be prepared by exchanging a buffer by any suitable means, e.g. means widely used in the art such as dialyzing, ultrafiltration, etc.

In some embodiments the method of producing a formulation of the invention may also relate to the reconstitution of a lyophilized or spray-dried formulation, e.g. by addition of water or a suitable buffer (which may optionally comprise further excipients).

The methods for preparing a formulation according to the present invention may encompass further steps, such as filling it into vials suitable for clinical use, such as sealed containers and/or confectioning it in a dosage unit form. The methods may also comprise further steps such as spray-drying, lyophilization, or freezing, e.g. bulk freezing. The invention also encompasses the containers, dosage unit forms, or other products obtainable by any of the methods recited herein.

The formulations of the present invention can be used to store the polypeptides of the invention, e.g. polypeptides comprising at least one ISVD against vWF, such as ALX 0081 or ALX 0081-A, as defined herein. Thus, the invention encompasses a method of storage of the polypeptides of the invention as used herein, characterized by the use of a formulation as defined herein. More specifically, the invention encompasses methods for stabilizing the polypeptides of the invention for storage, comprising e.g. the preparation of a formulation as described herein. Storage can be 1-36 months, such as 1, 1.5, 3, 6, 9, 12, 18, 24, 30 or 36 months, e.g. at least 12 months, optionally at a temperature between −70° C. and +40° C., such as −70° C., −20° C., +5° C., +25° C. or +40° C., preferably a temperature between −70° C. and +25° C., more preferably a temperature between −20° C. and +5° C. Thus, storage may encompass freezing, freeze-drying (lyophilization) and/or spray-drying. The storage methods may furthermore comprise the assessment of physical and chemical integrity of the vWF binders as defined herein.

The present invention also relates to methods for analyzing formulations comprising at least one of the vWF binders as defined herein. The formulations can be analyzed for any signs of chemical or physical instability of the vWF binders as defined herein. For example, the formulations can be assessed for the presence of degradation products, e.g. low molecular weight derivatives such as proteolytic fragments; and/or for chemical derivatives, e.g. pyroglutamate variants; and/or for high molecular weight derivatives such as aggregates, agglomerates, etc. The formulation can also be assessed for total protein content and/or potency. Each of the various assay methods as referred to herein can be used in the analysis method of the present invention.

Thus, the present invention also relates to a method for monitoring and/or assessing the quality and/or stability of a formulation, e.g. during one or more of manufacture, storage and use. The invention also relates to a method of quality control of a formulation, e.g. to assess that the formulation meets product specifications as further described herein. The invention in any of these aspects comprises one or more selected from the comparison with one or more reference samples, the analysis of batch to batch variation, and the ongoing monitoring of a production process.

The present invention relates to any product that is associated with the formulations of the present invention, e.g. by comprising them, or by being necessary for their production or confectioning, without any limitations.

For example, the present invention relates to an article of manufacture, e.g. a sealed container comprising one or more of the formulations according to the present invention.

The invention also relates to a pharmaceutical unit dosage form, e.g. a dosage form suitable for parenteral administration (e.g., intradermally, intramuscularly, intraperitoneally, intravenously and subcutaneously) to a patient, preferably a human patient, comprising one or more of the formulation according to any embodiment described herein.

The dosage unit form can be e.g. in the format of a prefilled syringe, an ampoule, cartridge or a vial.

Also provided are kits or articles of manufacture, comprising the formulation of the invention and instructions for use by, e.g., a healthcare professional. The kits or articles of manufacture may include a vial or a syringe containing the formulation of the invention as described herein.

Preferably, the vial or syringe is composed of glass, plastic, or a polymeric material chosen from a cyclic olefin polymer or copolymer. The syringe, ampoule, cartridge or vial can be manufactured of any suitable material, such as glass or plastic and may include rubber materials, such as rubber stoppers for vials and rubber plungers and rubber seals for syringes and cartridges. The invention also relates to a kit comprising one or more of the formulations according to the present invention. The kit may further comprise instructions for use and/or a clinical package leaflet. In any embodiment of the products as defined herein, the invention also encompasses the presence of packaging material, instructions for use, and/or clinical package leaflets, e.g. as required by regulatory aspects.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

The present invention also relates to a method of treating or preventing a vWF-related disease, such as e.g. acute coronary syndrome (ACS), transient cerebral ischemic attack, unstable or stable angina pectoris, stroke, myocardial infarction or thrombotic thrombocytopenic purpura (TTP); said method comprising administering to a subject a pharmaceutical composition comprising the formulation of the invention, thereby reducing one or more symptoms associated with said vWF-related disease. In particular, said vWF-related disease is TTP.

In another embodiment of the invention, an article of manufacture containing materials useful for the treatment of a disease as described above is provided. The article of manufacture comprises a contained, a label and a package insert. Suitable containers include, for example, bottles, vials, syringes, etc. The containers may be of a variety of materials such as glass or plastic. The container holds the composition which is effective in treating the condition and may have a sterile access port (for example the container may be an intravenous solution bag or a vial having a stopper pierceable by a hypodermic injection needle). At least one active agent in the composition is the polypeptide of the invention, such as ALX 0081 or ALX 0081-A. The label on, or associated with, the container indicates that the composition is used for treating the condition of choice. The article of manufacture may further comprise a second container comprising a pharmaceutically acceptable buffer, such as a phosphate buffer saline or a citrate buffered saline as described herein. It may further include other materials desirable from a user or commercial standpoint, including other buffers, diluents, filters, needles and syringes.

The present invention provides a kit or an article of manufacture, comprising a container containing the polypeptide as described herein or the formulation as described herein, and instructions for use.

The present invention provides a kit or article of manufacture as described herein, wherein the formulation is present in a vial or an injectable syringe.

The present invention provides a kit or article of manufacture as described herein, wherein the formulation is present in a prefilled injectable syringe.

The present invention provides a kit or article of manufacture as described herein, wherein the syringe or a vial is composed of glass, plastic, or a polymeric material chosen from a cyclic olefin polymer or copolymer.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

5. ABBREVIATIONS

A list of explanations of commonly used abbreviations in the present specification is provided in Table 5.

6. LEGEND TO THE FIGURES

FIG. 1. Time to Confirmed Normalization of Platelet Count in the Intention-to-Treat Population. Data from the double blind daily plasma exchange period up to the cut-off point were used for the analysis of the primary endpoint. The data cut-off point was defined by: 45 days of daily plasma exchange after the start of study drug, the stop of daily plasma exchange, or the stop of study drug treatment; whichever occurred first.

FIG. 2. ADAMTS13 Activity According to Recurrences. Panels A and B show ADAMTS13 activity categories for individual patients in the week after end of daily plasma exchange, and at the end of study drug treatment, respectively. In each panel, ADAMTS13 categories (suppressed ≤10%, or normalized >10%) for patients in the different treatment groups are presented. The left part of each panel indicates data for patients who had no recurrence, the right part of each panel indicates patients who had a recurrence and when in relation to the end of daily PE or end of treatment this occurred.

FIG. 3. Mean vWF:Ag levels vs time profiles during a 7 days repeated subcutaneous 10 mg daily dosing of caplacizumab in healthy volunteers (upper panel), and during repeated subcutaneous daily administration of 10 mg caplacizumab in aTTP patients (lower panel). aTTP: acquired thrombotic thrombocytopenic purpura; PE: plasma exchange; FU: follow-up; vWF: von Willebrand factor.

FIG. 4. Mean (±SD) RICO activity in the phase II ALX-0681-2.1/10 ("TITAN", upper panel) and the phase III ALX0681-C301 ("HERCULES", lower panel). RICO values of <20% represent the threshold for pharmacological activity of caplacizumab; for the purpose of the graph, values below the lower limit of quantification of 15% were set at 15%, values above the upper limit of quantification of 120% were set at 120%. Graphs shows mean±standard error of the mean. PE: plasma exchange; FU: follow-up; RICO: ristocetin cofactor; SD: standard deviation; vWF: von Willebrand factor.

FIG. 5. Caplacizumab plasma concentration versus time profile after administration of single ascending subcutaneous doses (A), and after single and repeated administration of 10 mg daily subcutaneous doses for seven days (B) in healthy volunteers.

7. EXAMPLES

7.1 Applicable Regulations

All human samples used in the Examples section were either obtained from commercial sources or from human volunteers (after all required consents and approvals were obtained) and were used in according with the applicable legal and regulatory requirements (including those regarding medical secret and patient privacy).

Clinical trials were performed in accordance with applicable laws and regulations (including the Declaration of Helsinki and the principles of medical secret and the protection of patient privacy) and after all required approvals (including approvals by relevant ethics committees) and consents (including informed consent of subjects involved) were obtained.

The objectives and contents of this clinical study as well as its results were treated as confidential and have not been made accessible to third parties. Employees participating in the study were bound by confidentiality. All unused drugs were either returned to the applicant or destroyed.

7.2 Eligibility Criteria

Patients had to fulfill all of the following criteria to be eligible for study admission in the phase III study:

Inclusion Criteria
1. Adult male or female 18 years of age at the time of signing the informed consent form (ICE) 2. Clinical diagnosis of acquired TTP, which included thrombocytopenia and microscopic evidence of red blood cell fragmentation (e.g., schistocytes)
3. Requires initiation of daily PE treatment and has received 1 PE treatment prior to randomization Exclusion Criteria Platelet count ≥100×10$^9$/L Serum creatinine level >200 μmol/L in case platelet count is >30×10$^9$/L (to exclude possible cases of atypical Hemolytic Uremic Syndrome [atypical HUS])

Known other causes of thrombocytopenia including but not limited to:
  Clinical evidence of enteric infection with *E. coli* 0157 or related organism—Atypical HUS
  Hematopoietic stem cell, bone marrow or organ transplantation-associated thrombotic microangiopathy
  Known or suspected sepsis
  Diagnosis of disseminated intravascular coagulation Congenital TTP (known at the time of study entry)

Pregnancy or breast-feeding

Clinically significant active bleeding or high risk of bleeding (excluding thrombocytopenia)

Known chronic treatment with anticoagulant treatment that cannot be stopped (interrupted) safely, including but not limited to:
  vitamin K antagonists
  heparin or low molecular weight heparin (LMWH)
  non-acetyl salicylic acid non-steroidal anti-inflammatory molecules Malignant arterial hypertension Clinical condition other than that associated with TTP, with life expectancy <6 months, such as end-stage malignancy Subjects who were previously enrolled in a clinical study with caplacizumab and received caplacizumab or for whom the assigned treatment arm is unknown.

7.3 Study Design

The present study was designed as a phase III, double blind, placebo-controlled, randomized study to evaluate the efficacy and safety of caplacizumab treatment when administered in addition to standard of care treatment in subjects with an acute episode of acquired TTP (Hercules). The study evaluated the efficacy of caplacizumab in more rapidly restoring normal platelet counts and the effect of treatment with caplacizumab on a composite endpoint of TTP-related mortality, prevention of recurrence of the presenting TTP episode and prevention of major thromboembolic events (TE) during study drug treatment. After confirmation of eligibility to study participation (cf. Example 7.2) and after the start of PE treatment, subjects were randomized in a ratio of 1:1 receiving either caplacizumab or placebo in addition to standard of care therapy. Randomization was stratified by severity of neurological symptoms (Glasgow coma scale [GCS]).

The study duration per subject was approximately 2 months up to approximately 6 months in case of treatment extension and exacerbation during the 30-days post-daily PE period or relapse during treatment extension.

The patients were followed in different phases during this study:

Screening period: From signing of Informed Consent Form (ICF) until randomization;

Study drug treatment period: Covering daily PE period (variable duration) and 30-days post-daily PE period;

Treatment extension period: 7-day extensions with maximum of 28 days, i.e., 4×7 days;

Open-label: In case an exacerbation during the 30 day treatment period or a relapse during the treatment extension period occurred (first exacerbation or relapse), the subject received open label (OL) caplacizumab together with re-initiation of daily PE and optimized immunosuppressive treatment. Caplacizumab treatment schedule and visit schedule was the same as for the initial study drug treatment period (covering daily PE [variable duration] and 30-days post-daily PE period) and the possible treatment extension period;

Follow-up (FU) period of 4 weeks: A first FU visit 7 days and a final FU visit 28 days after the last day of study drug administration.

The patients received the best medical care and treatment judged appropriate by the investigator at each site and according to the guidelines for treatment of TTP.

The study drug was administered as an adjunctive treatment at specific times relative to PE procedures. The study drug consisted of 10 mg of caplacizumab ("treatment group" or "CAPLA") or placebo ("placebo group"), once or twice daily.

7.4 Study Drug Treatment for the Hercules Study:

Loading i.v. dose: subjects received a single loading dose of 10 mg study drug by i.v. bolus injection from 6 hours to 15 minutes prior to the first PE done after randomization; an i.v. bolus of 10 mg was also given prior to the $1^{st}$ PE done for treatment of a first exacerbation or relapse.

Daily subcutaneous (s.c.) dose: after completing each daily PE, a s.c. injection of 10 mg study drug was administered daily throughout the full duration of PE treatment.

Daily s.c. administration of 10 mg study drug was continued for a period of 30 days after stop of daily PE. No adjustment to this period was made for tapering of PE.

Study drug treatment extension beyond these 30 days was guided by a number of risk factors for relapse of the presenting TTP episode, including ADAMTS13 activity profile as well as other signs and symptoms of continued underlying disease activity.

In case of a first exacerbation of the presenting TTP episode, subjects received open label caplacizumab together with daily PE.

In case a subject has a first TTP recurrence while still receiving study drug in the treatment extension period, then daily PE was started as part of standard of care treatment together with appropriate immunosuppressive treatment.

In case a subject had a first or subsequent TTP relapse after completing study drug treatment (i.e., in the FU period), standard of care treatment of daily PE and appropriate immunosuppressive treatment was initiated as per site practice.

7.5 Endpoints

The primary endpoint of this phase III study was the time to platelet count response defined as initial platelet count $\geq 150 \times 10^9/L$ with subsequent stop of daily PE within 5 days. Key secondary endpoints are listed below:

1. Proportion of subjects with TTP-related death, a recurrence of TTP, or at least one treatment-emergent major thromboembolic event (e.g., myocardial infarction, cerebrovascular accident, pulmonary embolism or deep venous thrombosis [DVT]) during the study drug treatment period (including extensions).
2. Proportion of subjects with a recurrence of TTP in the overall study period (including 4-week FU period).
3. Proportion of subjects with refractory TTP, defined in the study as absence of platelet count doubling after 4 days of standard treatment, and LDH>ULN.
4. Time to normalization of all 3 of the following organ damage marker levels: Time to LDH≤1× upper limit of normal (ULN), and cTnI≤1×ULN, and serum creatinine ≤1×ULN
5. Other endpoints included duration and volume of plasma exchange, duration of hospital and intensive care unit stay, mortality, pharmacodynamic and pharmacokinetic parameters, and immunogenicity.
6. Safety assessments were performed during the study drug treatment and follow-up periods, and included vital signs, physical examination, clinical laboratory tests, and 12-lead electrocardiogram. Reported adverse events were coded with the use of preferred terms from the Medical Dictionary for Regulatory Activities, Version 20.0.

7.6 Statistical Analysis

In the Hercules study, the planned sample of 132 patients was specified to provide a power of 80% to detect a 40% reduction in the median time to platelet count normalization with caplacizumab, using a two-sided log-rank test at a 5% significance level, assuming a 10% dropout rate. A sample size of 132 subjects was also set to provide a 83% power to detect a 20% reduction in the first key secondary endpoint, using a two-sided chi-squared test with a large sample approximation and a 5% significance level. All efficacy analyses were performed on the intention-to-treat population (consisting of all randomized patients), and safety and immunogenicity analyses were performed on the safety population (consisting of all patients who received at least one dose of study drug). Time to platelet count response in the caplacizumab and placebo groups was compared by conducting a two-sided stratified log-rank test based on a Kaplan-Meier analysis, with severity of neurological involvement as a stratification factor.

A fixed sequence approach was applied for analyses of the key secondary endpoints. TTP-related death, major thromboembolic event and TTP recurrence (exacerbation) were analyzed using a Cochran-Mantel-Haenszel test with adjustment for severity of neurological involvement, while the fourth, time to normalization of organ damage markers, was analyzed using a stratified log-rank test based on a Kaplan-Meier analysis with adjustment for baseline severity of neurological involvement and LDH.

7.7 Determination of ADAMTS13 Activity

ADAMTS13 activity and functional inhibitor activity were measured by a fluorogenic assay using the FRETS- VWF73 substrate (Kokame et al. 2005. Br J Haematol 129(1):93-100; Kremer Hovinga et al. 2006 J Thromb Haemost 4(5):1146-8).

Briefly, the FRETS-VWF73 assay were performed essentially as described (Kokame et al. 2005 supra) with the following modifications: Pefabloc SC (Boehringer, Mannheim, Germany) was added to the assay buffer (5 mmol L-1 Bis-Tris, 25 mmol L-1 CaCl2), 0.005% Tween-20, pH 6.0) at a final concentration of 1 mmol L-1. Assay calibration was obtained by using a normal human plasma pool (NHP; Swiss Red Cross Blood Services, Bern, Switzerland) diluted 1:25 (100%) in assay buffer. Further calibration samples were obtained by serial predilutions of NHP of 3:4 (75%), 1:2 (50%), 1:4 (25%), 1:10 (10%), 1:20 (5%), 1:50 (2%) and 1:100 (1%) in heat-inactivated NHP, incubated for 30 min at 56° C. followed by 15 min of centrifugation at 15 000×g) to correct for a plasma matrix effect in the lower activity range of the standard curve. All of these standard samples as well as heat-inactivated NHP (0% ADAMTS13 activity) and all test samples were subsequently diluted 1:25 in assay buffer. Next, 25 μL of each diluted standard or patient sample was incubated at 37° C. in a 384-well white plate (NUNC, Roskilde, Denmark). After 10 min, 25 μl of 4 μmol L-1 FRETS-VWF73 peptide substrate dissolved in assay buffer was added to each well and evolution of fluorescence recorded at 37° C. in a fluorescence microplate reader (GENios, Tecan, Zürich, Switzerland) equipped with a 340 nm excitation filter (band width 35 nm) and a 450 nm emission filter (band width 25 nm). Fluorescence evolution was measured over time (every 5 min for 42 cycles). The reaction rate was calculated by linear regression analysis (Passing-Bablok) of fluorescence evolution over time from 5 (cycle 2) to 60 min (cycle 13). The slope of the regression curve was calculated for each calibration sample, and used to generate the calibration curve (trend line: y=ax+b; with x=ADAMTS13(%) and y=delta RFU/delta time). The ADAMTS13 activity (%) of a sample was then calculated as: (y−b)×1/a.

ADAMTS13 functional inhibitor activity was measured by the same fluorogenic FRETS-VWF73 method by determination of residual ADAMTS13 activity of normal human plasma after 1:1 (v:v) incubation for 2 hours at 37° C. with heat-inactivated patient's plasma (30 min at 56° C.).

For each analytical batch, a calibration curve was generated using a normal human plasma pool (NHP; Swiss Red Cross Blood Services, Bern, Switzerland) diluted 1:25 (100%) in assay buffer. Further calibration samples were obtained by serial predilutions of NHP of 1:2 (50%), 1:4 (25%), 1:10 (10%), 1:20 (5%), 1:50 (2%) and 1:100 (1%) in heat-inactivated NHP. All calibration points were applied in singlicate. Acceptance criteria: (1) The slope of the final regression of the standard curve line has to be >6.0; and (2) $R^2$ of the regression of the final plot has to be >0.98 (or R>0.9899). Otherwise, the assay was rejected.

7.8 Study Population

In the present Hercules study, 145 patients were randomly assigned to receive caplacizumab (n=72) or placebo (n=73). All patients received study drug, except for one patient in the caplacizumab group, who withdrew consent prior to first dosing. Overall, 108 patients completed the study (i.e., completed all scheduled treatment visits and had their final follow-up visit), while 37 patients discontinued from the study (14 in the caplacizumab group, 23 in the placebo group). The most frequent reasons for study discontinuation were adverse events, withdrawal of consent and physician's decision.

Demographics and baseline disease characteristics were generally similar in the 2 study groups (Table 7.8), except for previous TTP episodes and ADAMTS13 activity. In total, 97% (140/145) of patients received glucocorticoids and in 24% of them ($^{35}/_{145}$), treatment with rituximab was initiated during daily plasma exchange (17% or $^{12}/_{72}$ in the caplacizumab group and 32% or $^{23}/_{73}$ in the placebo group).

TABLE 7.8

Demographics and Baseline Disease Characteristics* in the Intention-to-Treat Population

| Characteristic | Caplacizumab (N = 72) | Placebo (N = 73) | Total (N = 145) |
|---|---|---|---|
| Mean age (range) - yr | 45 (18-77) | 47 (21-79) | 46 (18-79) |
| Female sex - no. (%) | 49 (68) | 51 (70) | 100 (69) |
| Mean Body Mass Index (range) - kg/m² | 30 (18-53) | 30 (19-59) | 30 (18-59) |
| Race or ethnic group - no. (%)§ | | | |
| White | 47 (68) | 50 (78) | 97 (73) |
| Black | 15 (22) | 13 (20) | 28 (21) |
| Asian | 4 (6) | 0 | 1 (1) |
| Hispanic or Latino | 4 (6) | 2 (3) | 6 (4) |
| Presenting episode of TTP - no. (%) | | | |
| Initial | 48 (67) | 34 (47) | 82 (57) |
| Recurrent | 24 (33) | 39 (53) | 63 (43) |
| Mean platelet count (range) - 10⁹/L | 32 (3-119) | 39 (9-133) | 24 (3-133) |
| Mean LDH (range) - U/L | 613 (120-2525) | 517 (151-3343) | 565 (120-3343) |
| Mean cTnI (range) - μg/L | 3.46 (0.01-75.96) | 0.63 (0.01-7.28) | 2.05 (0.01-75.96)) |
| Serum creatinine (range) - μmol/L | 100 (35-717) | 102 (52-482) | 101 (35-717) |
| ADAMTS13 activity - no. (%)¶ | | | |
| <10% | 58 (82) | 65 (90) | 123 (86) |
| ≥10% | 13 (18) | 7 (10) | 20 (14) |
| missing | 1 | 1 | 2 |

TABLE 7.8-continued

Demographics and Baseline Disease Characteristics* in the Intention-to-Treat Population

| Characteristic | Caplacizumab (N = 72) | Placebo (N = 73) | Total (N = 145) |
|---|---|---|---|
| Glasgow Coma Scale Score - no. (%) | | | |
| ≤12 | 6 (8) | 5 (7) | 11 (8) |
| 13-15 | 65 (91) | 67 (93) | 132 (92) |
| missing | 1 | 1 | 1 |

*Baseline was defined as before the first administration of the study drug; all patients were to have a prior PEX before baseline.
§Race and ethnic group were determined by the investigator.
¶As a result of the prior PEX, in some cases baseline ADAMTS13 activity was higher than measured locally on admission. Where available, locally measured ADAMTS13 activity levels on admission were collected and the lower of the baseline and admission values is represented.

7.9 Primary and Key Secondary Endpoints

There was a significant reduction in time to platelet count response in the caplacizumab group based on the Kaplan Meier analysis and a stratified log-rank test (FIG. 1). At any given time point, patients receiving caplacizumab were 1.55 times more likely to achieve a platelet count response compared to patients treated with placebo (platelet count normalization ratio, 1.55; 95% CI, 1.09 to 2.19; P=0.01). During the study drug treatment period, treatment with caplacizumab resulted in a 74% reduction in the number of patients with TTP-related death, recurrence of TTP, or a major thromboembolic event (P<0.0001, Table 7.9). During the overall study period, including the 28-day treatment-free follow-up period, 28 patients in the placebo group experienced a recurrence versus 9 patients in the caplacizumab group, a 67% reduction (P<0.001, Table 7.9). In all 6 patients in the caplacizumab group who experienced a recurrence of TTP during the follow-up period (i.e., a relapse, at more than 30 days after end of daily plasma exchange), the ADAMTS13 activity level was <10% at the end of the study drug treatment, suggesting the underlying disease was still active at the time study drug was stopped. No caplacizumab-treated patient was refractory to therapy, while 3 patients on placebo were (P=0.057). Treatment with caplacizumab was also associated with a trend toward faster normalization of the 3 organ damage markers: LDH, cTnI, and serum creatinine.

TABLE 7.9

Primary and Key Secondary Efficacy Endpoints in the Intention-to-Treat Population

| Endpoint | Caplacizumab (N = 72) | Placebo (N = 73) |
|---|---|---|
| Primary endpoint | | |
| Time to response: caplacizumab vs. placebo | | |
| Platelet count normalization ratio (95% CI) | 1.55 (1.09-2.19) | |
| P value | 0.01 | |
| Key secondary endpoints | | |
| At least one of the events below while on blinded study drug treatment - no. (%) | 9 (12.7) | 36 (49.3) |
| TTP-related death | 0 | 3 (4.1) |
| major thromboembolic event | 6 (8.5) | 6 (8.2) |
| TTP recurrence (exacerbation) | 3 (4.2) | 28 (38.4) |
| P value | <0.0001 | |
| TTP recurrence* during the entire study period - no. (%) | 9 (12.7) | 28 (38.4) |
| while on blinded study drug (exacerbation) | 3 (4.2) | 28 (38.4) |
| during the follow-up period (relapse) | 6 (9.1) | 0 |
| P value | <0.001 | |
| Refractory§ to treatment - no. (%) | 0 | 3 (4.2) |
| P value | 0.0572 | |
| Time to normalization of organ damage markers | | |
| Median time - days (95% CI) | 2.86 (1.93-3.86) | 3.36 (1.88-7.71) |

*Recurrence was defined as a new drop in platelet count after initial platelet count normalization, necessitating re-initiation of PEX. According to consensus terminology, recurrences within 30 days after end of daily PEX are exacerbations, while those occurring more than 30 days after end of daily PEX are termed relapses (Scully et al., 2017 J Thromb Haemost 5:312-22).
§For this endpoint, refractoriness was defined as absence of platelet count doubling after 4 days of treatment and LDH above normal levels (Benhamou et al. 2015 J Thromb Haemost 13:293-302).

7.10 ADAMTS13 Activity in Relation to Recurrence

Exacerbation: Of the 145 patients randomized in the present Hercules study, 129 achieved a platelet count response and completed the daily plasma exchange period (65 in the caplacizumab arm and 64 in the placebo arm). In the week after daily plasma exchange was ended, ADAMTS13 activity had returned to above 10% in 42% ($54/129$) of patients, but remained suppressed below 10% in the other 58% ($75/129$). In total, 31 patients experienced an exacerbation, 2 of whom had normalized ADAMTS13 activity and 29 of whom had unresolved underlying disease as evidenced by ADAMTS13 activity levels <10% (FIG. 2, panel A).

Relapse: ADAMTS13 activity levels at the end of study drug treatment were available for 120 patients (60 at the end of double-blind caplacizumab treatment, 34 at the end of double-blind placebo treatment, and 26 at the end of open-label caplacizumab treatment). Of these patients, 74% ($89/120$) had normalized ADAMTS13 activity levels by the time treatment was stopped. None of these patients suffered a relapse during the 28-day follow-up after end of study drug treatment. The other 26% ($31/120$) of patients still had suppressed ADAMTS13 activity at the time study drug treatment was stopped. In total, 9 of these 31 patients suffered a relapse in the subsequent 28 days, 6 of the 9 after the end of double-blind caplacizumab treatment and 3 of the 9 after the end of open-label caplacizumab treatment (FIG. 2, panel B)(cf. Example 7.13).

7.11 Characterization and Outcomes of aTTP Patients with Initial or Recurrent Disease Background: Acquired thrombotic thrombocytopenic purpura (aTTP) is a life-threatening autoimmune blood clotting disorder. Patients are at risk for significant morbidity and death during each episode. Efficacy and safety data were obtained in the Phase III Hercules study with caplacizumab in patients with aTTP (Scully et al., Blood 2017 130:LBA-1).

Aims: Characterization of disease presentation and evaluation of treatment outcomes in patients enrolled in the HERCULES study with an initial or recurrent aTTP episode.

Methods: Demographics, baseline disease characteristics, and treatment outcomes (time to platelet count response, mortality, recurrence, major thromboembolic events (TE) and refractoriness) were evaluated for both subgroups using descriptive summaries. Platelet count, LDH levels and cardiac Troponin-I levels were determined according to standard methods (cf. detailed description).

Results: 145 patients were randomized, 82 with an initial aTTP episode and 63 with recurrent disease. Demographics were generally balanced between groups, whereas baseline disease characteristics were more severe in initial vs. recurrent episodes: mean platelet count ($28.8 \times 10^9$/L vs. $44.4 \times 10^9$/L), mean LDH (598 U/L vs. 523 U/L) and median cardiac Troponin-I (0.119 μg/L vs. 0.036 μg/L). The time from first symptoms until diagnosis was also longer in those experiencing an initial episode (6.5 days) vs. a recurrent one (3.9 days). More patients in the caplacizumab group had their first aTTP episode (66.7%) vs. the placebo group (46.6%). Treatment with caplacizumab improved outcomes [i.e., faster time to platelet count response, lower proportion of patients with either death, recurrence or a major TE event during the treatment period, lower recurrence rate during the overall study period, and prevention of refractoriness] in both subgroups compared to placebo (see Table 7.11 for detailed results).

Conclusions: Patients with an initial aTTP episode have a delayed presentation and more severe disease at baseline than those with recurrent disease. Treatment with caplacizumab improves outcomes in both subgroups.

TABLE 7.11

Efficacy outcomes by previous TTP episode
(Intention-to-treat population)

| | Initial Episode | | Recurrent Episode | |
|---|---|---|---|---|
| Efficacy outcomes | Caplacizumab N = 48* | Placebo N = 34 | Caplacizumab N = 24 | Placebo N = 39 |
| Time to platelet count response | | | | |
| Platelet count normalization rate ratio (95% CI) | 1.67 (1.025 to 2.722) | | 1.64 (0.951 to 2.818) | |
| TTP related death, recurrence of TTP or a major TE event during the study drug treatment period | 6 (12.8) | 19 (55.9) | 3 (12.5) | 17 (43.6) |

TABLE 7.11-continued

Efficacy outcomes by previous TTP episode
(Intention-to-treat population)

| | Initial Episode | | Recurrent Episode | |
|---|---|---|---|---|
| Efficacy outcomes | Caplacizumab N = 48* | Placebo N = 34 | Caplacizumab N = 24 | Placebo N = 39 |
| Recurrence of TTP during Overall Study period - n (%) | 6 (12.8) | 15 (44.1) | 3 (12.5) | 13 (33.3) |
| Refractory TTP - n (%) | 0 | 1 (2.9) | 0 | 2 (5.1) |

*percentages are based on 47 patients (1 subject withdrew consent prior to study drug treatment)

7.12 Treatment of Acquired TTP with an Anti-vWF Nanobody Results in Significant Reduction in Healthcare Resource Utilization Background: The efficacy and safety of caplacizumab, an anti-von Willebrand Factor (vWF) Nanobody, for the treatment of acquired thrombotic thrombocytopenic purpura (aTTP) were evaluated (Scully et al., Blood 2017 130:LBA-1).

Aims: To investigate the effect of treatment with caplacizumab on healthcare resource utilization: plasma exchange (PE) parameters, days spent in the hospital and in the intensive care unit (ICU).

Methods: Volume and days of PE, days in hospital and ICU were summarized and compared between the caplacizumab and placebo arms for the overall study drug treatment period, using a normal approximation to the Wilcoxon Rank Sum test.

Results: 145 patients were randomized in the Hercules study, 73 to placebo and 72 to caplacizumab. Treatment with caplacizumab led to faster normalization of platelet counts, prevented exacerbations, and prevented patients from becoming refractory to treatment. This was reflected in a 38% reduction in mean (±SE) number of PE days in the caplacizumab (n=71) vs. placebo group (n=73): 5.8 (±0.51) days vs. 9.4 (±0.81) days (p<0.001). The mean (±SE) total volume of plasma exchanged was similarly reduced by 41%: 21.3 (±1.6) L vs. 35.9 (±4.2) L (p<0.001). Average duration of hospitalization (±SE) was decreased by 31% in the caplacizumab (n=71) vs. placebo group (n=73): 9.9 (±0.7) days vs. 14.4 (±0.7) days (p=0.0025).

A third of the patients were admitted to the ICU (28 patients in the caplacizumab group, and 27 patients in the placebo group). In the caplacizumab group, the mean (±SE) number of days spent in the ICU was reduced by 65%: 3.4 (±0.4) days vs. 9.7 (±2.1) days (p=0.0098).

Conclusions: Caplacizumab, through rapid blocking of vWF-mediated platelet adhesion, represents a novel treatment for aTTP. Treatment with caplacizumab results in improved outcomes as reflected by meaningful reductions in healthcare resource utilization.

7.13 Efficacy and Safety of Open-Label Caplacizumab in Patients with Exacerbations of aTTP Background: The efficacy and safety of caplacizumab in patients with acquired Thrombotic Thrombocytopenic Purpura (aTTP) have been demonstrated in a single-blind phase 2 study (Peyvandi et al., 2016 N Engl J Med 374:511-522) and confirmed in a double-blind phase 3 study (Scully et al., Blood 2017 130:LBA-1).

Aims: Herein we present the efficacy and safety results of patients who received open-label (OL) caplacizumab.

Methods: In case of a recurrence during the double-blind (DB) treatment period, patients were switched to OL caplacizumab, together with re-initiation of daily plasma exchange (PEX) and immunosuppression, while maintaining the blind for the initial treatment allocation. Platelet counts were determined according to standard methods (cf. detailed description). ADAMTS13 activity as determined as described in Example 7.7.

Results: 31 patients experienced an exacerbation during the DB period, 28 in the placebo group and 3 in the caplacizumab group. 28 of them were switched to OL treatment with caplacizumab (26 of the 28 placebo-treated patients and 2 of the 3 caplacizumab-treated patients). By day 6, 81% of patients receiving OL caplacizumab achieved a confirmed platelet count response (i.e., platelet count ≥150×10$^9$/L confirmed by stop of daily PE within 5 days). There were no deaths. One patient (3.6%) experienced a TTP exacerbation and 1 patient (3.6%) experienced a major thromboembolic event (vena cava thrombosis) during the OL treatment period. After the end of OL treatment, 3 patients had a recurrence of TTP and all 3 had ADAMTS13 activity <10% when the treatment was stopped. The safety profile in the OL caplacizumab group was consistent with that observed in the DB caplacizumab group. In total, 25 patients (89.3%) were reported with at least one treatment-emergent adverse event.

Conclusions: Open-label therapy with caplacizumab was efficacious in patients who experienced an exacerbation of aTTP. The safety profile was consistent with that observed in the double-blind period (cf. Example 7.14).

7.14 Overall Study Period: Safety and Immunogenicity.

Due to the Hercules study design (which included a switch to treatment with open-label caplacizumab in case of TTP recurrence while on double-blind study drug), and almost all recurrences in the placebo group (cf. Example 7.13), the median duration of exposure was longer in the caplacizumab group than in the placebo group: 35 (range 1 to 65) versus 23 (range 2 to 66) days.

During the overall study period, 69 patients (97.2%) in the caplacizumab group and 71 patients (97.3%) in the placebo group reported at least one adverse event. Adverse events were considered at least possibly related to study drug by the investigator in 41 patients (57.7%) in the caplacizumab group and 32 patients (43.8%) in the placebo group.

Four patients had an adverse event leading to death during the study, 1 (1.4%) in the caplacizumab group (during the treatment-free follow-up period, considered by the investigator as not related to study drug), and 3 (4.1%) in the placebo group (all during the study drug treatment period).

Serious adverse events were reported for 28 patients (39.4%) in the caplacizumab group and 39 patients (53.4%) in the placebo group during the overall study period. Per protocol, recurrences had to be reported as serious adverse events, and were numerically the main driver in the placebo group. Serious adverse events were considered at least possibly related to study drug by the investigator in 10 patients (14.1%) in the caplacizumab group and 4 patients (5.5%) in the placebo group.

Five patients in the caplacizumab group and 9 subjects in the placebo group were reported with an adverse event leading to study drug discontinuation.

Bleeding-related adverse events were reported for 46 patients (64.8%) in the caplacizumab group, and 35 patients (47.9%) in the placebo group. The most frequent were epistaxis and gingival bleeding; all of these resolved, most of them without intervention. These events were mild or moderate in the majority of patients, and severe in 3 patients on caplacizumab and 1 patient on placebo. Serious adverse events of bleeding were reported in 8 patients (11.3%) on caplacizumab and one patient (1.4%) on placebo. The most frequently reported serious adverse event of bleeding was epistaxis, in 4 patients in the caplacizumab group.

Drug-induced anti-drug-antibodies developed in 3.1% of patients treated with caplacizumab. No impact on clinical efficacy was observed and no serious adverse events were reported in these patients (cf. Example 7.21).

7.15: Pharmacodynamics of Caplacizumab

The interaction of caplacizumab with vWF is highly specific, and binding of caplacizumab to the vWF A1 domain does not affect the capacity of vWF to interact with coagulation factor VIII (FVIII), for which vWF has a carrier function. Similarly, the selective binding of caplacizumab does not affect the capacity of vWF to interact with fibrillar collagens, collagen type VI or ADAMTS13. Moreover, caplacizumab does not cross react with erythrocytes or platelets. Due to this high specificity, off-target effects were not expected and have not been observed in preclinical studies and clinical trials.

Levels of total (free+drug-complexed) vWF, ristocetin cofactor activity (RICO) and FVIII levels were measured in healthy volunteers after single ascending intravenous or subcutaneous administration and multiple 10 mg daily subcutaneous administration, and in aTTP patients after multiple 10 mg once daily subcutaneous doses or placebo following an initial 10 mg intravenous bolus or placebo.

7.15.1 vWF Antigen (vWF:Ag)

At baseline, vWF:Ag levels were higher in aTTP patients than in healthy subjects. In clinical studies conducted with caplacizumab, the mean (±standard deviation [SD]) plasma vWF:Ag levels were 38.5±10.9 nM in healthy subjects and 70.5±30.0 nM in aTTP patients. Caplacizumab treatment impacted vWF disposition, resulting in a transient reduction of total circulating vWF:Ag levels. On average, this effect was reversed within 2 to 7 days after final dose administration in healthy volunteers and aTTP patients (FIG. 3).

The transient decrease of total vWF:Ag levels was attributed to a faster elimination of the drug-target complex compared to the free target.

7.15.2 RIPA/RICO

The ristocetin platelet aggregation (RIPA) and RICO assays are in vitro assays to evaluate the platelet binding capacity of vWF present in the blood. The RIPA and RICO assay methodology is based on addition of ristocetin to plasma in the presence of platelets which causes platelet agglutination. The antibiotic ristocetin activates vWF to a similar extent as high shear blood flow conditions, and consequently modulates the binding of vWF to the platelet receptor GP1b. As in vitro platelet aggregation can be blocked by the interaction of caplacizumab with vWF, these methods were selected to evaluate the activity of caplacizumab during treatment. Full inhibition of vWF mediated platelet adhesion by caplacizumab was indicated by RIPA or RICO activity decreasing below 10% or 20%, respectively. Complete stable target inhibition for at least 24 hours was observed after a single subcutaneous dose of ≥10 mg in healthy volunteers. This 10 mg subcutaneous dose, given daily, also elicited full inhibition of vWF-mediated platelet adhesion in patients with aTTP throughout the complete treatment period (FIG. 4). In all clinical studies, the RICO activity recovered to baseline values within 7 days upon discontinuation of the study drug.

7.15.3 FVIII vWF acts as a carrier for FVIII. The modulation of total vWF levels by caplacizumab resulted also in a transient reduction of the levels of FVIII, and as for the vWF, the recovery of FVIII to normal ranges was observed within 2 to 7 days after final dose administration in healthy volunteers and aTTP patients.

7.15.4 QT/QTc Studies

No cardiovascular effect was observed in nonclinical studies. There was no evidence for clinically relevant electrocardiogram (ECG) findings in the completed human studies (cf. Example 7.13).

Given the molecular structure and size of caplacizumab, its target specificity, and the absence of in vivo cardiovascular liability, caplacizumab was not expected to prolong the QT interval.

This has not been observed.

7.16 Pharmacokinetics of Caplacizumab

Levels of total (free+target-bound) caplacizumab concentrations have been measured in plasma of healthy volunteers and aTTP patients. Full pharmacokinetic profiles were obtained in healthy subjects after single ascending intravenous infusions, and single and repeated subcutaneous dose administration (FIG. 5). Sparse plasma samples were obtained in aTTP patients in the phase II and phase III trials. The pharmacokinetic profile of caplacizumab has been investigated through standard non-compartmental analysis (NCA) in healthy volunteers, and in population pharmacokinetic analyses in healthy volunteers and aTTP patients.

After repeated 10 mg daily subcutaneous administration, steady-state was rapidly attained as of the second drug administration, with a limited accumulation of caplacizumab, dependent upon the expression of the target vWF:Ag.

7.16.1 Absorption

Main exposure parameters, estimated by standard non-compartmental methods after single dose in healthy volunteers or model-predicted at steady-state in aTTP patients, are reported in Tables 7.16.1A and 7.16.1B. After single dose administration, the extent (area under the curve; AUC) and rate of exposure (maximal concentrations; Cmax) increased with the administered dose, but not proportionally. After subcutaneous administration of 10 mg, caplacizumab Cmax was attained 4 h post-dose. The absolute bioavailability determined in the population pharmacokinetic analysis was estimated to 90% in aTTP patients, and close to 100% in healthy volunteers.

TABLE 7.16.1A

Pharmacokinetic parameters following single 10 mg intravenous or subcutaneous administration of caplacizumab in healthy volunteers.

| Parameter | Intravenous dose (n = 8) | Subcutaneous dose (n = 8) |
| --- | --- | --- |
| $T_{max}$, h | | |
| Median (range) | 0.26 (0.25 to 6) | 3.04 (3 to 9) |
| $C_{max}$, µg/ml | | |
| Mean (±SD) | 1.63 (±0.59) | 0.57 (±0.12) |
| $AUC_{inf}$, µg*h/ml | | |
| Mean (±SD) | 14.5 (±7.6) | 26.7 (±10.7) |

$AUC_{inf}$: area under the concentration-time curve extrapolated to infinity; $C_{max}$: maximum concentration; SD: standard deviation; $T_{max}$: time to $C_{max}$

TABLE 7.16.1B

Simulated mean steady-state pharmacokinetic exposure parameters (AUC, $C_{max}$, $C_{min}$ and $C_{avg}$) and corresponding pharmacodynamic effect (vWF:Ag change from baseline) following 40 days of 10 mg subcutaneous daily administration of caplacizumab in aTTP patients

| Parameter | Steady-state |
| --- | --- |
| $AUC_\tau$, µg*h/ml median ($5^{th}$-$95^{th}$ %) | 12.5 (7.03 to 23.1) |
| $C_{max}$, µg/ml median ($5^{th}$-$95^{th}$ %) | 0.609 (0.355 to 1.079) |
| $C_{min}$, µg/ml median ($5^{th}$-$95^{th}$ %) | 0.436 (0.230 to 0.843) |
| $C_{avg}$, µg/ml median ($5^{th}$-$95^{th}$ %) | 0.520 (0.293 to 0.960) |
| vWF:Ag change from baseline (%) | −43.8 (−67.7 to 0.5) | aTTP: acquired thrombotic thrombocytopenic purpura; $AUC_\tau$: area under the concentration-time curve over the dosing interval; $C_{avg}$: average concentration; $C_{max}$: maximum concentration; $C_{min}$: minimum concentration; vWF:Ag: von Willebrand factor antigen.

7.16.2 Distribution and Metabolism

Caplacizumab pharmacokinetics presented a biphasic plasma profile. A central volume of distribution of 5.35 and 6.33 L was estimated in healthy volunteers and aTTP patients, respectively, by the population pharmacokinetic model, while the peripheral volume of distribution was estimated to be 27 L.

Preclinical studies in cynomolgus monkeys indicated that in the systemic circulation caplacizumab binds and neutralizes its vWF activity within five minutes. The caplacizumab-vWF complex, the major circulating caplacizumab form, distributed to the liver, and similarly to the unbound vWF it was rapidly catabolized by the reticuloendothelial system. Preclinical studies suggested that the excess of unbound caplacizumab distributed to other well-perfused organs/tissues, where it is degraded by high capacity nonspecific catabolism. Free caplacizumab, with a MW of 28 KDa can be filtered through the glomerulus, although not freely. The renal contribution to the overall elimination of small proteins depended on the proteolytic activity in other body regions. For caplacizumab the fraction of the administered dose recovered in urine was negligible (<0.5%).

7.16.3 Elimination

The apparent clearance of caplacizumab varied with the administered dose. After a single intravenous dose of 10 mg in healthy volunteers, a mean clearance of 769±343 mL/h and a mean terminal half-life of 19.2±7.5 h were estimated using a model-independent method. The pharmacokinetics of caplacizumab after subcutaneous dosing appears to be absorption-controlled. After a single subcutaneous dose of 10 mg, the mean apparent clearance was 386±160 mL/h and the mean terminal half-life was 38.5±22.2 h in healthy volunteers.

7.16.4 Dose Proportionality

With increasing caplacizumab subcutaneous doses from 2 to 16 mg in healthy subjects, the increases in Cmax and AUC were less than dose proportional. For a dose increase ratio of 1.0:2.0:4.0:5.0:8.0, the mean Cmax ratio was 1.0:1.8:2.0:2.4:2.8 and the mean AUC increased in a ratio of 1.0:3.9:4.1:5.3:6.1.

The total clearance of caplacizumab depended on the drug and target levels and was the sum of a linear (catabolic) and non-linear (target-mediated) clearance. The terminal half-life of caplacizumab was also drug- and target-level dependent. In healthy volunteers, the mean apparent terminal half-life increased from 13 to 40 h after single intravenous dose (0.5 to 12 mg), and from 11 to 53 h after single subcutaneous administration (2 to 16 mg).

7.16.5 Effect of Demographic Factors and Body Size

The population pharmacokinetic analysis in aTTP patients showed that age, gender, race, and blood group did not affect the pharmacokinetics of caplacizumab. Bodyweight and renal function, as expressed by the creatinine clearance (CrCL), had a statistically significant effect on the pharmacokinetics, with an expected higher exposure in patients with a lower bodyweight and CrCL.

However, the expected exposure range in patient populations with extreme values of these covariates were largely overlapping, as shown in Table 7.16.5, and no specific dose-adjustment was deemed necessary. Baseline vWF levels have a statistically significant effect on drug exposure, but the increased drug exposure for patients with elevated vWF did not result in a different pharmacodynamic effect (change from baseline vWF level), and no individual dose-adjustment was deemed necessary (cf. also Examples 7.16.6 and 7.18).

TABLE 7.16.5

Simulated median steady-state pharmacokinetic exposure parameters (AUC, Cmax, Cmin) and corresponding pharmacodynamic effect (vWF:Ag change from baseline) following 40 days of 10 mg subcutaneous daily administration of caplacizumab in aTTP patients with low bodyweight, high baseline vWF levels and low CrCL.

| Parameter | aTTP patients | | |
|---|---|---|---|
| | BW = 50 kg | vWFb = 60 nM | CrCL = 15 mL/min |
| $AUC_\tau$, μg*h/mL median ($5^{th}$-$95^{th}$ %) | 13.3 (8.3 to 24.5) | 18.6 (11.9 to 33.4) | 13.3 (7.7 to 26.1) |
| $C_{max}$, μg/mL median ($5^{th}$-$95^{th}$ %) | 0.662 (0.424 to 1.159) | 0.895 (0.579 to 1.535) | 0.643 (0.389 to 1.193) |
| $C_{min}$, μg/mL median ($5^{th}$-$95^{th}$ %) | 0.452 (0.266 to 0.884) | 0.670 (0.409 to 1.260) | 0.468 (0.257 to 0.986) |
| $C_{avg}$, μg/mL median ($5^{th}$-$95^{th}$ %) | 0.555 (0.345 to 1.021) | 0.775 (0.498 to 1.391) | 0.554 (0.322 to 1.085) |
| $C_{avg}$, μg/mL median ($5^{th}$-$95^{th}$ %) | −45.4 (−69.2 to −1.3) | −43.8 (−67.8 to −0.6) | −45.2 (−68.4 to −1.9) | aTTP: acquired thrombotic thrombocytopenic purpura; $AUC_\tau$ area under the concentration-time curve over the dosing interval; BW: bodyweight; $C_{avg}$: average concentration; $C_{max}$: maximum concentration; $C_{min}$: minimum concentration; CrCL: creatinine clearance; vWF: von Willebrand factor; vWF:Ag: von Willebrand factor antigen.

7.16.6 Pharmacokinetic in Special Populations

No formal study with caplacizumab has been conducted in patients with severe acute or chronic hepatic impairment and no data regarding the use of caplacizumab in these populations were available. The risk associated with the use of caplacizumab in mild and moderate hepatically impaired patients was considered similar to the risk in the overall patient population, as the caplacizumab-vWF complex is expected to be cleared through the activated Kupffer cells rather than through the damaged hepatocellular parenchyma. However, caplacizumab should be used with caution in patients with severe hepatic impairment, presenting an increased risk of bleeding.

No formal study of the effect of renal impairment on the pharmacokinetics of caplacizumab has been conducted. In the population pharmacokinetic/pharmacodynamic model, renal function (baseline CrCL, range: 11.9 to >120 mL/min) had a statistically significant effect, which resulted in a limited increase in predicted exposure (AUCss) in severe renal impairment. In the clinical studies of patients with aTTP, those with decreased renal function did not show an additional risk of adverse events.

7.16.7 Drug-Drug Interactions

No in vitro drug-drug interaction study was conducted for caplacizumab, since Nanobodies, as single variable domain antibody fragments, are expected to be catabolized by ubiquitous proteolytic enzymes, and do not interact directly with cytochrome P450 isoforms or other metabolizing enzymes or transporters. While cytokine modulation may be an indirect mechanism through which Nanobodies could alter CYP expression, cytokine mediated CYP-related drug-drug interactions are unlikely for caplacizumab: the Nanobody® is not expected to have immune-modulatory properties as it selectively targets vWF.

Treatment of aTTP often involves the use of corticosteroids and rituximab with aspirin and low MW heparin sometimes used as thromboprophylaxis. More rarely, vincristine, cyclophosphamide, or cyclosporine, have been used in refractory disease. Except for rituximab, all these compounds are known to be cleared extensively by the liver through CYP-mediated pathways while the renal clearance pathway is only a minor route, and no drug-nanobody interaction is anticipated in case these treatments are initiated in combination with caplacizumab. As for other monoclonal antibodies, rituximab degradation occurs by non-specific high-capacity proteolysis, with no expected drug-drug interaction potential.

Caplacizumab selectively and specifically inhibits the A1 domain of vWF. In vitro, caplacizumab only partially competed with the binding of heparin to vWF. In vivo, pharmacodynamic interactions between co-administered heparin and caplacizumab were not expected to be clinically meaningful, since the main target effect of heparin is mediated by binding to the enzyme inhibitor antithrombin III.

7.16.8 Dose-Response Relationship

Studies in healthy volunteers after single ascending intravenous and single and repeated subcutaneous dose administration, confirmed the expected pharmacological response and safety of caplacizumab.

7.17 Effect of PE on the Pharmacokinetics and Pharmacodynamics of Caplacizumab.

Background: During clinical trials in patients with acquired thrombotic thrombocytopenic purpura, caplacizumab was administered as a 10 mg intravenous (i.v.) bolus prior to plasma exchange (PE), followed by 10 mg daily subcutaneous (s.c.) doses during the daily PE period and at least 30 days thereafter.

Aims: The potential effect of different time intervals between the first iv bolus and the subsequent PE, and the effect of different PE schedules, have been investigated.

Methods: An integrated pharmacokinetic (PK)/pharmacodymanic (PD) model was developed to describe the interaction between caplacizumab and vWF using non-linear mixed effects modeling and used to simulate the resulting PK and PD for different predetermined scenarios:

(1) PE start 3, 5, 11, 23 h post-caplacizumab 10 mg i.v. bolus
(2) PE schedule: daily and twice per day (bid) at the first day or during 7 days Results: Data from clinical trials indicated complete neutralization of vWF activity for caplacizumab plasma concentrations 500 ng/mL. Simulations suggested that median caplacizumab plasma levels would remain above this threshold if the PE starts up to 5 h post-caplacizumab i.v. bolus. For longer delays median caplacizumab plasma levels can fall below 500 ng/mL, and an additional 10 mg s.c. dose prior to PE can maintain an effective drug exposure.

Simulations of the effect of a bid PE for 7 days, suggested that the s.c. dosing schedule of caplacizumab during the PE period could be adjusted with bid 10 mg caplacizumab s.c. dosing after each PE treatment during the time of bid PE treatment.

Conclusions: Effective drug levels are expected if PE is started up to 5 h following the first i.v. dose of caplacizumab. For longer delays, an additional 10 mg s.c. dose prior to PE can be envisaged.

In case of bid PE for 7 days, the s.c. administration schedule of caplacizumab could be adjusted with bid caplacizumab after each PE treatment.

7.18 Caplacizumab Dosing Rational in aTTP Patients Supported by Mechanism Based PKPD Modelling Objectives: To describe the interplay between caplacizumab concentrations and its target, von Willebrand factor antigen (vWF:Ag) following treatment in different adult populations. The developed model should be utilized for simulations of what-if scenarios to support the dosing regimen.

Methods: The analysis was based on data from ten phase I to III studies[1-10] of caplacizumab in healthy volunteers (n=100), patients undergoing percutaneous coronary intervention (PCI) (n=225) and patients with acquired thrombotic thrombocytopenic purpura (n=216), with a total of 3629 PK and 6295 PD observations. The majority of the aTTP patients received plasma exchange (PE) and immunosuppressant treatment as standard of care. A wide range of dose levels, treatment and PE schedules were represented in the data. Data following both i.v. and s.c. administration were included.

The Population PKPD analysis was conducted by non-linear mixed-effects modelling using NONMEM, version 7.3.0. The model was developed stepwise. Initially, a subset of the data set including data in healthy volunteers and PCI patients was used for the model development. Subsequently, the model was updated to describe the specific characteristics related to the aTTP disease status and standard of care, PE, in the subset of the data set with aTTP patients. The effects of age, sex, race, blood group, body weight, creatinine clearance, and concomitant treatment were evaluated based on graphical evaluation by means of stratified prediction corrected visual predictive checks and univariate evaluation in NONMEM.

Simulations were performed using the final model for aTTP patients to evaluate the effect of change in doses, patient bodyweight, need of dose adjustment in paediatric patients Results: The interaction between caplacizumab and vWF:Ag was adequately described by a full target-mediated drug disposition model. The model included a two-compartment drug disposition model with a parallel slow and fast first-order absorption processes and first-order linear elimination of the free drug. The model described the formation of drug-vWF complexes with the ability to form both dimers and trimers. The production and maturation of vWF were described by transit compartments and storage of vWF in a pool compartment, mimicking the storage in the Weibel-Palade bodies in the endothelium and subsequent rapid release and elimination of free vWF. The half-life of free vWF was fixed to the literature value 16 hours (Lenting et al. 2015 Blood 26: 2019-2028; Favaloro et al. 2007 Thromb Haemost 97: 922-930; Dobrkovska et al. 1998 Haemophilia 4: 33-39; Goudemand et al. 2005 J Thromb Haemost 3: 2219-2227). A dual feedback mechanism was included, stimulating the production rate and release of vWF from the pool when vWF decreased below the subject's baseline level.

For aTTP patients, disease progression was captured as a transient increase in vWF:Ag over time and the effect of PE was described as parallel removal of free vWF, free drug and drug-vWF complex. The population typical total elimination rate under PE was estimated to be 3.7-fold higher for free drug, 3.5-fold higher for free vWF and 1.7-fold higher for the drug-vWF complex.

Body weight was allometrically included in the model (fixed exponents) and creatinine clearance was identified as a statistically significant covariate with a minor reduction in clearance for patients with CRCL below the median CRCL (100 ml/min) in aTTP patients.

The model was successfully applied to simulate what-if scenarios to support the dosing regimen, dosing in special populations and how to handle missed doses. Simulations were also performed to inform the dosing regimen in paediatric patients and to predict the PKPD behaviour in Japanese aTTP patients based on differences in body size. Simulations were also conducted to learn more about the impact of baseline vWF:Ag concentrations as well as the effect of the PE schedules in terms of timing, intensity, and duration.

Conclusions: A semi-mechanistic population PKPD model was developed to describe the interaction between caplacizumab and vWF (based on observations of vWF:Ag). The model adequately described the drug-vWF complex interaction over time, including disease progression in aTTP patients and the effects governed by PE treatment. The model has successfully been applied to increase the understanding of the PKPD interplay between caplacizumab and vWF in the target population, and by the use of simulations supported the dosing rational in both adult and paediatric patients and allowed bridging to Japanese aTTP patients.

7.19 Caplacizumab Model-Based Dosing Recommendations in Pediatric Patients with Acquired Thrombotic Thrombocytopenic Purpura Background: Acquired thrombotic thrombocytopenic purpura (aTTP) is a rare and life-threatening autoimmune blood clotting disorder, with a much lower incidence in children compared to adults. Caplacizumab has been evaluated in phase 2 and phase 3 randomized clinical trials in adult patients with aTTP.

Aims: As no pediatric patients were enrolled in clinical trials with caplacizumab, dosing recommendations were developed using model-based simulations for this population.

Methods: A semi-mechanistic pharmacokinetic-pharmacodynamic (PKPD) population model has been developed describing the interaction between caplacizumab and von Willebrand factor antigen (vWF:Ag) following intravenous and subcutaneous administration of caplacizumab in different adult populations at various dose levels using non-linear mixed effects modeling. Simulations based on the allometrically scaled PKPD model were performed to establish a suitable dosing regimen in adolescents and children >2 years. Eight age categories including 1000 individuals in each category were defined, and corresponding individual bodyweights were sampled from the National Health and Nutrition Examination Survey database. The simulated exposure levels of caplacizumab in the different age categories were compared to those predicted in adults.

Results: The simulations of exposure indicate that a flat 10 mg daily dosing would result in higher exposure in children with a low bodyweight, primarily children under 10 years of age. A dose adjustment to 5 mg daily to children with a body weight <40 kg would result in an on average similar exposure across age and weight groups. The bodyweight adjusted dosing is also predicted to result in highly similar suppression of vWF:Ag across the different age groups.

Conclusions: The recommended dose in adolescents 12-18 years with a body weight ≥40 kg is 10 mg, and 5 mg if <40 kg. Since no differences in vWF:Ag suppression are expected based on differences in age, the same dosing recommendation applies for children 2-12 years, 10 mg if the body weight is ≥40 kg and 5 mg if <40 kg.

7.20 Real-World Experience in aTTP Patients Treated with Caplacizumab Through a Managed Access Program Background: Acquired Thrombotic Thrombocytopenic Purpura (aTTP) is a life-threatening, immune-mediated thrombotic microangiopathy (TMA). The efficacy and safety of caplacizumab in patients with aTTP has been shown in randomized clinical trials.

Aims: We descriptively report on the first real-world experience with caplacizumab in aTTP patients, during a managed access program (MAP).

Methods: The eligibility criteria for the MAP were: (i) patient with an episode of aTTP, which (ii) could not be satisfactorily treated with approved therapies; (iii) the patient did not have a known hypersensitivity to the active substance or to any of the excipients and (iv) was not pregnant. Access to caplacizumab was granted in accordance with the laws and regulations effective in the country in which the product was requested. Safety related events were to be reported by the requesting physician, in accordance with all applicable national pharmacovigilance legislation.

Results: From May 14, 2018 until Jan. 22, 2019, 118 MAP requests were received, of which 75 were approved, 7 were refused, 35 were either not pursued/withdrawn by the requestor, and 1 was under evaluation. Of the approved requests, 67 patients received treatment with caplacizumab, while 8 ultimately did not start therapy. Patients received caplacizumab as frontline therapy or for the treatment of a refractory course of aTTP. Therapy was successfully completed in 37 patients, ongoing in 13 patients, and discontinued in 17 patients (of which 5 died). All deaths occurred in patients for which caplacizumab was initiated late, for a severe refractory course, and none were considered as related to caplacizumab. The spontaneous safety reports were in line with the safety profile observed in clinical studies, without new safety signals.

Conclusions: The first real world evidence with caplacizumab in aTTP patients confirm the important benefits of caplacizumab observed in clinical trials, particularly if started as frontline therapy.

7.21 New Formats

A modified anti-drug-antibody (mADA) assay was used to detect drug-induced treatment-emergent ADA. The mADA employs a modified caplacizumab molecule as detection reagent in the bridging format, i.e. caplacizumab-ALA variant (SEQ ID NO: 24). The C-terminally Alanine-extended caplacizumab did not bind any pre-existing antibodies.

In various in vitro experiments caplacizumab and the C-terminal Alanine-extended caplacizumab behaved equivalent.

By means of comparative nuclear magnetic resonance (NMR) analyses of 12A2H1 (the building block of caplacizumab; SEQ ID NO: 19) it was demonstrated that a C-terminal extension (Alanine) does not impact the conformation of the Nanobody as a whole.

Furthermore, on Surface Plasmon Resonance (SPR) a similar binding profile of caplacizumab and C-terminal Alanine-extended caplacizumab to the target (vWF) was demonstrated.

In view of the similar characteristics and profiles between caplacizumab and C-terminally extended caplacizumab, it is expected that these C-terminally extended caplacizumab compounds can be used in treating and/or preventing aTTP as well similar to caplacizumab.

7.22 Conclusion.

Over the last two decades, despite an increased understanding of the pathophysiology of aTTP and the use of newer immunosuppressants, treatment outcomes have not changed, with significant morbidity and reported mortality rates as high as 20% (Joly et al. 2017 Blood 129:2836-2846). Caplacizumab, a Nanobody directed against the A1 domain of vWF, blocks vWF-platelet adhesion and aggregation, and prevents the further consumption of platelets in the microthrombi that cause the severe thrombocytopenia and tissue and organ damage in aTTP.

aTTP remains a clinical diagnosis based on patient history, physical examination and review of a peripheral blood smear. Indeed patients with an initial aTTP episode have a delayed presentation and more severe disease at baseline than those with recurrent disease episodes.

In this study, patients with a clinical diagnosis of aTTP were eligible for enrollment, and confirmatory ADAMTS13 activity testing was done at randomization. The clinical diagnosis was confirmed by ADAMTS13 activity below 10% in 86% of those randomized. Moreover, for 13 of the 20 patients with ADAMTS13 activity above 10% at baseline, there was a basis for a TTP diagnosis, such as a history of TTP or suppressed ADAMTS13 activity at other time points during the study.

In the phase 2 TITAN study, treatment with caplacizumab led to a faster normalization of platelet counts and prevented exacerbations. However, early relapses occurred in a subset of patients with unresolved underlying disease activity. Therefore, in the current study, investigators were encouraged to extend blinded study drug treatment together with optimization of immunosuppression in those patients with evidence of persistent autoimmune activity.

The phase 3 HERCULES study results confirmed the hypothesis that treatment with caplacizumab reduces the time to platelet count response by stopping the consumption of platelets in microthrombi. They also demonstrated the highly clinically meaningful impact of caplacizumab on TTP-related death, TTP recurrence, or a major thromboembolic event while on study drug treatment, and on recurrences overall. The approach of extending study drug treatment and optimizing immunosuppression in patients with evidence of unresolved underlying disease was validated by the results of this study, as demonstrated by the lower number of recurrences after study drug treatment, compared to that observed in the phase 2 study. Indeed, the relapses observed after stop of study drug were all in patients with ADAMTS13 activity below 10%. In a real world setting, to protect such patients from relapse of aTTP, treatment with caplacizumab should be extended until the underlying disease is resolved.

Even in the more serious disease setting of patients experiencing an initial aTTP episode, it was shown that treatment with caplacizumab improved the outcome, including faster time to platelet count response, lower proportion of patients with either death, recurrence or a major TE event during the treatment period, lower recurrence rate during the overall treatment period, and prevention of refractoriness compared to placebo.

In both the phase 2 and phase 3 studies, there were no deaths reported during treatment with caplacizumab, a favorable outcome with respect to mortality prevention. In addition, no caplacizumab-treated patients were refractory to plasma exchange. This suggests that caplacizumab has the potential to prevent refractory disease and the worse outcomes reported in this subpopulation. In patients treated with caplacizumab, there was also a trend towards faster normalization of the markers associated with organ damage.

The impact of treatment with caplacizumab on time to platelet count response and prevention of recurrences was associated with considerable savings in healthcare resources.

Caplacizumab interferes with vWF, a key protein in hemostasis, and based on this pharmacologic effect, it is associated with an increased risk of mucocutaneous bleeding, similar to that observed in von Willebrand Disease (Leebeek & Eikenboom 2016 N Engl J Med 375:2067-2080). Safety results were in line with what has been reported previously.

ADAMTS13 activity is increasingly relevant in the management of aTTP, as it is a predictive marker of risk for recurrence (Westwood et al. 2013 J Thromb Haemost 11:481-490; Peyvandi et al. 2008 Haematologica 93:232-239; Lammle et al. 2008 Haematologica 93:172-177; Knovich et al. 2012 Eur J Haematol 88:518-525; Kremer Hovinga et al. 2010 Blood 115:1500-1511; quiz 662; Bresin et al. 2009 Thromb Haemost 101:233-238; Cataland et al. 2009 Eur J Haematol 83:559-564; Goyal et al. 2013 J Clin Apher 28:390-394). Its value was confirmed in the current study as nearly all patients with recurrences had suppressed ADAMTS13 activity. Over 50% of patients had not yet achieved normalization of ADAMTS13 activity at the end of the plasma exchange period, and exacerbations occurred up to 25 days after the end of plasma exchange in this group, supporting the need to continue treatment with caplacizumab for at least 30 days after platelet count response is achieved.

Caplacizumab, through rapid blocking of vWF-mediated platelet adhesion, represents an important addition to the treatment armamentarium for patients with aTTP.

TABLE A-1

Examples of polypeptides comprising ISVDs and CDRs against vWF

| Name | SEQ ID NO | Sequence |
|---|---|---|
| 12A02H1-3a-12A02H1 (ALX 0081) | 1 | EVQLVESGGGLVQPGGSLRLSCAASGRTFSYNPMGWFRQAPGKGRELVA AISRTGGSTYYPDSVEGRFTISRDNAKRMVYLQMNSLRAEDTAVYYCAAA GVRAEDGRVRTLPSEYTFWGQGTQVTVSSAAAEVQLVESGGGLVQPGG SLRLSCAASGRTFSYNPMGWFRQAPGKGRELVAAISRTGGSTYYPDSVEG RFTISRDNAKRMVYLQMNSLRAEDTAVYYCAAAGVRAEDGRVRTLPSEYT FWGQGTQVTVSS |
| 12A02-3a-12A02 | 2 | QVKLEESGGGLVQAGGALRLSCAASGRTFSYNPMGWFRQAPGKERDLV AAISRTGGSTYYPDSVEGRFTISRDNAKRMVYLQMNNLKPEDTAVYYCAA AGVRAEDGRVRTLPSEYTFWGQGTQVTVSSAAAEVQLVESGGGLVQAG GALRLSCAASGRTFSYNPMGWFRQAPGKERDLVAAISRTGGSTYYPDSVE GRFTISRDNAKRMVYLQMNNLKPEDTAVYYCAAAGVRAEDGRVRTLPSE YTFWGQGTQVTVSS |
| 12A02-GS9-12A02 | 3 | QVKLEESGGGLVQAGGALRLSCAASGRTFSYNPMGWFRQAPGKERDLV AAISRTGGSTYYPDSVEGRFTISRDNAKRMVYLQMNNLKPEDTAVYYCAA AGVRAEDGRVRTLPSEYTFWGQGTQVTVSSGGGGSGGGSEVQLVESGG GLVQAGGALRLSCAASGRTFSYNPMGWFRQAPGKERDLVAAISRTGGST YYPDSVEGRFTISRDNAKRMVYLQMNNLKPEDTAVYYCAAAGVRAEDGR VRTLPSEYTFWGQGTQVTVSS |
| 12A02-GS30-12A02 | 4 | QVKLEESGGGLVQAGGALRLSCAASGRTFSYNPMGWFRQAPGKERDLV AAISRTGGSTYYPDSVEGRFTISRDNAKRMVYLQMNNLKPEDTAVYYCAA AGVRAEDGRVRTLPSEYTFWGQGTQVTVSSGGGGSGGGGSGGGGSGG GGSGGGGSGGGGSEVQLVESGGGLVQAGGALRLSCAASGRTFSYNPMG WFRQAPGKERDLVAAISRTGGSTYYPDSVEGRFTISRDNAKRMVYLQMN NLKPEGTAVYYCAAAGVRAEDGRVRTLPSEYTFWGQGTQVTVSS |
| 12A05-3a-12A05 | 5 | AVQLVESGGGLVQPGGSLRLSCLASGRIFSIGAMGMYRQAPGKQRELVA TITSGGSTNYADPVKGRFTISRDGPKNTVYLQMNSLKPEDTAVYYCYANLK QGSYGYRFNDYWGQGTQVTVSSAAAEVQLVESGGGLVQPGGSLRLSCLA SGRIFSIGAMGMYRQAPGKQRELVATITSGGSTNYADPVKGRFTISRDGP KNTVYLQMNSLKPEDTAVYYCYANLKQGSYGYRFNDYWGQGTQVTVSS |
| 12A05-GS9-12A05 | 6 | AVQLVESGGGLVQPGGSLRLSCLASGRIFSIGAMGMYRQAPGKQRELVA TITSGGSTNYADPVKGRFTISRDGPKNTVYLQMNSLKPEDTAVYYCYANLK QGSYGYRFNDYWGQGTQVTVSSGGGGSGGGSEVQLVESGGGLVQPGG SLRLSCLASGRIFSIGAMGMYRQAPGKQRELVATITSGGSTNYADPVKGRF TISRDGPKNTVYLQMNSLKPEDTAVYYCYANLKQGSYGYRFNDYWGQGT QVTVSS |

TABLE A-1-continued

Examples of polypeptides comprising ISVDs and CDRs against vWF

| Name | SEQ ID NO | Sequence |
|---|---|---|
| 12A05-GS30-12A05 | 7 | AVQLVESGGGLVQPGGSLRLSCLASGRIFSIGAMGMYRQAPGKQRELVA TITSGGSTNYADPVKGRFTISRDGPKNTVYLQMNSLKPEDTAVYYCYANLK QGSYGYRFNDYWGQGTQVTVSSGGGGSGGGGSGGGGSGGGGSGGGG SGGGGSEVQLVESGGGLVQPGGSLRLSCLASGRIFSIGAMGMYRQAPGK QRELVATITSGGSTNYADPVKGRFTISRDGPKNTVYLQMNSLKPEDTAVYY CYANLKQGSYGYRFNDYWGQGTQVTVSS |
| 12B06-3a-12B06 | 8 | QVQLVESGGGLVQAGGALRLSCAASGRTFSYNPMGWFRQAPGKERDVV AAISRTGGSTYYARSVEGRFTISRDNAKRMVYLQMNALKPEDTAVYYCAA AGVRAEDGRVRTLPSEYNFWGQGTQVTVSSAAAEVQLVESGGGLVQAG GALRLSCAASGRTFSYNPMGWFRQAPGKERDVVAAISRTGGSTYYARSV EGRFTISRDNAKRMVYLQMNALKPEDTAVYYCAAAGVRAEDGRVRTLPS EYNFWGQGTQVTVSS |
| 12B06-GS9-12B06 | 9 | QVQLVESGGGLVQAGGALRLSCAASGRTFSYNPMGWFRQAPGKERDVV AAISRTGGSTYYARSVEGRFTISRDNAKRMVYLQMNALKPEDTAVYYCAA AGVRAEDGRVRTLPSEYNFWGQGTQVTVSSGGGGSGGGSEVQLVESGG GLVQAGGALRLSCAASGRTFSYNPMGWFRQAPGKERDVVAAISRTGGST YYARSVEGRFTISRDNAKRMVYLQMNALKPEDTAVYYCAAAGVRAEDGR VRTLPSEYNFWGQGTQVTVSS |
| 12B06-GS30-12B06 | 10 | QVQLVESGGGLVQAGGALRLSCAASGRTFSYNPMGWFRQAPGKERDVV AAISRTGGSTYYARSVEGRFTISRDNAKRMVYLQMNALKPEDTAVYYCAA AGVRAEDGRVRTLPSEYNFWGQGTQVTVSSGGGGSGGGGSGGGGSGG GGSGGGGSGGGGSEVQLVESGGGLVQAGGALRLSCAASGRTFSYNPMG WFRQAPGKERDVVAAISRTGGSTYYARSVEGRFTISRDNAKRMVYLQMN ALKPEDTAVYYCAAAGVRAEDGRVRTLPSEYNFWGQGTQVTVSS |
| 12A02H4-3a-12A02H4 | 11 | EVQLVESGGGLVQPGGSLRLSCAASGRTFSYNPMGWFRQAPGKGRELVA AISRTGGSTYYPDSVEGRFTISRDNAKRSVYLQMNSLRAEDTAVYYCAAAG VRAEDGRVRTLPSEYTFWGQGTQVTVSSAAAEVQLVESGGGLVQPGGSL RLSCAASGRTFSYNPMGWFRQAPGKGRELVAAISRTGGSTYYPDSVEGRF TISRDNAKRSVYLQMNSLRAEDTAVYYCAAAGVRAEDGRVRTLPSEYTFW GQGTQVTVSS |
| 12B06H2-3a-12B06H2 | 12 | EVQLVESGGGLVQPGGSLRLSCAASGRTFSYNPMGWFRQAPGKGREVV AAISRTGGSTYYARSVEGRFTISRDNAKRMVYLQMNSLRAEDTAVYYCAA AGVRAEDGRVRTLPSEYNFWGQGTQVTVSSAAAEVQLVESGGGLVQPG GSLRLSCAASGRTFSYNPMGWFRQAPGKGREVVAAISRTGGSTYYARSVE GRFTISRDNAKRMVYLQMNSLRAEDTAVYYCAAAGVRAEDGRVRTLPSE YNFWGQGTQVTVSS |
| 12A02H1-GS9-12A02H1 | 13 | EVQLVESGGGLVQPGGSLRLSCAASGRTFSYNPMGWFRQAPGKGRELVA AISRTGGSTYYPDSVEGRFTISRDNAKRMVYLQMNSLRAEDTAVYYCAAA GVRAEDGRVRTLPSEYTFWGQGTQVTVSSGGGGSGGGSEVQLVESGGG LVQPGGSLRLSCAASGRTFSYNPMGWFRQAPGKGRELVAAISRTGGSTYY PDSVEGRFTISRDNAKRMVYLQMNSLRAEDTAVYYCAAAGVRAEDGRVR TLPSEYTFWGQGTQVTVSS |
| 12A02H4-GS9-12A02H4 | 14 | EVQLVESGGGLVQPGGSLRLSCAASGRTFSYNPMGWFRQAPGKGRELVA AISRTGGSTYYPDSVEGRFTISRDNAKRSVYLQMNSLRAEDTAVYYCAAAG VRAEDGRVRTLPSEYTFWGQGTQVTVSSGGGGSGGGSEVQLVESGGGL VQPGGSLRLSCAASGRTFSYNPMGWFRQAPGKGRELVAAISRTGGSTYY PDSVEGRFTISRDNAKRSVYLQMNSLRAEDTAVYYCAAAGVRAEDGRVRT LPSEYTFWGQGTQVTVSS |
| 12B06H2-GS9-12B06H2 | 15 | EVQLVESGGGLVQPGGSLRLSCAASGRTFSYNPMGWFRQAPGKGREVV AAISRTGGSTYYARSVEGRFTISRDNAKRMVYLQMNSLRAEDTAVYYCAA AGVRAEDGRVRTLPSEYNFWGQGTQVTVSSGGGGSGGGSEVQLVESGG GLVQPGGSLRLSCAASGRTFSYNPMGWFRQAPGKGREVVAAISRTGGST YYARSVEGRFTISRDNAKRMVYLQMNSLRAEDTAVYYCAAAGVRAEDGR VRTLPSEYNFWGQGTQVTVSS |
| 12A02H1-GS30-12A02H1 | 16 | EVQLVESGGGLVQPGGSLRLSCAASGRTFSYNPMGWFRQAPGKGRELVA AISRTGGSTYYPDSVEGRFTISRDNAKRMVYLQMNSLRAEDTAVYYCAAA GVRAEDGRVRTLPSEYTFWGQGTQVTVSSGGGGSGGGGSGGGGSGGG GSGGGGGGGSEVQLVESGGGLVQPGGSLRLSCAASGRTFSYNPMGW FRQAPGKGRELVAAISRTGGSTYYPDSVEGRFTISRDNAKRMVYLQMNSL RAEDTAVYYCAAAGVRAEDGRVRTLPSEYTFWGQGTQVTVSS |

TABLE A-1-continued

Examples of polypeptides comprising ISVDs and CDRs against vWF

| Name | SEQ ID NO | Sequence |
|---|---|---|
| 12A02H4-GS30-12A02H4 | 17 | EVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSSGGGGSGGGGSGGGGSGGGGSGGGGSGGGGSEVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSS |
| 12B06H2-GS30-12B06H2 | 18 | EVQLVESGGGLVQPGGSLRLSCAASGRTFSYNPMGWFRQAPGKGREVVAAISRTGGSTYYARSVEGRFTISRDNAKRMVYLQMNSLRAEDTAVYYCAAAGVRAEDGRVRTLPSEYNFWGQGTQVTVSSGGGGSGGGGSGGGGSGGGGSGGGGSEVQLVESGGGLVQPGGSLRLSCAASGRTFSYNPMGWFRQAPGKGREVVAAISRTGGSTYYARSVEGRFTISRDNAKRMVYLQMNSLRAEDTAVYYCAAAGVRAEDGRVRTLPSEYNFWGQGTQVTVSS |
| 12A02H1 | 19 | EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSS |
| 12A02H1 CDR1 | 21 | YNPMG |
| 12A02H1 CDR2 | 22 | AISRTGGSTYYPDSVEG |
| 12A02H1 CDR3 | 23 | AGVRAEDGRVRTLPSEYTF |
| ALX 0081-A | 24 | EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSSAAAEVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSSA |

TABLE A-2

| Name | SEQ ID NO | Sequence |
|---|---|---|
| Human vWF | 20 | MIPARFAGVLLALALILPGTLCAEGTRGRSSTARCSLFGSDFVNTFDGSMYSFAGYCSYLLAGGCQKRSFSIIGDFQNGKRVSLSVYLGEFFDIHLFVNGTVTQGDQRVSMPYASKGLYLETEAGYYKLSGEAYGFVARIDGSGNFQVLLSDRYFNKTCGLCGNFNIFAEDDFMTQEGTLTSDPYDFANSWALSSGEQWCERASPPSSSCNISSGEMQKGLWEQCQLLKSTSVFARCHPLVDPEPFVALCEKTLCECAGGLECACPALLEYARTCAQEGMVLYGWTDHSACSPVCPAGMEYRQCVSPCARTCQSLHINEMCQERCVDGCSCPEGQLLDEGLCVESTECPCVHSGKRYPPGTSLSRDCNTCICRNSQWICSNEECPGECLVTGQSHFKSFDNRYFTSGICQYLLARDCQDHSFSIVIETVQCADDRDAVCTRSVTVRLPGLHNSLVKLKHGAGVAMDGQDIQLPLLKGDLRIQHTVTASVRLSYGEDLQMDWDGRGRLLVKLSPVYAGKTCGLCGNYNGNQGDDFLTPSGLAEPRVEDFGNAWKLHGDCQDLQKQHSDPCALNPRMTRFSEEACAVLTSPTFEACHRAVSPLPYLRNCRYDVCSCSDGRECLCGALASYAAACAGRGVRVAWREPGRCELNCPKGQVYLQCGTPCNLTCRSLSYPDEECNEACLEGCFCPPGLYMDERGDCVPKAQCPCYYDGEIFQPEDIFSDHHTMCYCEDGFMHCTMSGVPGSLLPDAVLSSPLSHRSKRSLSCRPPMVKLVCPADNLRAEGLECTKTCQNYDLECMSMGCVSGCLCPPGMVRHENRCVALERCPCFHQGKEYAPGETVKIGCNTCVCRDRKWNCTDHVCDATCSTIGMAHYLTFDGLKYLFPGECQYVLVQDYCGSNPGTFRILVGNKGCSHPSVKCKKRVTILVEGGEIELFDGEVNVKRPMKDETHFEVVESGRYIILLLGKALSVVWDRHLSISVVLKQTYQEKVCGLCGNFDGIQNNDLTSSNLQVEEDPVDFGNSWKVSSQCADTRKVPLDSSPATCHNNIMKQTMVDSSCRILTSDVFQDCNKLVDPEPYLDVCIYDTCSCESIGDCACFCDTIAAYAHVCAQHGKVVTWRTATLCPQSCEERNLRENGYECEWRYNSCAPACQVTCQHPEPLACPVQCVEGCHAHCPPGKILDELLQTCVDPEDCPVCEVAGRRFASGKKVTLNPSDPEHCQICHCDVVNLTCEACQEPGGLVVPPTDAPVSPTTLYVEDISEPPLHDFYCSRLLDLVFLLDGSSRLSEAEFEVLKAFVVDMMERLRISQKWVRVAVVEYHDGSHAYIGLKDRKRPSELRRIASQVKYAGSQVASTSEVLKYTLFQIFSKIDRPEASRIALLLMASQEPQRMSRNFVRYVQGLKKKKVIVIPVGIGPHANLKQIRLIEKQAPENKAFVLSSVDELEQQRDEIVSYLCDLAPEAPPPTLPPHMAQVTVGPGLRNSMVLDVAFVLEGSDKIGEADFNRSKEFMEEVIQRMDVGQDSIHVTVLQYSYMVTVEYPFSEAQSKGDILQRVREIRYQGGNRTNTGLALRYLSDHSFLVSQGDREQAPNLVYMVTGNPASDEIKRLPGDIQVVPIGVGPNANVQELERIGWPNAPILIQDFETLPREAPDLVLQRCCSGEGLQIPTLSPAPDCSQPLDVILLLDGSSSFPASYFDEMKSFAKAFISKANIGPRLTQVSVLQYGSITTIDVPWNVVPEKAHLLSLVDVMQREGGPSQIGDALGFAVRYLTSEMHGARPGASKAVVILVTDVSVDSVDAAADAARSNRVTVFPIGIGDRYDAAQLRILAGPAGDSNVVKLQRIEDLPTMVTLGNSFLHKLCSGFVRICMDEDGNEKRPGDVWTLPDQCHTVTCQPDGQTLLKSHRVNCDRGLRPSCPNSQSPVKVEETCGCRWTCPCVCTGSSTRHIVTFDGQNFKLTGSCSYVLFQNKEQDLEVILHNGACSPGARQGCMKSIEVKHSALSVELHSDMEVTVNGRLVS |

TABLE A-2-continued

| Name | SEQ ID NO | Sequence |
|---|---|---|
| | | VPYVGGNMEVNVYGAIMHEVRFNHLGHIFTFTPQNNEFQLQLSPKTFASKTYGLCGICDEN GANDFMLRDGTVTTDWKTLVQEWTVQRPGQTCQPILEEQCLVPDSSHCQVLLLPLFAECH KVLAPATFYAICQQDSCHQEQVCEVIASYAHLCRTNGVCVDWRTPDFCAMSCPPSLVYNH CEHGCPRHCDGNVSSCGDHPSEGCFCPPDKVMLEGSCVPEEACTQCIGEDGVQHQFLEA WVPDHQPCQICTCLSGRKVNCTTQPCPTAKAPTCGLCEVARLRQNADQCCPEYECVCDPV SCDLPPVPHCERGLQPTLTNPGECRPNFTCACRKEECKRVSPPSCPPHRLPTLRKTQCCDEY ECACNCVNSTVSCPLGYLASTATNDCGCTTTTCLPDKVCVHRSTIYPVGQFWEEGCDVCTC TDMEDAVMGLRVAQCSQKPCEDSCRSGFTYVLHEGECCGRCLPSACEVVTGSPRGDSQSS WKSVGSQWASPENPCLINECVRVKEEVFIQQRNVSCPQLEVPVCPSGFQLSCKTSACCPSC RCERMEACMLNGTVIGPGKTVMIDVCTTCRCMVQVGVISGFKLECRKTTCNPCPLGYKEE NNTGECCGRCLPTACTIQLRGGQIMTLKRDETLQDGCDTHFCKVNERGEYFWEKRVTGCP PFDEHKCLAEGGKIMKIPGTCCDTCEEPECNDITARLQYVKVGSCKSEVEVDIHYCQGKCAS KAMYSIDINDVQDQCSCCSPTRTEPMQVALHCTNGSVVYHEVLNAMECKCSPRKCSK |

TABLE 5

| Abbreviation | Explanation |
|---|---|
| ACS | acute coronary syndrome |
| ADAMTS13 | a disintegrin-like and metalloprotease with thrombospondin repeats 13 |
| ALX 0081 | Caplacizumab (SEQ ID NO: 1) |
| ALX 0081-A | caplacizumab plus C-terminal alanine (SEQ ID NO: 24) |
| aTTP | acquired thrombotic thrombocytopenic purpura |
| AUC | area under the curve |
| bid | twice a day |
| BNP | brain natriuretic peptide |
| CAP | Caplacizumab (SEQ ID NO: 1) |
| CDR | complementarity determining region |
| cIEF | Capillary IsoElectric Focusing |
| Cmax | maximal concentrations |
| CrCL | creatinine clearance |
| cTnI | cardiac troponin I |
| cTnT | cardiac troponin T |
| dAb | single domain antibody |
| DB | double-blind |
| DVT | deep venous thrombosis |
| ECG | electrocardiogram |
| EIA | enzyme immunoassay |
| ELISA | enzyme-linked immunosorbent assay |
| FACS | Fluorescent activated cell sorting |
| ICF | Informed Consent Form |
| ICU | Intensive Care Unit |
| ISVD | Immunoglobulin single variable domain |
| i.v. | intravenous |
| FR | framework region |
| FRET | fluorescence resonance energy transfer |
| FU | Follow-up |
| GCS | Glasgow coma scale |
| GST | Glutathion-S-transferase |
| HUS | haemolytic uraemic syndrome |
| KA | association constant |
| KD | dissociation constant |
| LDH | Lactate dehydrogenase |
| LMWH | low molecular weight heparin |
| MAHA | microangiopathic hemolytic anemia |
| MAHAT | microangiopathic hemolytic anemia and thrombocytopenia |
| MI | myocardial infarction |
| MAP | managed access program |
| NCA | non-compartmental analysis |
| NMR | nuclear magnetic resonance |
| NSE | neuron specific enolase |
| NT proBNP | N-terminal pro brain natriuretic peptide |
| OL | Open-label |
| PCI | percutaneous coronary intervention |
| PE or PEX | plasma exchange |
| PKPD | pharmacokinetic-pharmacodynamic |
| RIA | radioimmunoassays |
| RICO | Ristocetin cofactor activity |
| RIPA | ristocetin platelet aggregation |
| RP-HPLC | Reverse Phase High Performance Liquid Chromatography |
| SAE | serious adverse event |
| s.c. | subcutaneous |
| scFv | single chain variable fragment |
| SD | standard deviation |
| S/D | Solvent/Detergent |
| SE-HPLC | Size Exclusion High Performance Liquid Chromatography |
| SPR | surface plasmon resonance |
| TE | Thromboembolic event |
| TMA | thrombotic microangiopathy |
| TnI | troponin I |
| TnT | troponin T |
| TTP | Thrombotic thrombocytopenic purpura |
| TRALI | Transfusion related acute lung injury |
| TTP | Thrombotic thrombocytopenic purpura |
| ULN | Upper limit normal |
| ULvWF | ultra-large vWF |
| VH | heavy chain variable domain |
| VHH | heavy chain variable domain sequence that is derived from a heavy chain antibody |
| VL | light chain variable domain |
| vWF | von Willebrand Factor |

The invention claimed is:

1. A method of treating an initial episode of a von Willebrand Factor (vWF)-related disease comprising administering to a human experiencing an initial episode of the vWF-related disease a polypeptide comprising two anti-human vWF immunoglobulin single variable domains (ISVDs),
   wherein the human is 2-18 years old and has a body weight of <40 kg,
   wherein the polypeptide is administered in a dose of 5 mg,
   wherein each of the anti-human vWF ISVDs consists of 4 framework regions (FR1 to FR4, respectively) and 3 complementarity determining regions (CDR1 to CDR3, respectively), and
   wherein at least one of the anti-human vWF ISVDs is represented by SEQ ID NO: 19.

2. The method according to claim 1, wherein said step of administering the polypeptide is repeated for at least 1 day.

3. The method according to claim 2, wherein said treatment results in a faster time to platelet count response, lower proportion of patients with either death, recurrence or a major thromboembolic event (TE) event during the treatment period, lower recurrence rate, and/or prevention of refractoriness.

4. The method according to claim 1, wherein said polypeptide comprises at least one ISVD binding SEQ ID NO: 20.

5. The method according to claim 1, wherein each of the anti-human vWF ISVDs comprises:
   a) a CDR1 comprising or consisting essentially of the amino acid sequence YNPMG (SEQ ID NO: 21);
   b) a CDR2 comprising or consisting essentially of the amino acid sequence AISRTGGSTYYPDSVEG (SEQ ID NO: 22); and
   c) a CDR3 comprising or consisting essentially of the amino acid sequence AGVRAEDGRVRTLPSEYTF (SEQ ID NO: 23).

6. The method according to claim 1, wherein said polypeptide is at least 90% identical to SEQ ID NO: 1.

7. The method according to claim 1, wherein said polypeptide is ALX 0081 (SEQ ID NO: 1) or ALX 0081-A (SEQ ID NO: 24).

8. The method according to claim 1, wherein said dose is administered 1 time per day or two times per day.

9. The method according to claim 1, comprising repeating administering said polypeptide until the platelet number in said human is at least 150,000/μl.

10. The method according to claim 9, comprising repeating administering said polypeptide until the platelet number in said human is at least 150,000/μl on at least 2 consecutive measurements.

11. The method according to claim 10, wherein said step of administering the polypeptide is repeated for at least 1 day after said platelet number is at least 150,000/μl on at least 2 consecutive measurements.

12. The method according to claim 10, wherein said 2 consecutive measurements are at least 24 h apart.

13. The method according to claim 1, comprising repeating administering said polypeptide until the ADAMTS13 activity in said human is at least 10% of an ADAMTS13 reference activity.

14. The method according to claim 1, comprising repeating administering said polypeptide until the level of an organ damage marker in said human returns to at least 40% of normal levels.

15. The method according to claim 1, comprising performing a Plasma Exchange.

16. The method according to claim 1, wherein said vWF-related disease is acute coronary syndrome (ACS), transient cerebral ischemic attack, unstable or stable angina pectoris, stroke, myocardial infarction or thrombotic thrombocytopenic purpura (TTP).

17. The method according to claim 1, comprising using a kit or an article of manufacture, comprising a container containing the polypeptide, and instructions for use.

18. The method of claim 1, further comprising performing a Plasma Exchange within 5 hours following administration of the polypeptide.

19. The method according to claim 14, wherein the organ damage marker is LDH level, troponin T level, troponin I level, and/or creatinine level.

20. The method according to claim 1, wherein said vWF-related disease is thrombotic thrombocytopenic purpura (TTP).

* * * * *

UNITED STATES PATENT AND TRADEMARK OFFICE
CERTIFICATE OF CORRECTION

| | | |
|---|---|---|
| PATENT NO. | : 11,999,797 B2 | Page 1 of 1 |
| APPLICATION NO. | : 16/967514 | |
| DATED | : June 4, 2024 | |
| INVENTOR(S) | : Callewaert et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this
Twelfth Day of November, 2024

Katherine Kelly Vidal
*Director of the United States Patent and Trademark Office*